United States Patent
Gupta

(10) Patent No.: US 9,880,081 B1
(45) Date of Patent: Jan. 30, 2018

(54) EXPANDABLE JACKET FOR TRIAXIAL, UNCONFINED AND UNIAXIAL COMPRESSION TESTS AND TEST DEVICE FOR THREE-DIMENSIONAL CONSOLIDATION AND SETTLEMENT TESTS

(71) Applicant: Ramesh Chandra Gupta, Ashburn, VA (US)

(72) Inventor: Ramesh Chandra Gupta, Ashburn, VA (US)

( * ) Notice: Subject to any disclaimer, the term of this patent is extended or adjusted under 35 U.S.C. 154(b) by 0 days.

(21) Appl. No.: 15/452,267

(22) Filed: Mar. 7, 2017

(51) Int. Cl.
   *G01N 19/06* (2006.01)
   *G01N 3/08* (2006.01)
   *G01N 3/06* (2006.01)
   *G01N 33/24* (2006.01)

(52) U.S. Cl.
   CPC .............. *G01N 3/08* (2013.01); *G01N 3/066* (2013.01); *G01N 33/24* (2013.01)

(58) Field of Classification Search
   None
   See application file for complete search history.

(56) References Cited

U.S. PATENT DOCUMENTS

| | | | | |
|---|---|---|---|---|
| 4,542,655 A | * | 9/1985 | Park | G01B 5/30 73/152.59 |
| 5,025,668 A | * | 6/1991 | Sarda | G01N 3/10 73/795 |
| 9,567,722 B2 | * | 2/2017 | Gupta | E02D 1/025 |

* cited by examiner

*Primary Examiner* — Andre Allen

(57) ABSTRACT

The expandable jacket consists of the rubber membrane surrounding the cylindrical specimen, circular segmental metal plates surrounding the rubber membrane, and elastomeric rubber bands or rings around the segmental plates to permit uniform radial expansion and maintain uniform diameter of the specimen during the test and thereby providing accurate values of deviator stress, volume change characteristics and shear strength of soil specimen. To determine the three-dimensional coefficient of consolidation and coefficient of consolidation in horizontal direction, the flexible ring consists of all above structural components of expandable jacket except that a filter fabric or paper is wrapped around the cylindrical specimen, and then rubber membrane is mounted surrounding the filter paper or paper. The calibration device for calibration of the expandable jacket and flexible ring shall provide the magnitude of correction to be made in deviator stress and lateral resistance provided by the rubber bands or rings during the test.

31 Claims, 22 Drawing Sheets

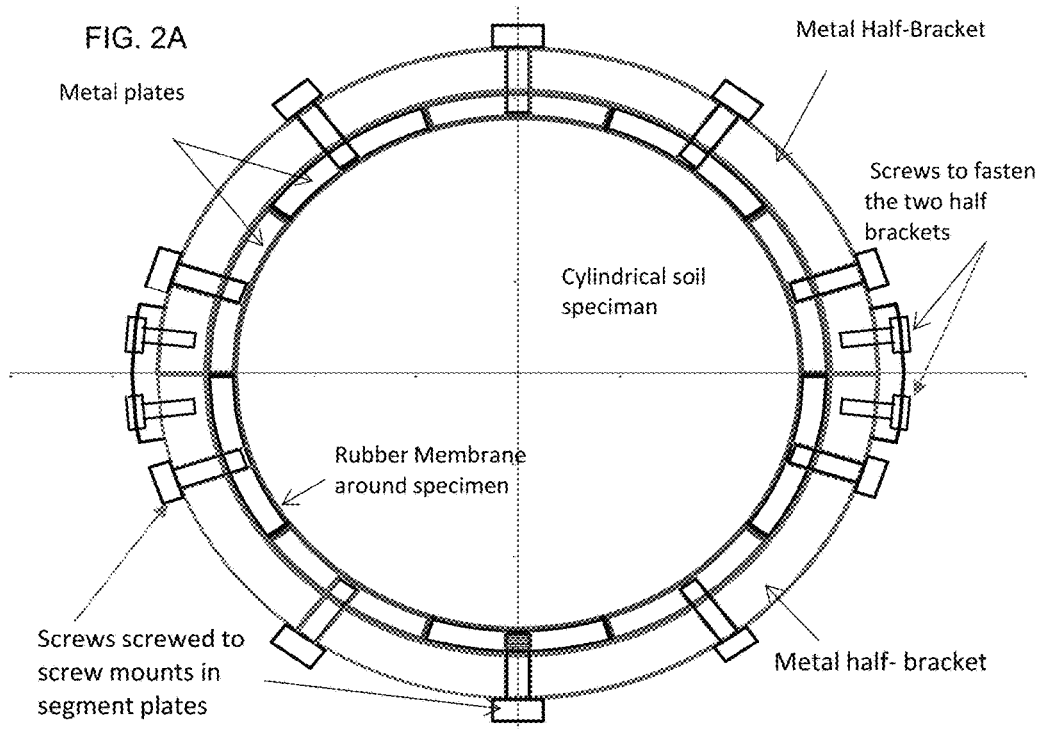
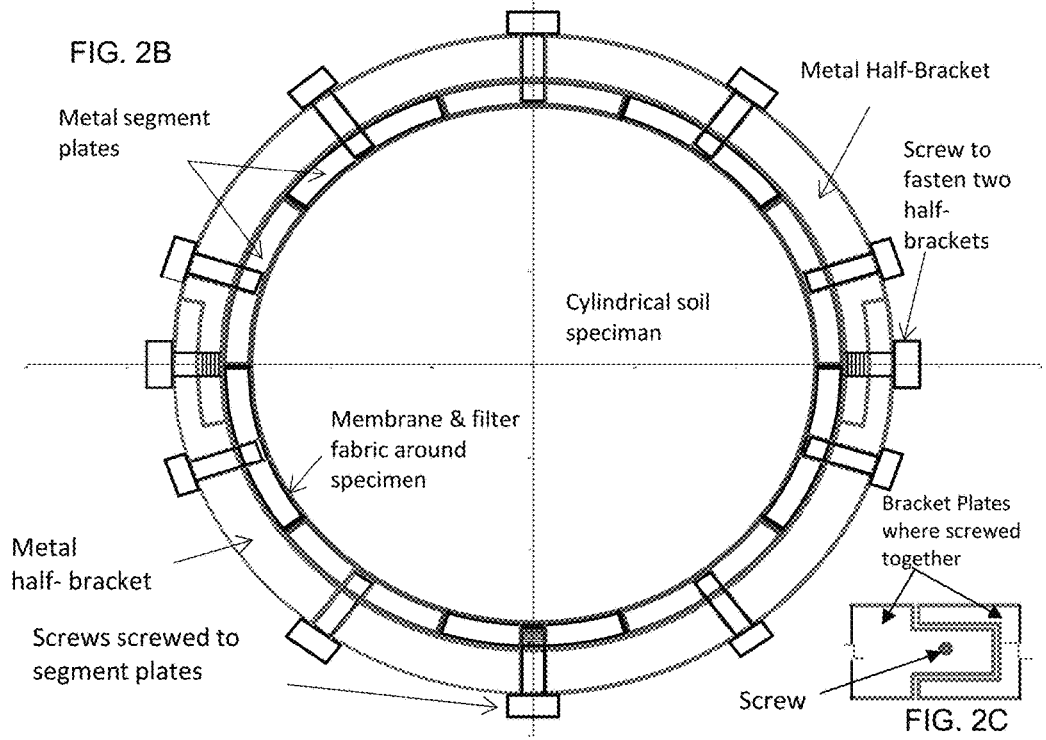

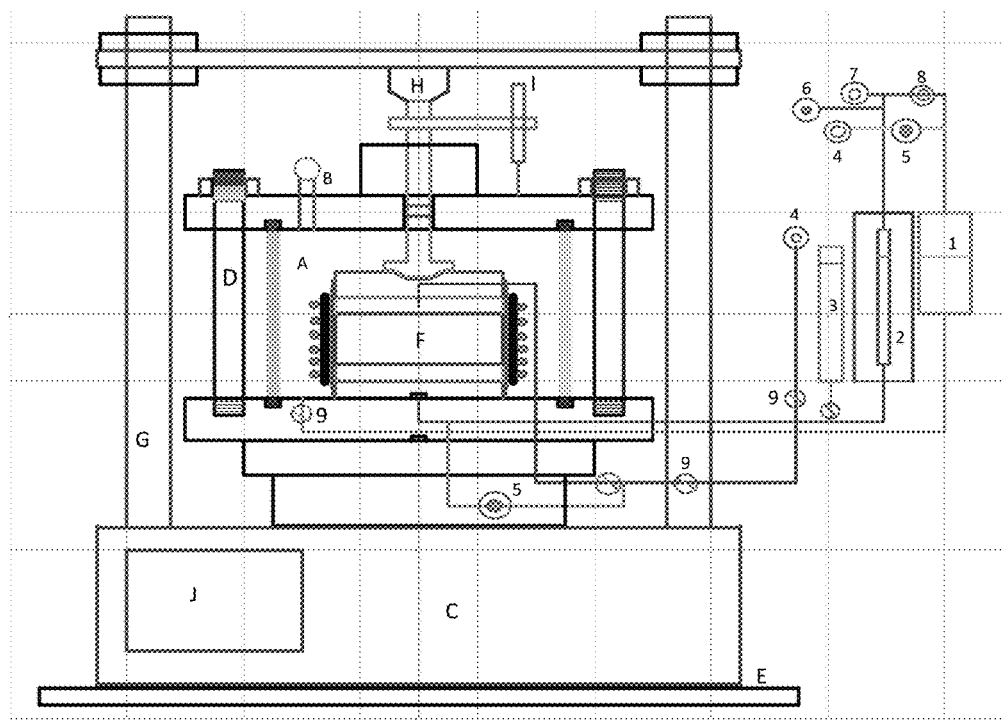

LEGEND

For Control Panel
1 Chamber Pressure Reservoir
2 Volume Change Burette
3 Water Reservoir
4 Vacuum Regulator
5 Differential Pressure Transducer
6 Back Pressure Transducer
7 Back Pressure Regulator
8 Cell Pressure Regulator (Differential)
9 Valves

For Chamber and Loading Device
A Acrylic Chamber/Cell
B Vent
C Axial Loading Device
D Clamping Rods for Chamber
E Table Top
F 3-D Consolidation Test Sample Assembly
G Loading Frame with Rods
H Load Cell (or Prooving Ring)
I Deformation Transducer (or Dial Gage)
J Regulator Board for Strain Rates

FIG. 19

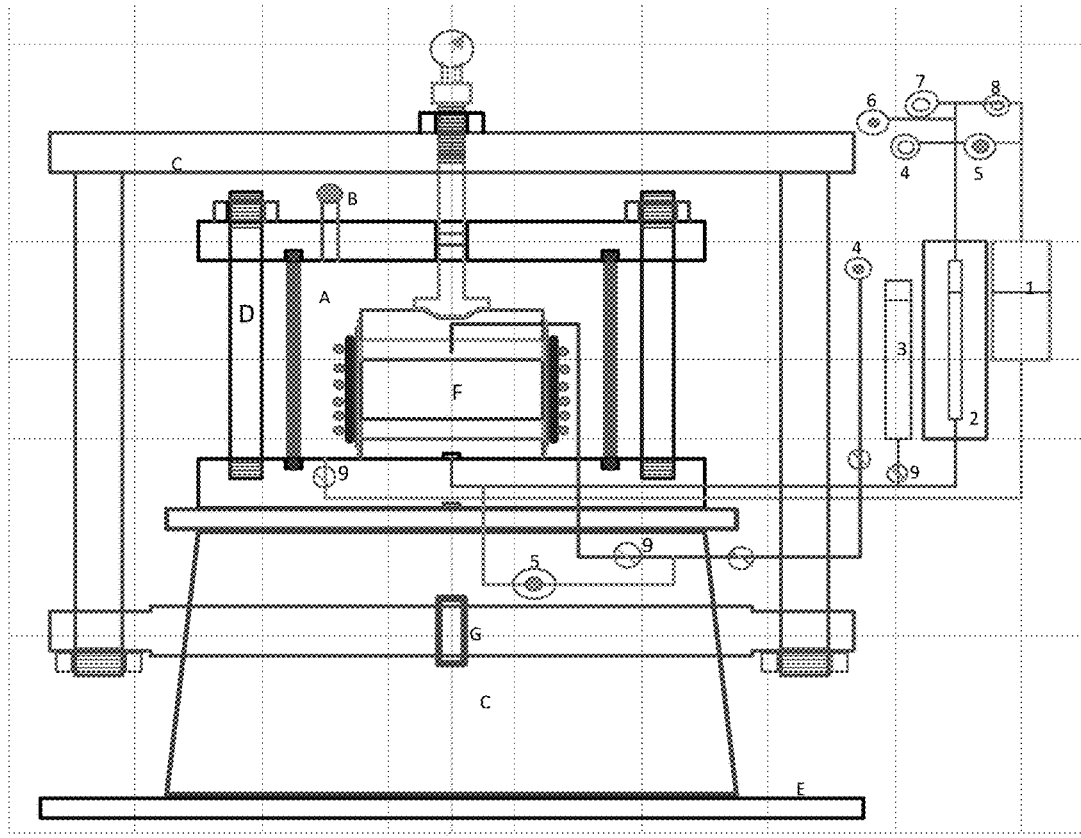

For Control Panel
1 Chamber Pressure Reservoir
2 Volume Change Burette
3 Water Reservoir
4 Vacuum Regulator
5 Differential Pressure Transducer
6 Back Pressure Transducer
7 Back Pressure Regulator
8 Cell Pressure Regulator (Differential)
9 Valves

LEGEND
For Chamber and Loading Device
A Acrylic Chamber/Cell
B Vent
C Incremental Loading Device/Frame
D Clamping Rods for Chamber
E Table Top
F 3-D Consolidation Test Sample Assembly
G Cantilever Loading Arm for weights

FIG. 20

EXPANDABLE JACKET FOR TRIAXIAL, UNCONFINED AND UNIAXIAL COMPRESSION TESTS AND TEST DEVICE FOR THREE-DIMENSIONAL CONSOLIDATION AND SETTLEMENT TESTS

CROSS REFERENCE TO RELATED APPLICATIONS

This specification is complete-in-itself.

STATEMENT OF FEDERALLY SPONSORED RESEARCH/DEVELOPMENT

This invention is not sponsored or supported by federally sponsored research or development. This invention has been developed by me, Dr. Ramesh Chandra Gupta, Ph. D., P.E, President and Sole Owner of SAR6 INC., solely at my own cost and time.

The Names of the Parties to a Joint Research Agreement if the Claimed Invention Was Made as a Result of Activities Within the Scope of a Joint Research Agreement There is no joint research agreement with anyone. As stated earlier, this research/invention was conceived and completed solely by me (Dr. Ramesh C. Gupta, the inventor). It is my individual research work for this invention.

Reference to a "Sequence Listing," a table, or Computer Program Listing Appendix Submitted on a Compacted Disc and Incorporation by Reference of the Material on Compact Disc. The Total Number of Compact Disc Including Duplicates and the Files on Each Compact Disc Shall be Specified List of figures and tables with figure and table captions has been included in Item 8. The whole package is submitted in PDF format attached to the email. A compact disc containing the whole package can be submitted on demand from Patent Office.

BACKGROUND OF THE INVENTION

It is claimed by the inventor (Dr. Ramesh Chandra Gupta, Ph. D., P.E.) that with the use of the expandable jacket around the soil specimen, a uniform increase in diameter of the cylindrical specimen of soils and intermediate geomaterials shall occur through its height without any localized bulging or formation of a barrel shape, permitting accurate calculation of new area of cross-section at any instant of time, when axial vertical load is applied during the triaxial compression test. New area of cross-section is required to calculate the deviator stress during the process of shearing at any instant of time. So far for more than 100 years, the criticism of triaxial test has been that during the test, barrel shape sometimes with localized bulging forms, resulting in premature failure of the specimen, inaccurate determination of the area of cross-section, the deviator stress, and affecting the accuracy of volume change characteristics.

The expandable jacket consists of the rubber membrane surrounding the cylindrical specimen, circular segmental metal plates surrounding the rubber membrane, and elastomeric rubber bands or rings around the segmental plates to permit uniform radial expansion and maintain uniform diameter of the specimen during the test and thereby providing accurate values of deviator stress, volume change characteristics and shear strength of soils and intermediate geomaterials. For the above purpose, the expandable jacket surrounding the cylindrical specimen of soils and intermediate geomaterials shall be used during triaxial compression tests. For the same purpose, to determine accurate value of the unconfined compressive strength without permitting the barrel shape to form, the expandable jacket surrounding the cylindrical specimen of the cohesive soils, soft and jointed or fissured rocks shall be used during the unconfined compression tests.

So far, because barrel shape always formed during these compression tests on soils and intermediate geomaterials, LVDT measurement of the radial expansion of the specimen was not being done, but now with invention of expandable jacket and flexible ring, the measurement of radial expansion by LVDT becomes an attractive item during the test. During triaxial compression, unconfined compression and uniaxial compressive strength tests, both vertical displacement and radial displacement/expansion occurs simultaneously and when LVDT is placed in contact with the surface of the cylindrical specimen for measuring the radial expansion of the specimen, LVDT probe in contact with the specimen gets bent or inclined due to the vertical displacement of the specimen, resulting in inaccurate readings and many times damaging the probe. To prevent this to happen, a spring-loaded U-frame resting on ball bearings has been invented to mount the LVDT probe in it. The U-frame can move horizontally with LVDT probe affording the measurement of radial expansion, while specimen vertically compress along lubricated face of the U-frame. The measurement of radial expansion by LVDT mounted in the U-frame shall permit determination of accurate values of Poisson's ratio. When, LVDT measurements are done in a pressure chamber or sealed reservoir, it is necessary to select a suitable LVDT which can withstand the fluid pressures without damage to the electronics in it and then it is necessary to provide a sealed exit for the cable of LVDT without creating leakage in the pressure chamber. Even in open reservoir a right selection of LVDT is required. A proper design for the sealed exit have to be made as provided in this application.

For more than 100 years, the coefficient of consolidation and dissipation of excess pore-water pressures have been determined only in vertical direction using one-dimensional consolidation tests. However, in the field, this very seldom or never happens, because settlement, consolidation and dissipation of excess pore-water pressures always occurs both in horizontal and vertical directions. To simulate true field behavior, three-dimensional consolidation test has been invented using a flexible ring which is like the expandable ring as far as most structural components are concerned, except that a filter fabric or paper is wrapped around the cylindrical specimen, and then rubber membrane is mounted surrounding the filter paper or paper. The presence of the fabric filter or filter paper surrounding the cylindrical specimen of soils and intermediate geomaterials shall allow dissipation of excess pore-pressures in horizontal direction and porous discs above and below the cylindrical specimen shall allow dissipation of excess pore-pressures in vertical direction; and the flexible ring shall permit uniform radial expansion of the specimen simultaneously with vertical displacement under vertical load, thus simulating field conditions.

For saturated soils, excess pore-water expelled out of the specimen during the test can be collected in burette of the control panel and help in determination of radial expansion and thereby calculation of Poisson's ratio for both during triaxial tests and three-dimensional consolidation tests, but for partially saturated soils, the radial expansion can be approximately calculated by using assumed values of Poisson' ratio as available in literature. For calculating accurate values of the radial expansion of the cylindrical specimen of the partially saturated soils and intermediate geomaterials and Poisson's ratio, measurement of the radial expansion by LVDT mounted in spring-loaded U-frame moving on ball bearings as invented with this application, is required to be done.

For calibration of expandable jacket and flexible ring and to determine modulus of elasticity of rubber membrane and combined modulus of elasticity of expandable jacket and flexible ring, a calibration device has been invented, which consist of a vertically movable water reservoir, a horizontal porous metal tube connected to movable water reservoir, via at least one tube, wherein porous metal tube is configured to be surrounded and sealed by an additional rubber membrane and wherein the additional rubber membrane is configured to be surrounded by a combination of the filter fabric or filter paper, the rubber membrane, the segmental metal plates, and the at least one elastomeric rubber band.

BRIEF SUMMARY OF THE INVENTION (I) Expandable Jacket

FIG. 1(a) shows the cylindrical shape of the soil specimen before beginning the triaxial compression test. FIG. 1(b) shows the barrel shape of the soil specimen with non-uniform lateral displacement during the triaxial compression test. To prevent barrel shape to form, the expandable jacket has been invented. With the use of the expandable jacket around the cylindrical specimen of soils and intermediate geomaterials, a uniform increase in diameter of the cylindrical specimen shall occur through its height without any localized bulging or formation of a barrel shape, permitting accurate calculation of the new area of cross-section at any instant of time, when axial vertical load is applied during the triaxial compression test. New area of cross-section is required to calculate the deviator stress during the process of shearing at any instant of time. So far for more than 100 years, the criticism of triaxial test has been that during the test, barrel shape sometimes with localized bulging forms, resulting in premature failure of the specimen, inaccurate determination of the area of cross-section, the deviator stress, and affecting the accuracy of volume change characteristics.

As shown in FIG. 4 and FIG. 5, the expandable jacket consists of the rubber membrane surrounding the cylindrical specimen, circular segmental metal plates surrounding the rubber membrane, and elastomeric rubber bands or rings around the segmental plates to permit uniform radial expansion and maintain uniform diameter of the specimen during the test and thereby providing accurate values of deviator stress, volume change characteristics and shear strength of soil and intermediate geomaterials. For the above purpose, the expandable jacket surrounding the cylindrical specimen of soils and intermediate geomaterials shall be used during triaxial compression tests. For the same purpose, to determine accurate value of the unconfined compressive strength without permitting the barrel shape to form, the expandable jacket surrounding the cylindrical specimen of the cohesive soils, soft and jointed or fissured rocks shall be used during the unconfined compression tests. FIG. 6A shows initial cylindrical shape of the shape, and FIG. 6B shows the uniform shape of the cylindrical specimen after undergoing radial expansion and vertical displacement simultaneously under the vertical load applied during the test.

For assembling the expandable jacket around the cylindrical specimen, removable attachments consisting of two brackets as shown in FIG. 2A and FIG. 2B are used. The segmental circular shaped plates are attached to each of the two half-brackets using screws to screwed in screw mounts with female (internal threads) in the brackets and segmental plates and wrapped around the rubber membrane surrounding the cylindrical specimen and the two-half-brackets are screwed together, after which the elastomeric rubber bands or rings are slipped around the segmental plates, as shown in FIG. 3. Additionally, leather or fabric hook and loop straps are used and segmental plates are screwed to gather with hook and loop straps, and then wrapped around the rubber membrane surrounding the cylindrical specimen, after which rubber bands or rings are installed around the circular segmental metal plates, as shown in FIG. 4. Thereafter, the two half-brackets or hook and loop straps are removed and additional rubber bands or rings installed around the segmental plates in the space previously covered by the brackets or hook and loop straps, as shown in FIG. 5. With these sequential steps, expandable jacket has been installed to proceed to further steps, such as placing the chamber around the flexible ring surrounding the cylindrical specimen, placing the top plate of the chamber, installing clamping rods, filling water or fluid in the chamber through the port in the bottom plate of the chamber, placing the loading head through the hole in the top plate of the chamber, other steps in proper sequence, all according to the standard methods of ASTM or other national and international organizations, to perform the triaxial compression tests.

For saturated soils, excess pore-water expelled out of the specimen during the test can be collected in burette of the control panel and help in determination of the radial expansion and thereby calculation of Poisson's ratio for both during triaxial tests and three-dimensional consolidation tests, but for partially saturated soils, the radial expansion can be approximately calculated by using assumed values of Poisson' ratio as available in the literature. For calculating accurate values of the radial expansion of the cylindrical specimen of the partially saturated soils and intermediate geomaterials and Poisson's ratio, measurement of the radial expansion by LVDT mounted in spring-loaded U-frame, moving on ball bearings as invented with this application, is required to be done.

In FIG. 7, high pressure sealed LVDT removably attached to a spring-loaded U-frame movable on ball bearings has been shown to measure radial expansion of the cylindrical specimen of soils and intermediate geomaterials during triaxial test. During triaxial compression test, the chamber can be pressurized by fluid pressure up to 150 psi or more for specialty testing. Therefore, the high pressure sealed LVDT is thread connected with O-rings in a metal tube weld connected to the metal cylindrical wall of the chamber, as shown in FIG. 7. In FIG. 8, the guided core LVDT has been mounted in spring-loaded U-frame to measure radial expansion of the cylindrical specimen of cohesive soils, soft or jointed rocks during unconfined compression test. The spring-loaded LVDT is also available in the industry, but it is not suitable to be used in a pressure chamber, but it can be used for unconfined compression tests with either spring-loaded U-frame or U-frame which is not spring-loaded. In FIG. 9, the LVDT is mounted on spring-loaded U-frame movable on ball bearings, to measure radial expansion of cylindrical specimen of concrete cores or intact rock cores; in case of concrete cores and intact rock cores, the expandable jacket is not required and therefore the face of the U-frame is in contact to the surface of the concrete or rock core, as shown in FIG. 9.

(II) Test Device to Determine Three-Dimensional Consolidation Properties

Test device consists of a flexible ring. The flexible ring and expandable jacket is very similar-to each other as most structural components of each are quite similar, except that the flexible ring is provided with fabric filter or paper filter which is wrapped around the cylindrical specimen of soils and intermediate geomaterials and then rubber membrane is installed surrounding the filter. The presence of the fabric filter or filter paper surrounding the cylindrical specimen shall allow dissipation of excess pore-pressures in horizontal direction and porous discs above and below the cylindrical specimen shall allow dissipation of excess pore-pressures in vertical direction; and the flexible ring shall permit uniform radial expansion of the specimen simultaneously with vertical displacement under vertical load, thus simulating field conditions.

As shown in FIG. 11A, the flexible ring consists of the filter fabric or filter paper around the cylindrical specimen, rubber membrane surrounding the fabric filter or filter paper, circular segmental metal plates surrounding the rubber membrane, and elastomeric rubber bands or rings around the segmental plates to permit uniform radial expansion and maintain uniform diameter of the specimen during the test. FIG. 10A shows the device for determining coefficient of consolidation in vertical direction while permitting both horizontal and vertical displacements to occur, in this case filter fabric or filter paper is not wrapped around the cylindrical specimen. FIG. 10B shows the device to determine the coefficient of consolidation in horizontal direction while permitting both horizontal and vertical displacements to occur; in this case, porous discs are not used and the cylindrical specimen is placed in between specimen base and top plates (with filter disc in between). FIG. 11A shows the device to determine three-dimensional coefficient of consolidation permitting dissipation of pore-pressures both in vertical and horizontal direction, while allowing both horizontal and vertical displacements to occur. In all these three cases, the test device is covered by open metal water reservoir. FIG. 11B, FIG. 12A, and FIG. 12B show the test device to determine three-dimensional coefficient of consolidation, coefficient of consolidation in horizontal direction and coefficient of consolidation in vertical direction, respectively, when the device is placed in a triaxial type chamber or in a sealed reservoir, properly sized based on the diameter and height of the cylindrical specimen. When LVDT measurements are done the diameter of the chamber, sealed reservoir and open reservoir shall also depend on the length of the body of LVDT.

FIG. 13A and FIG. 13B show the test device to determine the three-dimensional settlement characteristics of soils which do not generate excess pore-water pressures or the excess pore-water pressures dissipate as soon as they develop, such as cohesionless soils and cohesionless intermediate geomaterials; these devices do not require the filter fabric. The test device shown in FIG. 13A is covered by open metal water reservoir, while the test device shown in FIG. 13B is covered by a triaxial type chamber or sealed reservoir. Triaxial type chamber or sealed reservoir shall be sized based on the diameter and height of the cylindrical specimen for these tests. The height of the cylindrical specimen can range between minimum 0.5 inch (12.7 mm) and ¾th of the diameter of the cylindrical specimen. Minimum specimen diameter to height ratio shall be 2.5.

Removable attachments for assembling the flexible ring are the same as for the expandable jacket as shown in FIG. 2A, FIG. 2B, FIG. 14A, and FIG. 14B, which consist of two half-circular metal brackets, and leather or fabric hook and loop straps. After assembling the segmental metal plates in the two half-circular brackets, the two brackets are installed around the cylindrical specimen and then the two brackets are fastened together by screws as shown in FIG. 14A, and thereafter, the elastomeric rubber bans or rings are mounted surrounding the metal segmental plates. After assembling the segmental metal plates in the leather or fabric hook and loop straps, the straps are installed around the cylindrical specimen and, and thereafter, as shown in FIG. 14A, the elastomeric rubber bans or rings are mounted surrounding the metal segmental plates. The additional rubber bands or rings are mounted in the space earlier covered by the brackets and straps as shown in FIG. 15A.

FIG. 16A shows schematic detail of open reservoir made of acrylic or metal cylindrical wall and bottom plate; wherein the wall and bottom plate are connected using threads and a O-Ring for water tightness. FIG. 16B shows a sealed metal reservoir of which metal top plate and bottom plate is provided with valves, drainage and filling ports etc. in the same way as are provided in the bottom and top plates of a triaxial type chamber. After assembling the flexible ring around the cylindrical specimen, the flexible ring is covered either by the open water reservoir or triaxial type chamber as shown in FIG. 15B, FIG. 17, FIG. 18, FIG. 19 and FIG. 20. For saturated soils, excess pore-water expelled out of the specimen during the test can be collected in burette of the control panel and help in determination of the radial expansion and thereby calculation of Poisson's ratio for both during triaxial tests and three-dimensional consolidation tests, but for partially saturated soils, the radial expansion can be approximately calculated by using assumed values of Poisson' ratio as available in the literature. For calculating accurate values of the radial expansion of the cylindrical specimen of the partially saturated soils and intermediate geomaterials and Poisson's ratio, measurement of the radial expansion by LVDT mounted in spring-loaded U-frame, moving on ball bearings as invented with this application, is required to be done.

FIG. 16C shows a sealed metal reservoir, with metal tube weld connected to the metal cylindrical wall. The metal tube is provided with female (internal) threads matching the male (external) threads of the high pressure sealed LVDT. In FIG. 17, high pressure sealed LVDT removably attached to a spring-loaded U-frame movable on ball bearings has been shown to measure radial expansion of the cylindrical specimen of soils and intermediate geomaterials during three-dimensional consolidation test. During three-dimensional consolidation test, the chamber can be pressurized by fluid pressure up to 150 psi or more for specialty testing. Therefore, the high pressure sealed LVDT is thread connected with O-rings in a metal tube weld connected to the metal cylindrical wall of the chamber, as shown in FIG. 17. FIG. 18 shows a hermetically sealed (i.e. high pressure sealed) LVDT with radial connector with double sealed cable exit and sealed pressure chamber connector for cable exit from top plate of the chamber.

FIG. 19 shows a triaxial type chamber covering the flexible ring containing cylindrical specimen, triaxial type loading frame and the axial loading device, screw driven by an electric motor through geared transmission to provide the suitable rate of axial strain. FIG. 20 shows a triaxial type chamber covering the flexible ring containing cylindrical specimen, incremental loading frame (same as is used for one-dimensional consolidation test) and the axial loading device, screw driven by an electric motor through geared transmission to provide the suitable rate of axial strain.

(III) Calibration Device

For calibration of expandable jacket and flexible ring and to determine modulus of elasticity of rubber membrane and combined modulus of elasticity of expandable jacket and flexible ring, a calibration device has been invented, which consist of a vertically movable water reservoir, a horizontal porous metal tube connected to movable water reservoir, via at least one tube, wherein porous metal tube is configured to be surrounded and sealed by an additional rubber membrane and wherein the additional rubber membrane is configured to be surrounded by a combination of the filter fabric or filter paper, the rubber membrane, the segmental metal plates, and the at least one elastomeric rubber band.

FIG. 21 shows the calibration device, before expandable jacket or flexible ring is installed around it; for determination of modulus of elasticity of rubber membrane; the calibration is performed by raising the movable water reservoir each time by half a foot (0.15 m) or less, the head of the water reservoir over the center of porous metal tube and the change in the water level in reservoir helps in determining the radial pressure and radial strain experienced by the rubber membrane and thereby the modulus of elasticity.

FIG. 22 shows the calibration device when the expandable jacket or flexible ring has been installed around it; the calibration is performed by raising the movable water reservoir each time by half a foot (0.15 m) or less, the head of the water reservoir over the center of porous metal tube and the change in the water level in reservoir helps in determining the radial pressure and radial strain experienced by the rubber membrane, and flexible or expandable jacket and thereby helps in determining the combined modulus of elasticity of the rubber membrane, fabric filter or filter paper (only for flexible ring and not for expandable jacket), another rubber membrane, segmental metal circular arch shaped metal plates and rubber bands and rings.

BRIEF DESCRIPTION OF THE SEVERAL VIEWS OF THE DRAWINGS

FIG. 2A and FIG. 2B describe the plan view of the segment circular stainless steel plates assembled in position with the help of two half-circular brackets.

FIG. 19 shows the triaxial type chamber, triaxial type loading frame, axial load device, triaxial type chamber control panel and the flexible ring containing cylindrical specimen of soils or intermediate geomaterials.

FIG. 20 shows the triaxial type chamber, incremental load device, triaxial type control panel and the flexible ring containing cylindrical specimen of soils or intermediate geomaterials.

DETAILED DESCRIPTION OF THE INVENTION

Figure 1A:
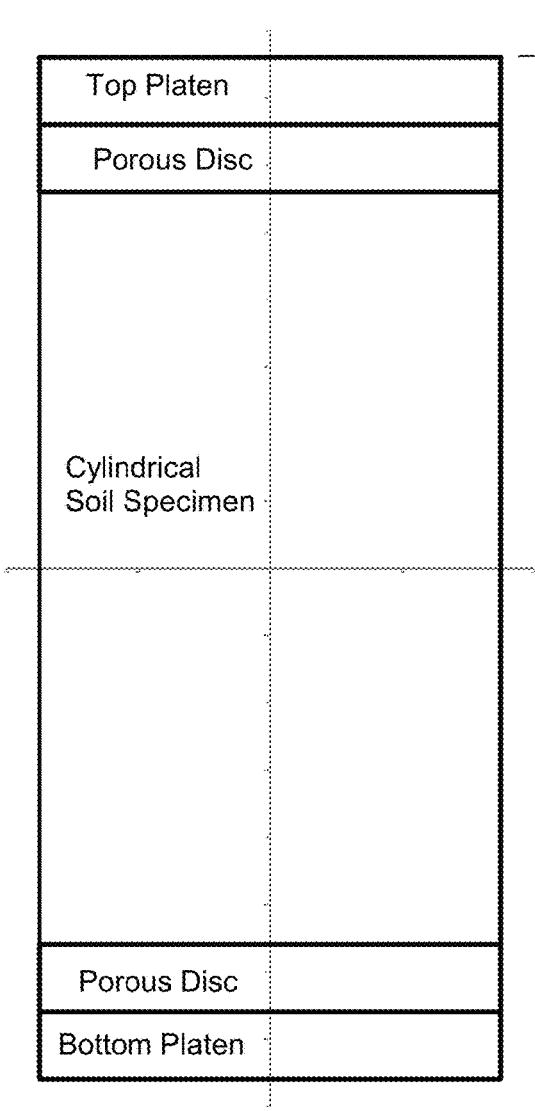
FIG. 1(a) describes the initial shape of the cylindrical soil specimen before beginning of the triaxial compression test.

The expandable jacket with height greater than its diameter (generally about two times the height of its diameter) has been invented to be placed surrounding the specimen of soils, and intermediate geomaterials during triaxial compression tests, unconfined compression tests for cohesive soils, soft and jointed rocks. Spring loaded U-frame resting on ball bearings has been invented to mount the LVDTs to measure uniform radial expansion of the cylindrical specimen during triaxial compression tests, unconfined compression tests and uniaxial compressive tests on intact rock cores and concrete cores.

The test device to determine three-dimensional consolidation and settlement properties of soils and intermediate geomaterials, uses a flexible ring in place of a fixed ring. The flexible ring shall be used when the height of the cylindrical specimen is less than its diameter. The flexible ring and expandable jacket are very similar-to each as all structural components and removable attachments for assembling the expandable jacket and the flexible ring are the same. Spring loaded U-frame with LVDTs shall also be used with both expandable jacket and flexible ring, when required to measure uniform radial expansion for determination of the volume change characteristics, lateral resistance provided by the flexible ring on the cylindrical specimen and Poisson's ratio. Because of similarities between the expandable jacket and the flexible ring, both expandable jacket for triaxial, unconfined and uniaxial compression tests and test device, which uses flexible ring, for three-dimensional consolidation and settlement tests, have been included in this application.

Geomaterials are defined as cohesion-less soils, cohesive soils, cohesionless intermediate geomaterials, cohesive intermediate geomaterials, and rocks. Cohesionless soils have $N_{60}$-values less than 50 blows/ft (0.3 m), [standard penetration resistance defined by $N_{60}$, N is defined as number of blows/ft (0.3 m) and N60 is defined as N-values when related to 60% efficiency]. Cohesive soils are defined as having undrained shear strength ($s_u$) less than 0.25 $MN/m^2$. Cohesionless intermediate geomaterials are defined as having $N_{60}$ values greater than 50 blows/ft (0.3 m). Cohesive intermediate geomaterials are defined as having undrained shear strength greater than 0.25 $MN/m^2$, but less than 2.5 $MN/m^2$. Rocks are defined as having undrained shear strength equal or greater than 2.5 $MN/m^2$ and uniaxial strength equal or greater than 5 $MN/m^2$.

In this application being filed by me as an applicant and sole inventor, several important items, as explained in the detailed description, have been made and added, when compared with my own patents as sole inventor, in U.S. Pat. No. 9,383,346 B2 filed on Mar. 17, 2015, U.S. Pat. No. 9,567,722 B2 filed on Jun. 3, 2015, U.S. Pat. No. 9,546,940 B2 filed on Jun. 1, 2016.

Detailed description of the invention has been described in two parts; Part 1 for expandable Jacket and Part II for the test device using flexible ring for three-dimensional consolidation and settlement tests:

(I) Expandable Jacket (a) Test Methods for Triaxial Compression Tests

The standard test methods for unconsolidated-undrained triaxial (UU) compression test and consolidated undrained (CU) triaxial compression test for cohesive soils are described in ASTM Designation: D2850-03a (reapproved 2007) and ASTM Designation: D476-11, respectively. International and national organizations of several countries have their own standards. UU tests are performed to determine strength and stress-strain relationships of a cylindrical specimen of either undisturbed or remolded cohesive soil. Specimens are subjected to a confining fluid pressure in a triaxial chamber. No drainage of the specimen is permitted during the test. The specimen is sheared in compression without drainage at a constant rate of axial deformation (strain controlled). CU tests are performed to determine strength and stress-strain relationships of a cylindrical specimen of either an intact, reconstituted, or remolded or saturated cohesive soil. Specimen are isotropically consolidated and sheared in compression without drainage at a constant rate of axial deformation (strain controlled). Triaxial compression tests on cohesionless soils are similarly performed either on dry or partially saturated or fully saturated cylindrical specimen generally with drainage permitted. The specimen is sheared in compression at a constant rate of axial deformation (strain controlled). Unconfined compressive strength tests are performed on intact, remolded, or reconstituted samples of cohesive soils in accordance with ASTM D2166 and AASHTO T208. Standard test methods for compressive strength and elastic moduli of intact rock core specimens under varying states of stress and temperatures are performed in accordance with ASTM D7012.

(b) Existing Research

One of the main criticisms of triaxial test is the non-uniformity of stress and deformation at all but very small strains (Rowe and Barden, 1964). The main cause of this uniformity is the friction at the end platens, which causes both the barreling effect and the concentration of dilation in local zones, which results in premature development of a failure surface. These disadvantages to some extent are largely overcome the use of lubricated end platens, which by removing the dead zones, allow the use of short samples (Rowe and Barden, 1964). Other causes are insufficient drainage, inherent non-uniformity of soil sample through its height, membrane effects and self-weight (Sheng et. al.

1997). Question arises; how much effect does such non-uniformity have on strength, stress strain characteristics, and volume change characteristics determined from a triaxial test. Different researchers have reached different conclusions (Lee, 1978). The experimental results indicate that (i) comparison between lubricated and non-lubricated ends, shows that the end friction had little influence on measured internal friction of sand samples (Bishop and Green, 1965), (ii) the end restraint has a significant influence on undrained shear strength of sand, but slight effects on drained strength and on the internal friction angle (Lee, 1978), and (iii) the undrained strength of a dense sand tested with lubricated ends was 20% greater than that with regular ends. Saada and Townsend (1981) summarized theoretical elastic solutions of stress distributions at end platens, and found that the vertical stress at the ends of specimen decreases from a very high concentration at the edge to a lower value at the center, and there are no unique patterns for distributions of radial, circumferential and shear stresses at the ends.

(c) Cross-sectional Area for a Given Load

Rubber membrane is used to encase the specimen to provide reliable protection against leakage and for separation between soil specimen and the chamber fluid. The membrane provides insignificant restraint to the specimen. The membrane is sealed to the specimen cap and base with rubber O-rings. The magnitude of fluid pressure in the chamber is selected based on the insitu horizontal pressure that may exist at a selected depth for which test is being performed to determine strength, stress-strain relationship and volume change characteristics. The fluid pressure cannot restrain the cylindrical soil specimen to maintain the uniform diameter through its height during shear, due to (1) end restraint imposed by the specimen end platens and (2) inherent non-uniformity in soil. With the result that soil specimen deforms laterally, but non-uniformly as shown in FIG. 1(b). The cross-sectional area, A, for a given applied load, is based on the assumption that the specimen deforms as a right circular cylinder with constant diameter during shear (Rochelle et al., 1988). With this assumption, A for a given applied load at an instant of time t, is given by:

$$A = \frac{A_c}{(1 - \varepsilon_v)} \quad (1)$$

Where: $A_c$=Average cross-sectional area of the specimen after consolidation and before beginning the test: $\varepsilon_v$=Axial strain for the given axial load at any instant time t=$\Delta H/H$; $\Delta H$=Change in height of specimen during loading; H=height of specimen after consolidation; D=Diameter of specimen after consolidation.

When the specimen may fail, or deform by bulging with no apparent shear plane, it is generally agreed that cross-sectional area, A, is given by:

$$A = A_c \frac{1 + \frac{\Delta V}{V}}{1 - \varepsilon_v} \quad (2)$$

It may be noted that the cross-sectional area which may govern the value of deviator stress may be controlled by the area at a height where the shearing is more intense and where slip plane may form and not necessarily by an average value, A, calculated by Eqs. 1 and 2. Non-uniform stress conditions within the test specimen are imposed by the specimen end platens. This can also cause redistribution of void ratio within the specimen causing non-uniformity in the soil specimen during the test. In these conditions, it remains unknown as to what could have been the volume change characteristics (such as decrease in volume or increase in volume known as dilation) of the soil specimen at any time during the shear or at the failure or at the peak strength, had non-uniform lateral displacement and non-uniform stress conditions not taken place, i.e. uniform lateral displacement had occurred through its height. The non-uniform lateral displacement is generally attributed to end area effect imposed by the specimen end platens, and in addition, due to the fluid pressure in chamber which cannot restrain or provide enough lateral stiffness to the specimen to maintain the same diameter of the specimen through its height. In the above-mentioned conditions, the specimen, which was cylindrical in shape in the beginning of the test, becomes barrel shape during the process of shearing.

(d) An Expandable Jacket and its Installation Surrounding a Cylindrical Specimen The expandable jacket has been designed to expand uniformly through its height, which thereby allows only uniform lateral displacement of the specimen during the triaxial compression test. The expandable jacket shall not permit the cylindrical specimen to develop a barrel shape or develop localized bulging during the test. Even if there is some or little inherent non-uniformity of void ratio in the real soil specimen, the expandable jacket will maintain its uniform diameter. In insitu stress conditions, uniform lateral stiffness or confinement is provided to a soil element by the soil around it and so, when the soil element is axially loaded, it experiences vertical displacement along with uniform lateral displacement. The uniform lateral resistance in insitu conditions does not allow non-uniform lateral displacement to occur. This type of confinement is not provided by the fluid pressure in a triaxial chamber. It may be noted that the end effects at top and bottom porous discs and end platens, creates the non-uniform lateral displacement which cannot be prevented by the fluid pressure.

The expandable jacket surrounding soil specimen of the intact, remolded, or reconstituted cohesive soil and soft or jointed rock shall also be useful for maintaining uniform radial expansion of the specimen. Spherical and cavity expansion theories have been applied to analyze the cone penetration problems and pile tip load at failure with the assumption that the cone penetration or pile tip penetration simulates cylindrical or spherical cavity expansion in soil (Vesic, 1972, Gupta, 2002a and 2002b). The triaxial compression test with expandable jacket around the soil specimen shall impose the same conditions as are expected to occur in soils insitu, when the cone penetration or progressive pile penetration occurs with the increase in load.

Figure 1B:
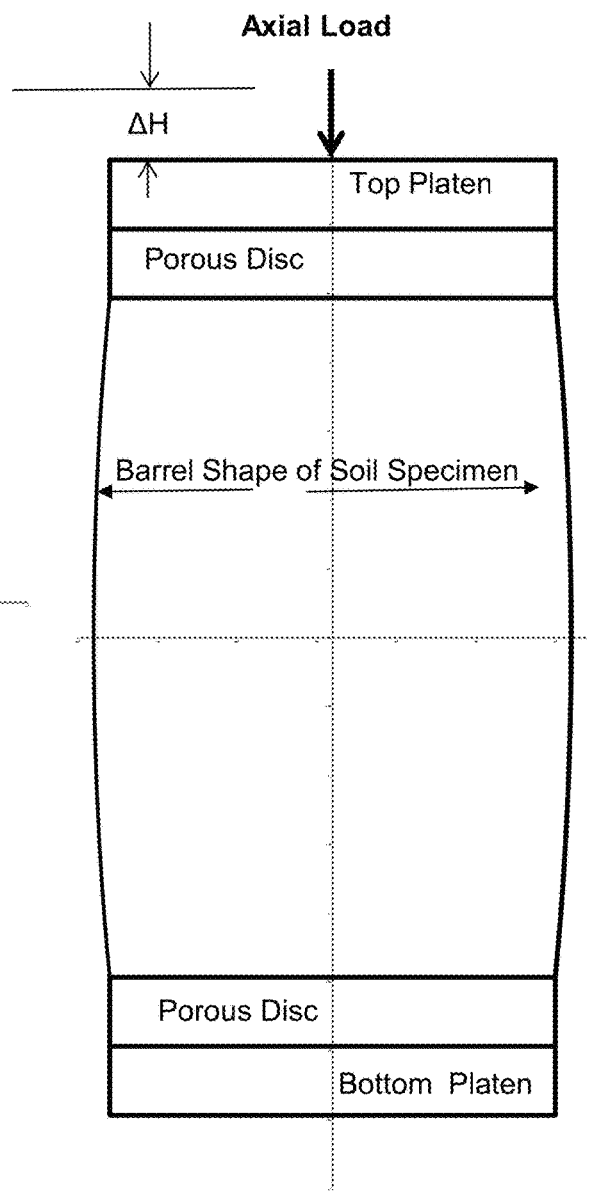
FIG. 1(b) describes the barrel shape of the same specimen with non-uniform lateral displacement during the triaxial compression test, which always develops when expandable jacket is not used.

FIG. 1A shows the initial cylindrical shape of the soil specimen with the uniform diameter through its height before the beginning of the triaxial compression test, i.e., before consolidation. FIG. 1B shows that non-uniform lateral displacement of specimen occurs progressively during the test and forms a barrel shape (sometimes even with localized bulging). The main objective of this invention is to prevent non-uniform displacement or localized bulging by use of an expandable jacket, which has been designed to maintain uniform lateral displacement of the soil specimen through its height during the test.

Figure 3:
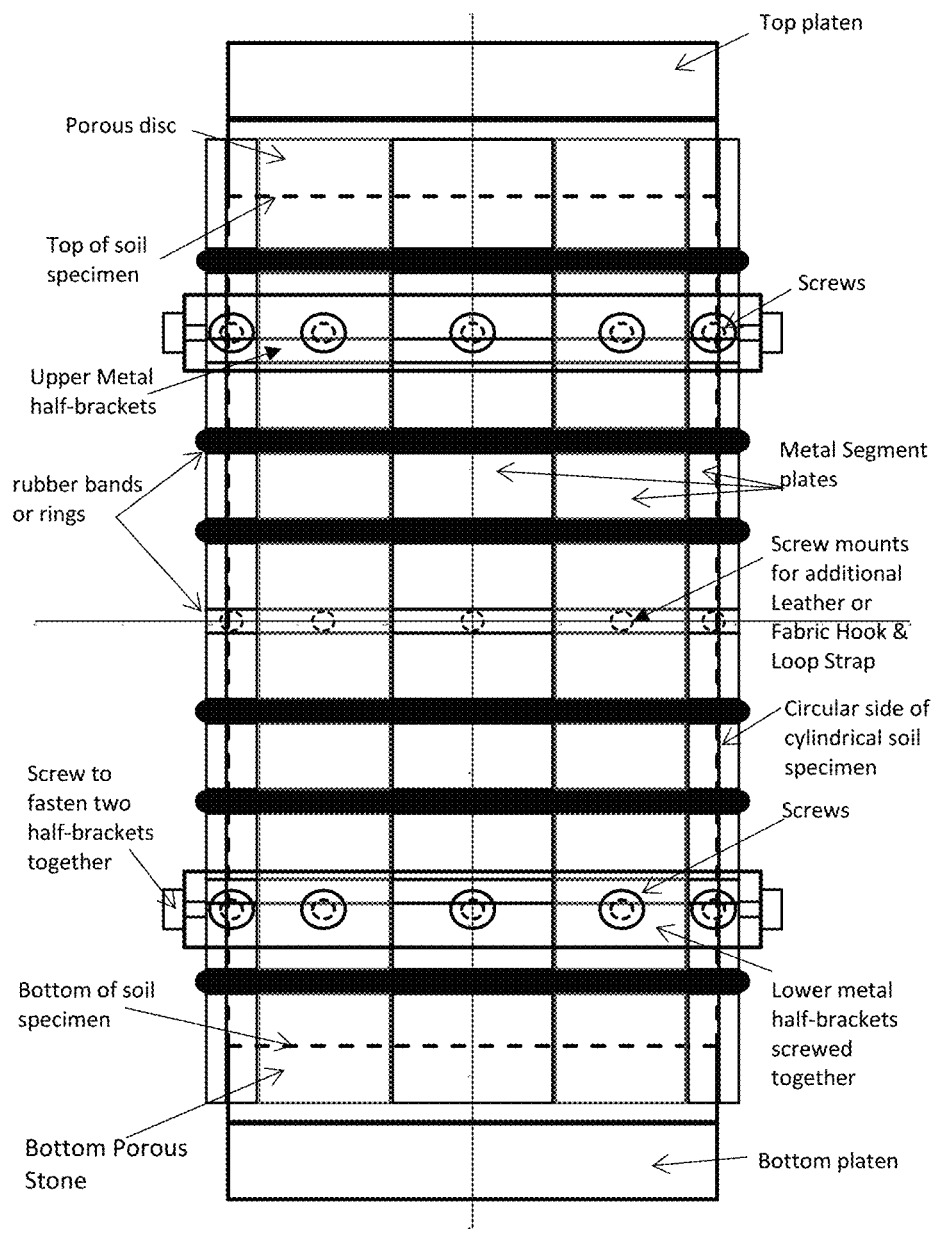
FIG. 3 describes the elevation of view of the segment circular stainless steel plates assembled in position with the help of two half-brackets, and after installation of brackets, the elastomeric rubber bands or rings have been installed.
Figure 4:
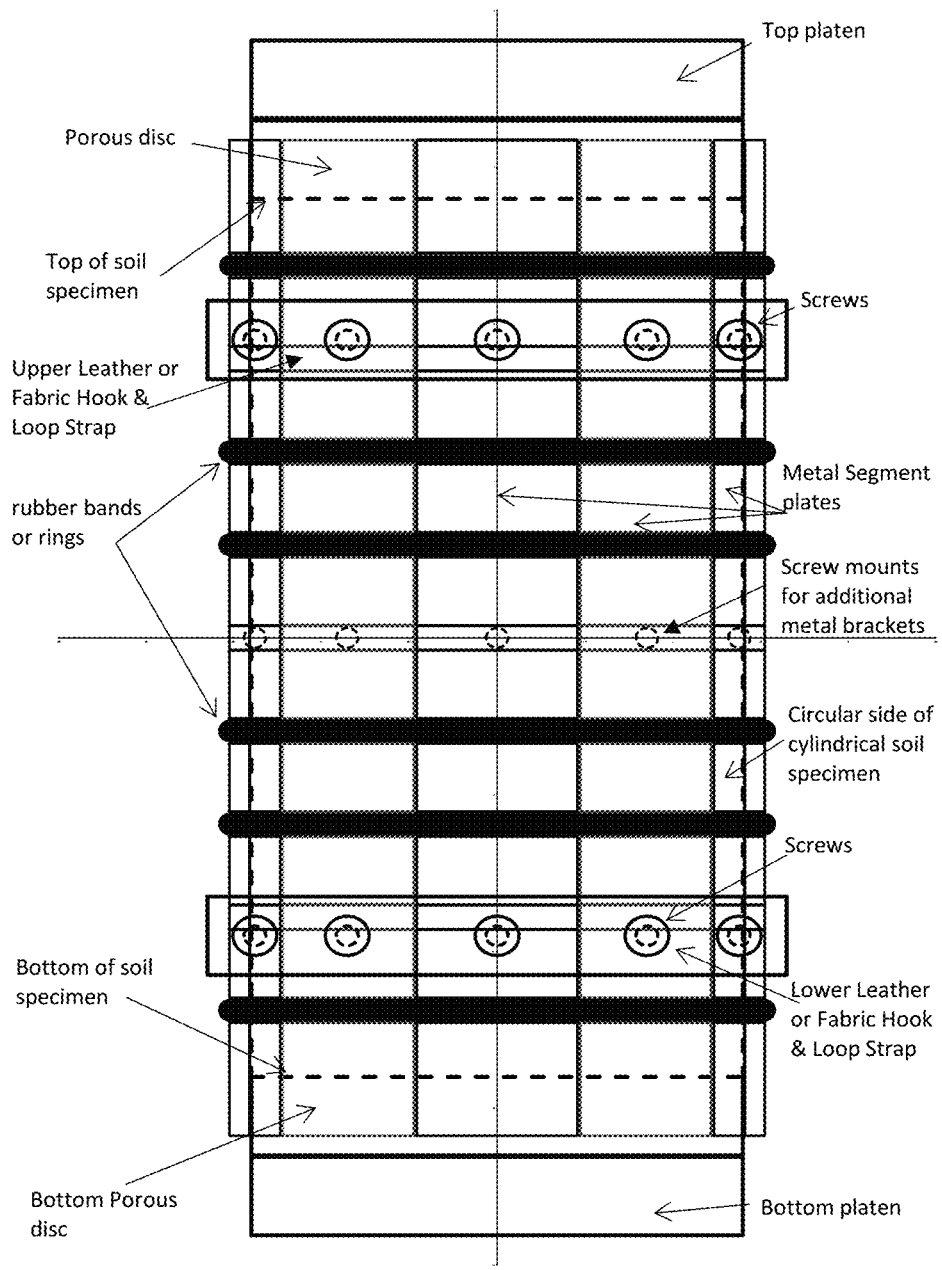
FIG. 4 describes the elevation of view of the segment circular stainless steel plates assembled in position with the help of leather or fabric hook and loop straps, and after installation of straps, the elastomeric rubber bands or rings have been installed.
Figure 5:
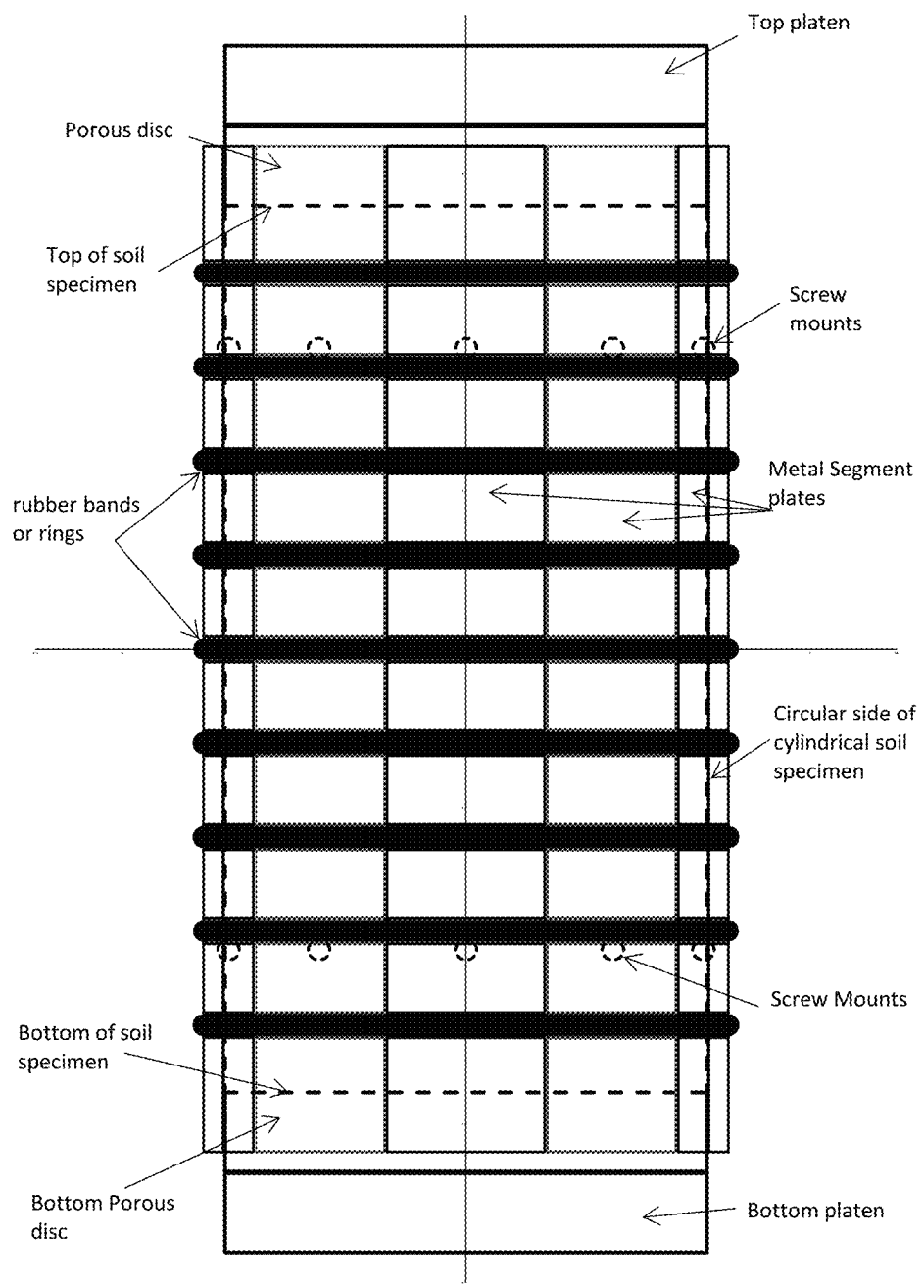
FIG. 5 shows that after the removable attachments of half-circular brackets or leather or fabric hoop and loop straps have been uninstalled, the rubber bands or rings are installed in the space previously occupied by the removable attachments.

The expandable jacket consists of metal segment plates, circular shaped arch in shape as shown in FIG. 2A and FIG. 2B. The thickness of plates may vary generally between about 1/16" and 3/8" (1.58 mm and 9.53 mm) or greater in thickness. Thicker segmental will not bend under the force exerted by the rubber bands or rings and in this respect, may have some advantage over thinner plates. These plates have screw mounts with female threads at selected predetermined heights generally some distance below the top of the plates and some distance above the bottom of the plates and at the mid-height of the plates or as needed. Screw sizes generally could vary US Machine screw sizes between # 4 and #14 or their approximately equivalent metric sizes. The metal segmental plates and metal brackets shall have internal (female) threads, while screws will have same and matching diameter and thread size as in the plates and brackets. These plates are installed around the rubber membrane which surrounds the specimen, using two-half circular metal brackets as shown in FIG. 2A, FIG. 2B and FIG. 3. The thickness of these brackets can generally vary between about ⅟₁₆" and ⅜" (1.58 mm and 9.53 mm), or greater. Rubber bands or rubber rings are slipped on around the plates as shown in FIG. 3 and FIG. 4. The width of rubber bands or rings, if of rectangular shape, can vary generally between ⅟₁₆" and ⅜" (1.58 mm and 9.53 mm), or greater. The thickness of rubber bands can vary generally between about ⅟₁₆" and ⅜" (1.58 mm and 9.53 mm) or greater. The diameter of rubber bands or rings, if of circular shape, can vary generally between ⅟₁₆" and ⅜" (1.58 mm and 9.53 mm), or greater. After installation of the bands or rings around the circular shaped segmental plates, the upper and lower brackets are un-installed. Remaining rubber bands or rings are slipped on around the plates in the space earlier covered by the brackets, as shown in FIG. 5. The expandable jacket has thus been installed around the soil specimen. If necessary, an additional removable bracket can be installed at the mid-height or at other heights as needed for proper installation.

Since the segmental circular arch shaped plates are resting against the top and bottom porous discs, initially the lateral load exerted by the rubber bands acts on the porous discs and very little, if any, directly on the soil specimen in the beginning of the test. When specimen begins to undergo lateral displacement or lateral expansion under the vertical load applied on the specimen during test, the rubber bands around the segmental plates shall stretch and exert pressure on the segmental plates thereby on the surface of the soil specimen all along its height and shall help in maintaining the uniform diameter through its height during the test, the plates are then not in contact with the porous discs and so the rubber bands or rings exert lateral pressure on the specimen. As many rubber bands as needed to maintain uniform diameter of cylindrical specimen, shall be used. However, the strength and number of rubber bands should be selected in such a manner that the increase in lateral resistance is approximately equal to the increase in the calculated lateral pressure that will occur when the soil undergoes expansion of cavity or lateral displacement due to the application of load at the depth for which test is being conducted. The lateral fluid pressure in the chamber should be approximately equal to the insitu earth pressure. The inside surface of the segment plates shall be lubricated to reduce the friction between the rubber membrane surrounding the soil specimen and the plates. The function of segmental metal plates is to uniformly distribute the lateral load applied by rubber bands on the soil specimen.

Additionally, the lubricated segment plates can be assembled surrounding the soil specimen by use of at least one (or generally two or more), leather or fabric hook and loop straps, generally about ½ to 1" (12.5 to 25.4 mm) wide or greater. First, segment plates are fastened to Hook and loop strap/straps, using appropriate size screws (matching the internal (female) threads, (screw sizes along with appropriate female threads in segment plates shall be selected based on workability and what is available in the industry). Then the assembled plates are wrapped around the soil specimen and maintained in position by hook and loop straps, the rubber bands or rings are slipped on around the plates as shown. After which, the screws are unthreaded to remove the straps. The remaining rubber bands are then slipped on around the plates in the space earlier occupied by the Hook and loop straps. The expandable jacket has now been installed around the soil specimen. The other steps such as placing the chamber around the expandable jacket, filling the chamber with water and installing loading device on top platen, applying fluid pressure in the chamber etc. are followed as per ASTM standards or other national or national organization's standards to perform the triaxial compression test.

Sizes and number of segment plates, half brackets and rubber bands shown in FIG. 2 through FIG. 5 and described in the text above are based on the cylindrical specimen diameter of 2.8" (71 mm) in diameter. Diameter of soil specimen generally used, are between 2.8" (71 mm) and 4" (100 mm). Diameter of soil specimen is also dependent on the inside diameter of Shelby tubes. Inside diameter of Shelby tubes as per ASTM standards are 1.905" (48.42 mm), 2.87" (72.9 mm) and 4.76" (120.9 mm). The diameter of the cylindrical specimen is also selected based on the local practice or based on standards of international organizations or national organizations of each Country/Nation. The diameter of circular arch shaped segment plates, two half-circular brackets and fabric hook and loop straps shall depend on the selected diameter of the soil specimen. Number of segment plates shall be generally about 8, 10 and 16 for soil specimen of 1.905" (48.42 mm), 2.87" (72.9 mm) and 4.76" (120.9 mm), respectively. For other specimen sizes, special design detail shall be used. Number of segmented metal plates selected shall also depend up on the width of the bracket or fabric strap, and diameter of the cylindrical specimen.

Figures 6A, 6B:
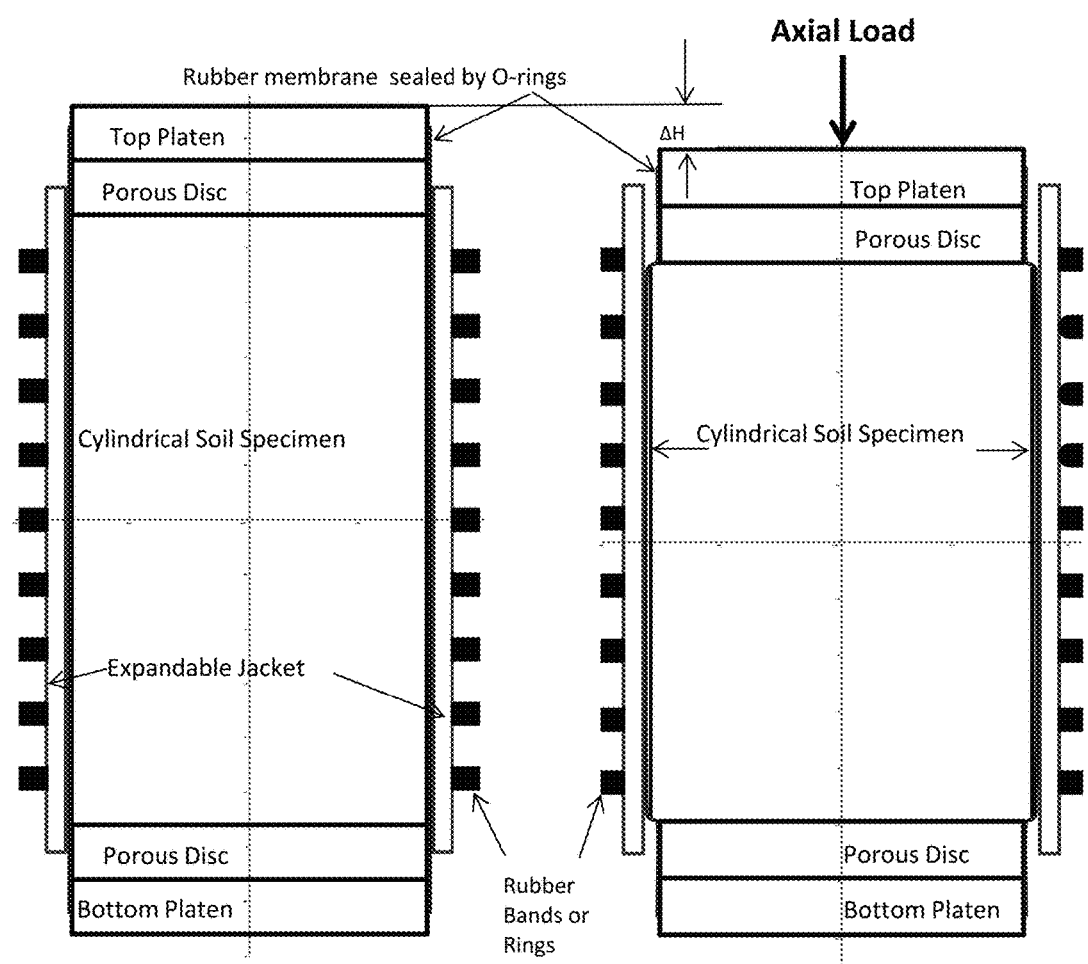
FIG. 6 shows that because of the expandable device, the cylindrical specimen of soils or intermediate geomaterials undergoes uniform lateral displacement or radial expansion with cylindrical shape during the triaxial compression test.

As described above, the expandable jacket shall maintain cylindrical shape of the soil specimen and its diameter shall remain uniform through its height during the test as shown in FIG. 6. Near the bottom and top porous disc, the diameter of specimen shall transition from diameter of porous disc to the expanded diameter of the specimen as shown in FIG. 6. Height of the transition shall be expected to be about two times of the increase in radius of soil specimen as load distribution occurs at 1H:2V in accordance with accepted theories. When calculations for the height of transition is done, it shall be found that the height of transition is very small and may vary between 0.042" (1 mm) to 0.14" (3.6 mm) for axial strains between 1 and 10%. Through remaining height of the soil specimen, the expandable jacket shall succeed in maintaining cylindrical shape with uniform diameter.

The lateral stress exerted by the rubber membrane and rubber bands around the cylindrical soil specimen for various values of axial strain is also calculated in Tables 1 and 2. The lateral stress exerted by the rubber bands and membrane shall be a product of lateral strain and modulus of elasticity of rubber. As shown in Table 1, the lateral stress, exerted by the rubber membrane and rubber bands on the soil specimen, varies from 0.3 psi at 1% axial strain to 4.5 psi at 15% axial strain for sand specimen with Poisson's ratio of 0.3. As shown in Table 2, the lateral stress exerted by the rubber membrane and rubber bands varies from 0.5 psi at 1% axial strain to 7.5 psi at 15% axial strain for saturated clay specimen with Poisson's ratio of 0.5. These calculations are based on the assumed value of E of rubber equal to 100 psi. Expandable jacket helps to maintain cylindrical shape with uniform diameter but also helps to quantify the lateral stress exerted by the rubber bands and membrane accurately. Note: 1 psi=6.894757 kN/m$^2$, 1"=25.4 mm, 1 foot=0.3048 m.

The lateral radial expansion of the 100% saturated soil specimen can be calculated based on the pore water expelled out from the specimen during the test and measured in the burette located in the control panel of the triaxial test equipment and the change in the height of the specimen. It is a standard practice to saturate the partially saturated specimen by applying varying increasing values of back-pressure. Therefore for 100% saturated soils, the uniform radial expansion of the cylindrical specimen and lateral resistance offered by the elastomeric rubber bands or rings during the test, can be calculated by pore-water expelled out from the specimen and measured in the burette along with measured change in height of the specimen, and it is then not necessary to measure the radial expansion by LVDTs.

When it is necessary to test the dry or partially saturated specimen, the radial expansion of the soil specimen can be approximately calculated based on the value of Poisson's ratio for various types of soil as available in the publications or guidelines and vertical displacement measured during the test or explained below. Poisson's ratio is the ratio of radial strain with vertical strain of the cylindrical specimen. Radial strain is equal to the ratio of change in diameter divided by the diameter. Vertical strain is the ratio of change in height divided by its height. The lateral stress exerted by the rubber membrane, rubber bands or rings shall be equal to the product of lateral strain with the modulus of elasticity of rubber. Even more accurate values of Poisson's ratio shall be available after tests using the expandable jacket has been performed and published. However, LVDTs to measure the radial expansion during the tests on dry or partially saturated soils may be more accurate instead of calculating approximately based on Poisson's ratio. When tests are being done to determine Poisson's ratio of dry or partially saturated soils, the use of LVDTs shall be preferable.

It may be noted that in all these tests, a filter disc (usually a filter paper disc is used, although machine woven thin filter disc can be used) is placed in between bottom of the cylindrical specimen and the bottom porous disc and between top of the specimen and the bottom of top porous disc, and in between the top of the specimen and the top porous stone, to avoid clogging of porous discs. Machine woven thin fabric filter disc can also be used in place of filter paper disc. These triaxial compression tests using expandable jacket shall be performed on the cylindrical specimen of the soils and intermediate geomaterials, using procedures of standard specifications of ASTM or other national organizations.

(e) Triaxial Compression Tests on Partially Saturated Soils

For partially saturated or dry soils and intermediate geomaterials, the radial expansion of the soil specimen can be calculated approximately by using Poisson's ratio of the soil when selected from the published literature, as described above. New values of Poisson's ratio shall also be available from the triaxial compression tests conducted on saturated 100% saturated specimen, and can be used to reasonably to assume the value of Poisson's ratio. With expandable jacket surrounding the cylindrical soil specimen consisting of partially saturated soils, the uniform radial expansion can be calculated based on selected value of Poisson's ratio and then used to determine radial expansion, change in volume, and change in void ratio, which was not possible to determine accurately before, in the absence of the expandable jacket. The lateral resistance exerted by rubber bands or rings can also be calculated based on modulus of elasticity of rubber and radial strain in the rubber bands or rings (radial strain calculated as radial expansion divided by its diameter).

Earth and broken rock fills of earth and rock fill dams are generally constructed at ±2 percent of optimum moisture content, depending upon which engineering guidelines i.e. of either United States Bureau of Reclamation or US core of engineers are used. Pore pressures develop in an embankment as it compresses under its own weight during construction. When the drainage of air and water is not possible, a pressure develops in the pore-air and pore-water, opposing the externally applied stress (Hilf, 1956, Manglik and Gupta, 1977). Therefore, it is important that the triaxial compression tests are performed in insitu partially saturated condition as laid and constructed at real time, i.e. triaxial compression tests are performed on the specimen of the crushed or broken rock fill extracted on the day that layer was constructed or when only a few feet of fill has been placed over that layer. To predict the pore-air pressure ($u_a$) in kPa, the Hilf equation was further derived by Fredlund et al. (2012) is given below:

$$\Delta u_a = \left\{ 1 \Big/ \left\{ 1 + \frac{[(1 - S_o + hS_o)n_o]}{[(u_{ao} + \Delta u_a)m_h]} \right\} \right\} \Delta \sigma_r \qquad (3)$$

Where $\Delta\sigma_r$=change in applied radial stress (kPa), $n_0$=initial porosity of the soil prior to consolidation, $m_h$=coefficient of horizontal compressibility of the soil skeleton (kPa$^{-1}$).

With use of the expandable jacket which helps in maintaining uniform radial expansion during the test, triaxial compression tests can be performed on partially saturated broken rockfill, clays and silts to measure the pore-air and pore-water pressures, at various values of lateral pressure in the chamber and axial load, to represent the insitu horizontal and overburden stress during various stages of the fill height on a layer. The pore-air and pore-water pressures shall be measured by pore pressure measuring devices located in the control panel. These tests shall properly simulate the field conditions where uniform horizontal displacements under load occurs and predict the expected pore-air and pore-water pressures, which will develop during construction of the embankment to the full height. The Eq. (3) can be further improved when triaxial tests using expandable jacket and LVDT measurement for radial expansion are performed, instead of just depending up on the Hilf or the Fredlund equation. When these tests are performed during design, a proper slope stability analyses can be performed during design for various stages of the height of the dam embankment during construction and the assumed height of reservoir behind the dam embankment; and after completion of the dam embankment at various expected reservoir levels.

Shear strength characteristics of partially saturated soils using expandable jacket to permit uniform radial expansion can be determined accurately. Mohr's failure envelops can be correctly determined using measurements of the pore-water and pore-water pressures, vertical settlement, radial expansion of the soil specimen, and peak deviator stress, when triaxial compression tests are performed on specimens of partially saturated soils at various values of lateral pressures, with use of the expandable jacket surrounding the cylindrical specimen and LVDT measurement of radial expansion. It shall be possible to check assumptions and theories used so far to develop a Mohr's failure envelop for partially saturated soils and to develop new theories and assumptions based on these test results. Thus, the expandable jacket around the cylindrical specimen, will also provide opportunities for research for new and accurate theories to be developed, in addition to providing accurate values of properties of soils and intermediate geomaterials for design.

(f) Mounting Device for LVDT

Chambers with vertical cylindrical acrylic walls are generally used for the tests. Water or fluid is filled in the chamber and pressures up to 150 psi or more, are applied. When LVDTS are not used for measurements inside the chamber, acrylic or metal chambers shall be used for both triaxial and three-dimensional consolidation and settlement tests. It is very difficult to make the LVDT or strain gage waterproof or water resistant, in which cables/wires shall extend from their body within the chamber or exit from the top or bottom platens of the chamber. High pressure sealed LVDTs are available in the industry for displacement measurements in the pressure sealed chambers, hydraulic actuators and pressure vessels, which are generally constructed with heavy-wall 304 series stainless steel. All welded LVDT is highly resistant to corrosive environments. These LVDTs are suitable to very high pressures far exceeding 1000 psi. These LVDTs are generally available in stroke ranges ±0.25 inch (±6.35 mm) to ±1 inch (±25.4 mm) with imperial or metric cores. The body lengths (L) of LVDTS vary from approximately about between 3 to 8 inches (76.2 and 200 mm) depending on stroke length. This type of LVDT is not spring loaded to maintain a proper position. For sealing the high pressure sealed LVDT, it shall be necessary to use metal chambers or sealed reservoirs because then acrylic chambers cannot be used.

Figure 7:
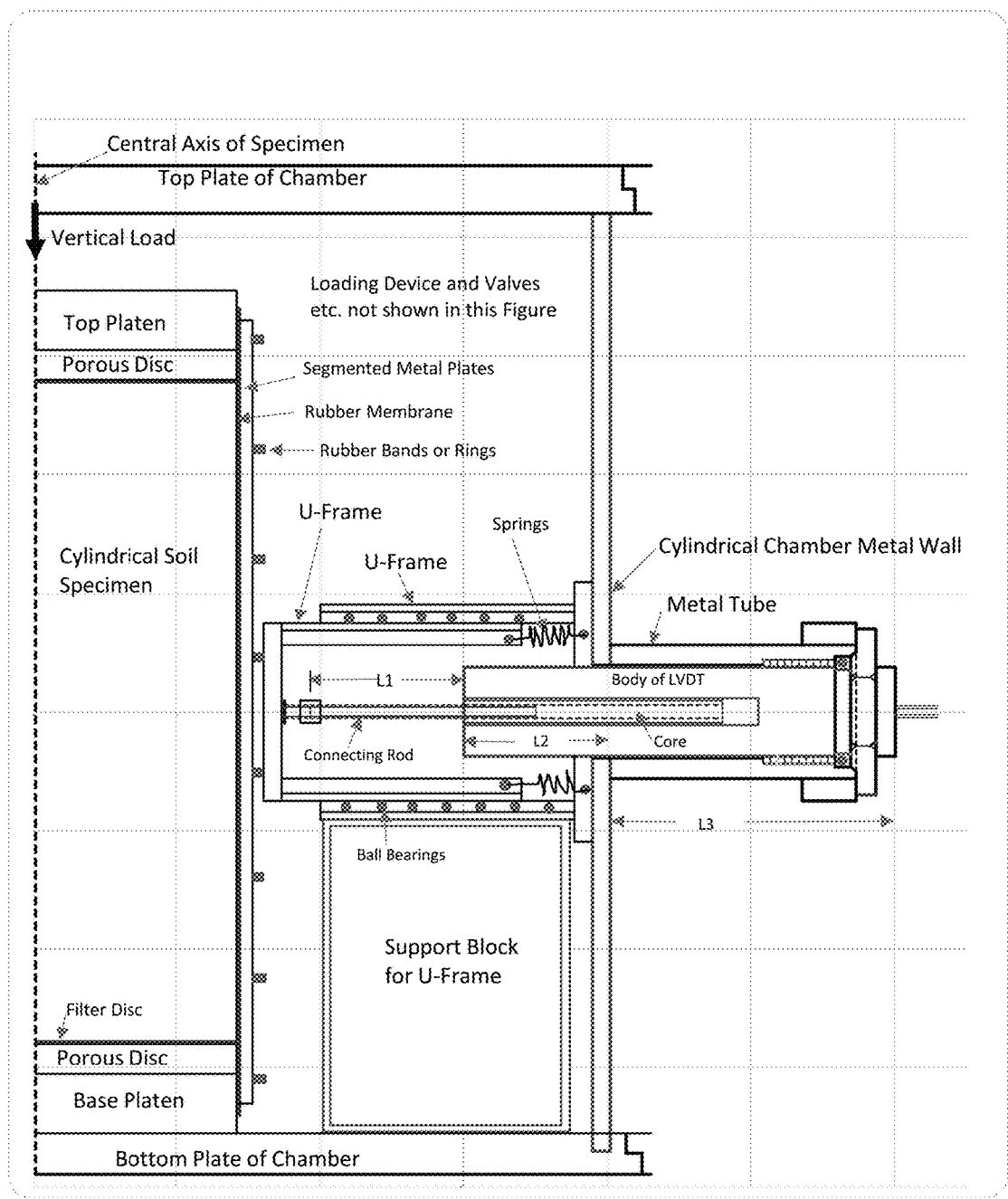
FIG. 7 shows the schematic detail of weld connected metal tube to the metal cylindrical wall of the high pressure chamber, internal (female) threads provided in the metal tube near the outside end of the metal tube, matching the external (male) threads of the high pressure sealed LVDT, high pressure sealed LVDT, connecting rod thread connected to core of the LVDT, connecting rod and the internal face of the U-frame bolted together, facing plate of the U-frame in contact with the expandable jacket, the spring-loaded U frame to maintain the core in proper position during the test and U-frame properly supported on the support block resting on the bottom plate of the chamber.

In FIG. 7, a metal cylindrical chamber (with or without viewing ports) and spring-loaded U-frame for installing LVDT has been selected. In this figure, the metal cylindrical chamber is weld connected to a metal tube with an internal diameter equal to about the outside diameter of the body of the LVDT. At the end of the metal tube, another metal tube is weld connected. The outside vertical surface of both metal tubes is machine finished and polished to a very smooth surface. The size and length of the internal (female threads) provided in the metal tube shall match with the size and length of external (male) threads as provided by the manufacturer in the body of LVDT on its outside end. The core of the LVDT is inserted in the body of LVDT, and positioned so that the outside of the face of the core approximately match with the inside face of body. The connecting rod is threaded to the core. The other end of the connecting rod is thread connected to a spring-loaded U-frame, as shown in FIG. 7. The spring-loaded U-frame slides on the ball bearings both at its top and bottom, as shown in this figure.

The facing plate of the spring-loaded U-frame is designed to keep in contact with the at least one elastomeric rubber band or ring before beginning the test. If tests such as uniaxial compression tests on intact rock cores or concrete cores, which are cylindrical in shape, are being performed and expandable jacket is not used, then the facing plate of the U-frame is in contact with the surface of the rock or concrete core. The springs mounted in the U-frame shall maintain the initial position of the LVDT core via connecting rod at the beginning of the test. When the radial expansion of the specimen takes place during the compression test, the core of the LVDT moves inside tube of the body and provides the value of radial displacement at an instant of time during the test, which is recorded and read by the LVDT signal conditioner, controller and readouts. The facing plate of the spring-loaded U-frame is lubricated, so that it slides smoothly on the rubber rings or bands of the expandable jacket surrounding the cylindrical specimen as shown on FIG. 7 and FIG. 8 or on rock or concrete core to slide down smoothly as shown in FIG. 9, when the cylindrical specimen is undergoing vertical settlement due to the application of vertical load during the test. Therefore, the vertical settlement and radial expansion of the soil specimen or the rock core can occur simultaneously preventing the bending of the LVDT core and thereby preventing the LVDT core to get inclined, i.e. the horizontal position of the LVDT core, the connecting rod and LVDT body remains same throughout the test.

Figure 8:
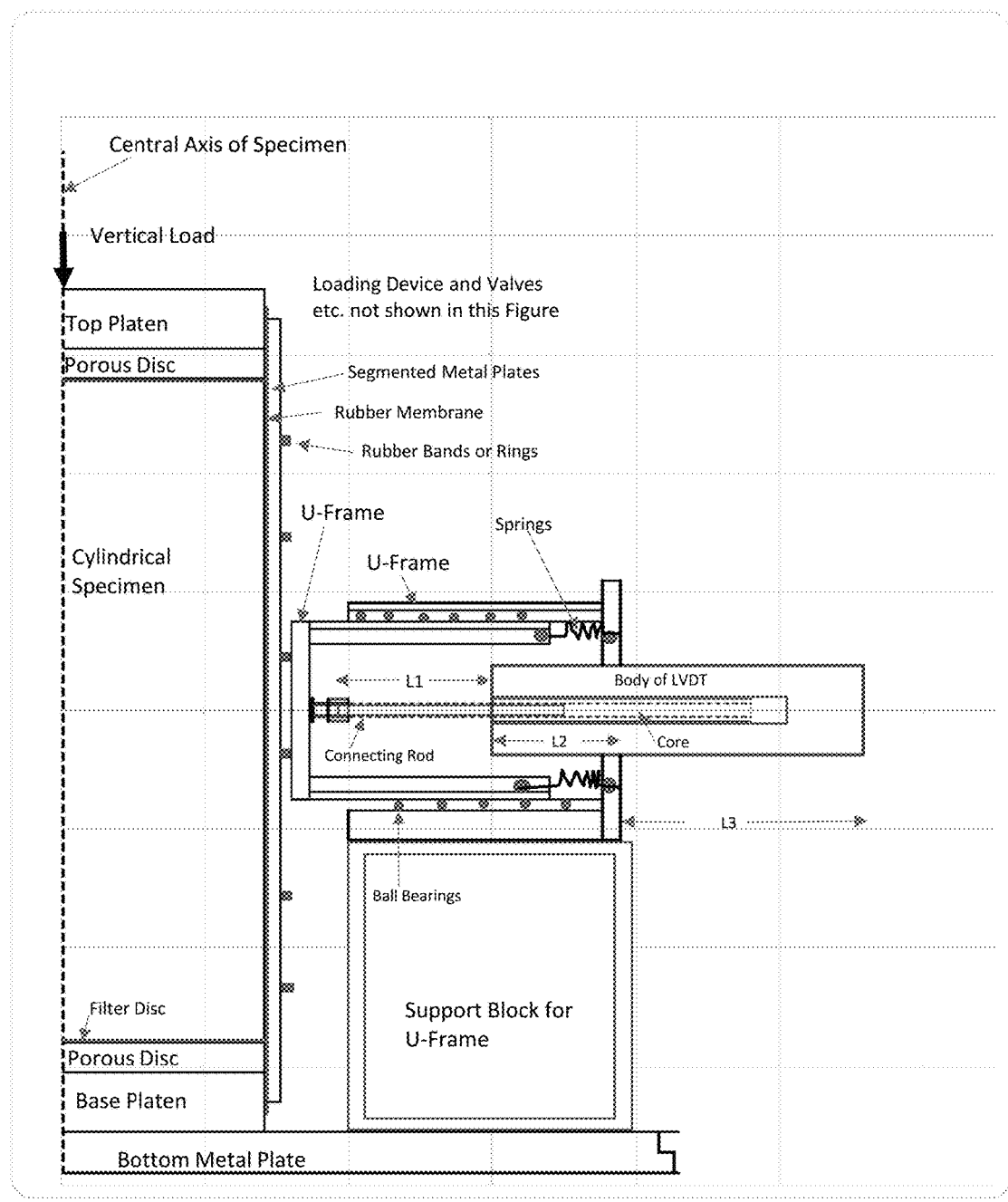
FIG. 8 shows the spring-loaded U-frame in contact with expandable jacket containing cylindrical specimen, guided core LVDT, connecting rod, and support block during unconfined compression tests on cohesive soils and intermediate geomaterials and soft and jointed rocks; similar arrangement shall be made for spring-loaded LVDT, but without connecting rod because connecting rod is not needed for the spring loaded LVDT.
Figure 9:
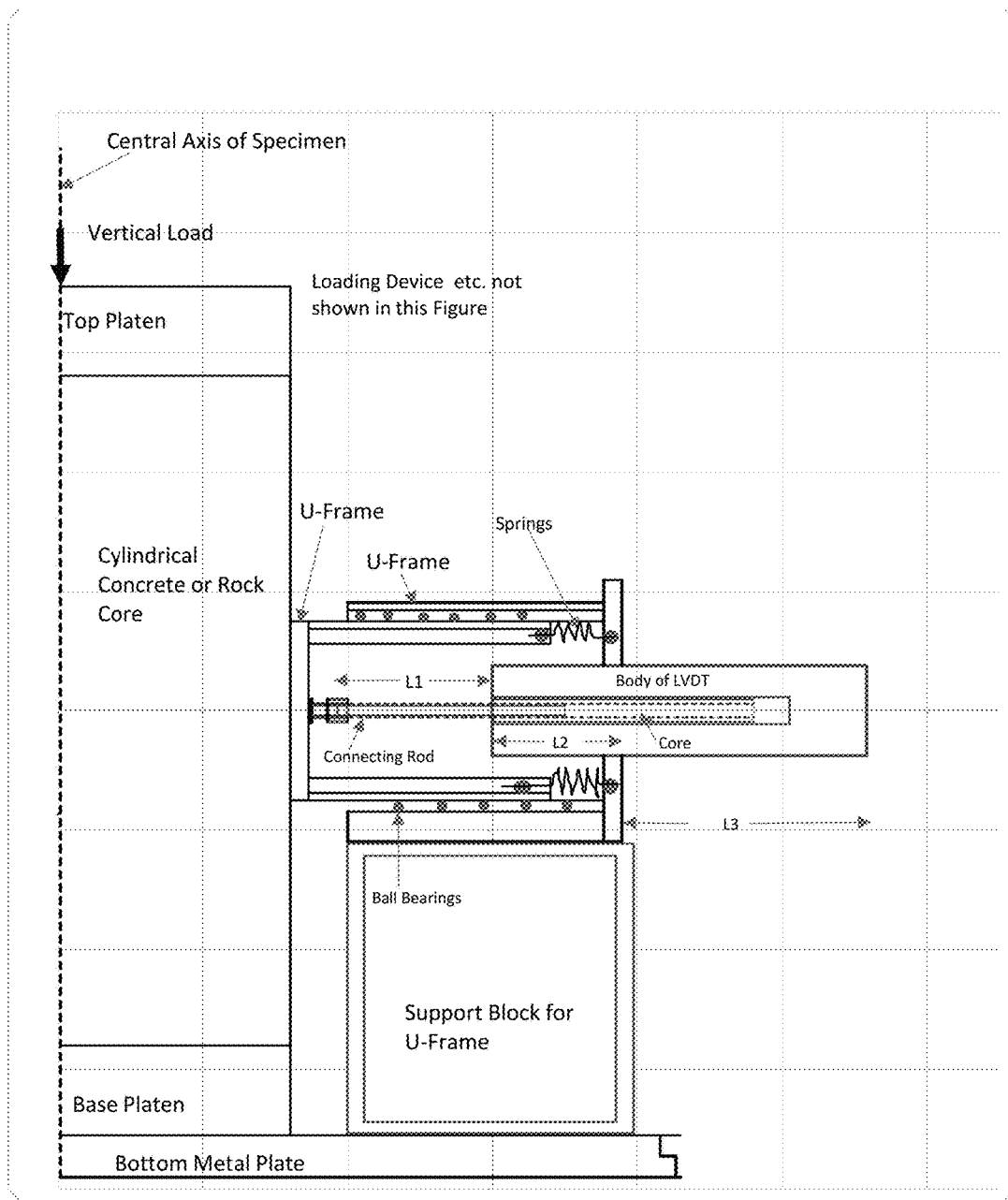
FIG. 9 shows all above details shown in FIG. 8, but spring loaded U-frame is in direct contact with cylindrical specimen of concrete core or intact rock core.

As shown in FIG. 7, FIG. 8 and FIG. 9, L1 is that portion of the length of the connecting rod, which is outside the face of the LVDT body towards the cylindrical specimen, L2 is that portion of the LVDT body which is inside the chamber, and L3 is the length of that portion of the LVDT body which is outside the wall of the metal cylindrical chamber. For the same size specimen and outside diameter of the expandable/flexible ring and inside diameter of the metal chamber, Lengths L1 and L2 can remain same, but Length L3 can vary depending on the length of the body of LVDT (L). The length of the LVDT body is governed by the length of the stroke. Greater the stroke length, greater is the length of the LVDT body and therefore greater will be Length L3. As an option, if necessary, another O-ring may be provided at the other end of the threaded portion for additional insurance for waterproofness, although in most cases it may not be necessary.

The design detail such as the design, the shape and the length of the body and lengths of its various components can vary from manufacturer to manufacture of the LVDT, so details shown can vary from what is shown in FIG. 7, FIG. 8, and FIG. 9. Two LVDTs, each located diametrically opposite each other can also be provided to have measurements at two locations, although measurement by one LVDT could be considered sufficient. Four LVDTs located 90 degrees apart along the perimeter of cylindrical specimen can also be provided to get data radial expansion at four locations. If two LVDTs are used, then two metal tubes diametrically opposite to each other shall be provided to install high pressure sealed LVDTs through them.

Figure 18:
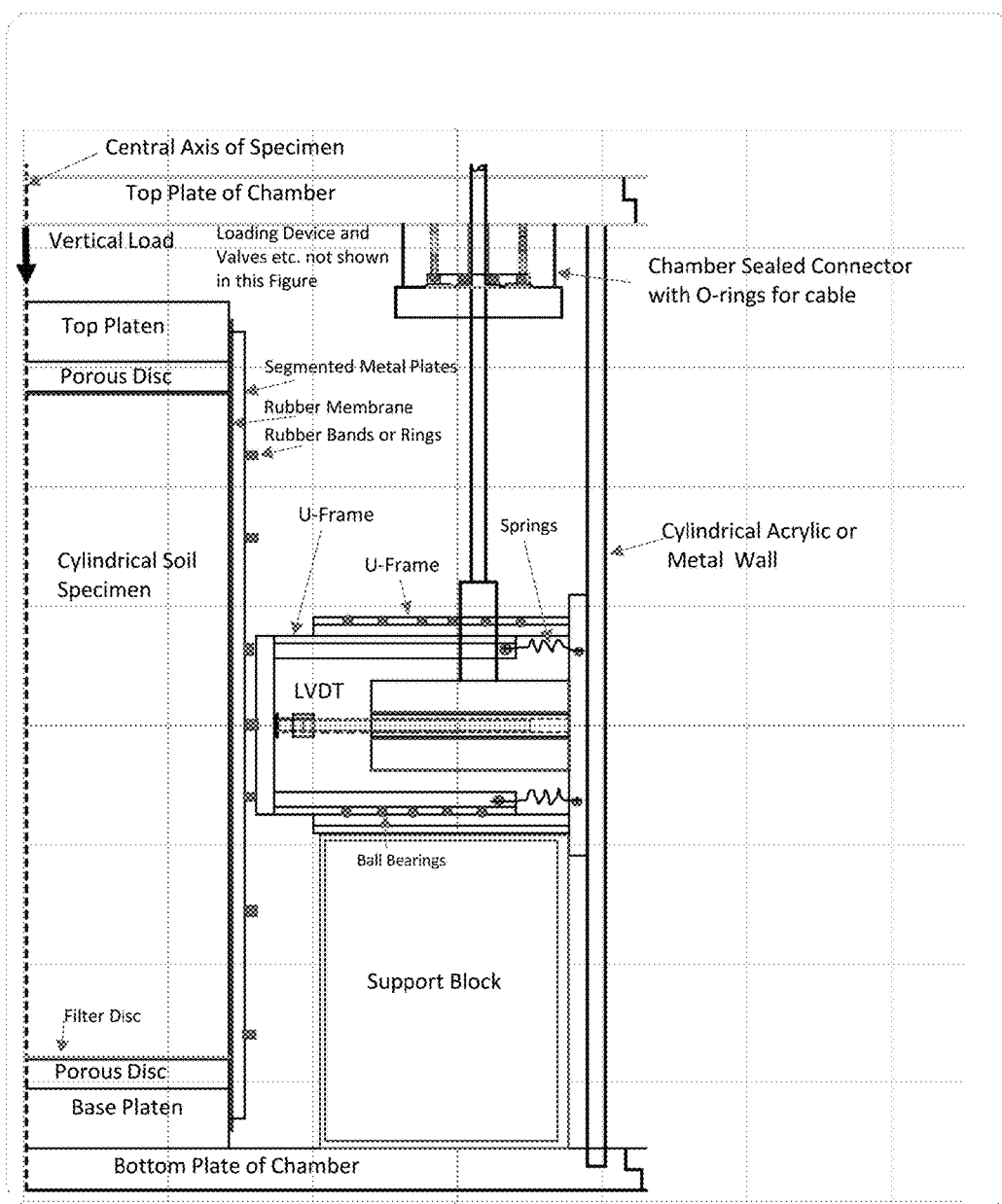
FIG. 18 shows a hermetically sealed LVDT and radial connector (this LVDT requires double sealed cable exit from the radial connector) and a sealed exit for the cable from the top plate of the chamber or sealed reservoir.

The high pressure sealed LVDT as explained can be used only with metal chamber and not with a traditional acrylic chamber. For acrylic chamber, hermetically sealed LVDT position sensors can be successfully used for both triaxial and three-dimensional consolidation tests, as shown in FIG. 18. These types of sensors shall also be used for metal chambers or metal sealed reservoirs both triaxial and three-dimensional chambers. The coil windings are sealed against pressure in chambers and hostile environments and electrical termination is through a sealed radial or sealed axial connector. The pre-built LVDT connectors are constructed with PVC jacket, multi-conductor shielded cable, with a heavy duty, 6-piece aluminum-alloy connector with soldered connection. For extra precaution for waterproof connection, a fused tape which is water-proof or specially designed waterproof fitting to make the connection waterproof for water pressure in triaxial chamber. The shielded cable shall exit from the top metal platen of the triaxial chamber or sealed reservoir either through bulkhead connectors or specially designed and constructed in the machine shop.

There several types of LVDT available in the industry. Spring-loaded LVDT and guided core LVDT can be used in unsubmerged conditions, such as for measuring radial expansion during unconfined compression tests on cohesive soils and intermediate geomaterials and during uniaxial compression strength tests on concrete cores and rocks. Hermetically sealed LVDT (i.e. high pressure sealed LVDT) with radial connector and sealed stainless steel housings with cable exit (double sealed using internal rubber gland plus shrink tube) should be used in pressure acrylic or metal chambers. High pressure sealed LVDT with axial connector can only be used in high pressure metal chambers. Some hermetically sealed LVDT with radial connector which do not have double sealed radial connector and cable exit can be used in open reservoirs, however the radial connector and cable exit should be properly sealed by a fuse tape to protect against moisture and water in the open reservoir.

The two examples, one for high pressure sealed LVDT with axial connector with sealed exit from the cylindrical metal wall and other for high pressure sealed (i.e. hermetically sealed) LVDT with radial connector (with double sealed cable exit) with sealed exit from the top metal plate of the acrylic or metal chamber or sealed reservoir have been shown in this application. There are several other types of sealed LVDT which will require different details that shown in FIG. 7, FIG. 17 and FIG. 18, but all such LVDTs cannot be covered in this application as new models shall keep on coming in future. LVDT measurements of the radial expansion of a cylindrical specimen shall afford calculation of the radial strain and lateral resistance exerted by the rubber bands or rings on the specimen, and shall avoid to solely depend on calculation based on Poisson's ratio or calculations based of the pore-water expelled out to the burette.

(g) Triaxial Tests on Cohesionless Soils

Undisturbed samples of cohesive soils can be extracted from the subsurface at the selected depth and tested in the laboratory. Undisturbed samples of cohesionless soils cannot be extracted from subsurface from any depth, unless the soil is frozen in advance by well-known freezing methods at the depths from where samples are to be extracted. Remolded specimens for cohesive soils when necessary for embankment fills are prepared in laboratory and tested for the triaxial or unconfined compressive strength of the cohesive soil. The remolded specimen of cohesionless soils are prepared in metal molds covered inside by a rubber membrane. The rubber membrane is kept stretched and taut by applying vacuum through a flexible tube, and the cohesionless soils are compacted inside the mold by various compaction methods, the membrane is flipped over the bottom and top platen and then a rubber O-ring is slipped over the platens and then mold is removed. The specimen maintains its shape due to the application of vacuum through the tube from bottom platen. (NOTE; There are standard methods available, which are used to compact cohesionless soils or intermediate geomaterials for triaxial tests, which need to be followed). Expandable jacket is installed around the membrane surrounding the cylindrical specimen. Expandable jacket when used for these tests will not permit barrel shape to form and permit uniform radial expansion affording calculation of the shear strength, and volume change characteristics correctly. When cohesionless soils are saturated in the triaxial tests, the radial expansion of the cylindrical specimen can be calculated from the measured value of pore-water expelled from the specimen during the test and measured vertical displacement, without requiring LVDT measurements. For dry soils, LVDT measurements for radial expansion of the cylindrical specimen shall be required unless it is approximately calculated using the assumed values of Poisson's ratio.

The triaxial compression tests without use of expandable jacket do not provide accurate estimate of horizontal and vertical settlements and modulus of elasticity because cylindrical specimen forms barrel shape and because the lateral stresses do not increase but remain equal to the applied chamber pressure throughout the test, i.e. the lateral stresses do not increase like that in insitu conditions as is estimated by theory of elasticity and theory of cavity expansion. But with the use of expandable jacket surrounding the cylindrical specimen, the lateral stresses shall increase similar to the insitu condition, providing more accurate horizontal and vertical settlements.

For computer savvy engineers or technicians and those very familiar to electronic measurements and direct recording of the data to the computer, the triaxial compression tests when conducted with LVDT measurements for radial expansion, digital gages for vertical displacement, pore-pressure measurement by electronic piezo-transducers, vertical load by load cells, and other items also by electronic measuring devices shall be very desirable and then they analyze data on computer, and therefore, the option of the LVDT for radial measurement has been kept for triaxial compression tests for all types of soils and intermediate geomaterials whether in 100% saturated or partially saturated state. For engineers and technicians who are not very familiar to electronic measurements, the triaxial compression tests when performed without LVDT measurements for radial expansion, triaxial type load system with proving ring, and dial gage measurement for vertical displacement shall be preferable, therefore this option has also been kept in this application.

(h) Use of Expandable Jacket for Unconfined Compression Tests on Cohesive Soils and Intermediate Geomaterials and Uniaxial Strength Test on Soft and Jointed Rocks, Intact Rock Cores and Concrete Cores.

Uniaxial compressive strength tests are performed on the undisturbed or remolded specimen of cohesive soils, cohesive intermediate materials and soft rock cores and fissured and jointed rock cores. The expandable jacket when used shall not let the specimen break prematurely and shall allow uniform radial expansion for accurate determination of the compressive strength. The expandable jacket shall also not allow the premature failure along the joints or fissured soft rocks and then shall represent overall strength of insitu rocks, not solely influenced by the joints.

When Poisson's ratio of the specimen is required or to include the effect of radial expansion of the specimen on the strength is required, the LVDT measurement for radial expansion of the specimen shall be required, or otherwise it can be calculated based on assumed Poisson's ratio. The schematic detail of mounting the LVDT using sliding spring-loaded U-frame is shown in FIG. 8. In this case, LVDT used for pressure chambers is not required. Instead, the spring loaded LVDT or sliding core LVDT without springs as available in the industry shall be used. Spring loaded U-frame shall be necessary for loaded guided core LVDT which are not spring loaded, however for spring loaded LVDT, the use of spring loaded U-frame is optional, but can still be used. The U-frame without springs can also be used for spring loaded LVDTs.

When the compressive strength of intact rock cores or concrete rock cores is determined, then expandable jacket shall not be used because it is then not required. In FIG. 9, the schematic detail of spring loaded U-frame with attachment for LVDT is shown. The facing plate of the U-frame is in contact with the rock or concrete core. The LVDT measurements for radial expansion are needed to determine the Poisson's ratio of intact rock core or concrete core.

(II) Test Device to Determine Three-Dimensional Consoildation and Settlement Properties In this application, the term flexible ring surrounding a cylindrical specimen has been used when the height of the specimen is less than its diameter {height varying between about ¾th of the diameter or ½ inch (12.7 mm)} and the term expandable jacket surrounding the cylindrical specimen has been used when height of the cylindrical specimen is about equal or greater than two times of the diameter. However, the structure components and their arrangement around the cylindrical specimen and assembly methods for both are the same. For three-dimensional consolidation and three-dimensional settlement tests, flexible ring shall be used in place of fixed ring as is used in one-dimensional consolidation tests.

(a) Standard Test Methods for Determining Consolidation Properties and Their Limitations The standard test method for one-dimensional consolidation properties of soils using incremental loading is described in ASTM Designation: D2435/D2435M-11 and in AASHTO 216. International and national organizations of several countries have their own standards for this test. The test apparatus for one-dimensional consolidation test consists of a rigid ring. The cylindrical specimen of cohesive soils and intermediate geomaterials is pushed into the ring to perform the test, creating some disturbance in undisturbed specimen, first in shaping and cutting to conform to size of the inside diameter of the fixed ring, then pushing the specimen in the fixed ring and then finally caused by some small separation between the cylindrical specimen and the inside surface of the fixed ring.

When foundation loads are transmitted to cohesive subsoils, there is a tendency for a volumetric strain which in the case of saturated material is manifested in an increase in pore water pressure. With sufficient elapsed time, water flows out of the soil pores, permitting excess pore-water pressure to dissipate. The analysis of the volumetric strains which result, and the vertical settlements accompanying them, is simplified if we assume that such strains occur only in vertical direction. Such an assumption may not be unreasonable when the geometric and boundary conditions in the field are such that vertical strains dominate. For example, when dimensions of the loaded area are large relative to the thickness of the compressible stratum and/or when the compressible material lies between two stiffer soils whose presence tends to reduce the magnitude of horizontal strains, an approximately one-dimensional compression of the soil will occur (Perloff and Baron, 1976).

However, generally, the examples as mentioned above very seldom or never happens. In most cases, three-dimensional consolidation and settlements occur. Therefore, volumetric strains in soils significantly depend on displacements both in vertical and horizontal or radial directions. In those cases, in which the thickness of compressible strata is large related to the loaded area, the three-dimensional nature of the problem shall influence the magnitude and rate of settlement. Although numerical analysis methods offer the prospect of rational consideration of three-dimensional compression effects, they have not proven useful in practice (Winterkorn and Fang, 1990). In view of this, semi-empirical approaches have been used for estimating three-dimensional consolidation properties. The most commonly applied method was developed by Skempton and Bjerrum (1957), using two assumptions: (1) even though the induced excess pore water results from three-dimensional effects, the settlements are assumed as one-dimensional, (2) to account for three-dimensional consolidation, the vertical settlement at the centerline is predicted as equal to product of one-dimensional consolidation settlement times a factor $\lambda$. The value of $\lambda$ is estimated using a chart, which has been plotted based on overconsolidation ratio and ratio of the width of foundation with thickness of consolidating stratum (HRB, 1973).

The coefficients of permeability and consolidation in horizontal direction has been found to be much greater than the coefficients of permeability and consolidation in vertical direction of the same soil deposits or stratum (Terzaghi et al. 1996). Depending on the anisotropy of the soil deposits or presence of very thin sand/silt layers in the soil deposits, the coefficients of permeability and consolidation in horizontal direction could be even 10 times greater than the coefficients of permeability and consolidation in vertical direction. In such cases, the method of Skempton and Bjerrum (1957) using $\lambda$ factor cannot be applied. In view of the above, it is very important to develop a test which can determine the three-dimensional consolidation properties of soil deposits. To solve this problem of more than 100 years, the inventor has invented a three-dimensional consolidation test device which permits the dissipation of excess pore water pressure both in vertical and horizontal (radial directions) directions along with settlements occurring both in vertical and horizontal (radial) directions.

Settlement tests can be performed on soils, which do not generate pore pressures during triaxial compression tests using expandable jacket around the soil specimen at various values of fluid pressure, but more accurate tests can be done in the flexible ring to avoid shear stresses, which could develop in triaxial compression tests. So far one-dimensional settlement tests on soils, which do not generate excess pore-water pressure or dissipate as soon as load is applied, have been done in the fixed ring, like one-dimensional consolidation tests on cohesive soils. Since it is difficult to extract undisturbed samples of sandy samples in the field, the tests are performed on disturbed samples by compacting the soil in a mold by various compacting methods at desired densities. The height of these samples can vary from 1 inch to about equal to about the $\frac{3}{4}^{th}$ diameter of the cylindrical specimen.

(b) Three-dimensional Consolidation and Settlement Test Device

Figure 10A:
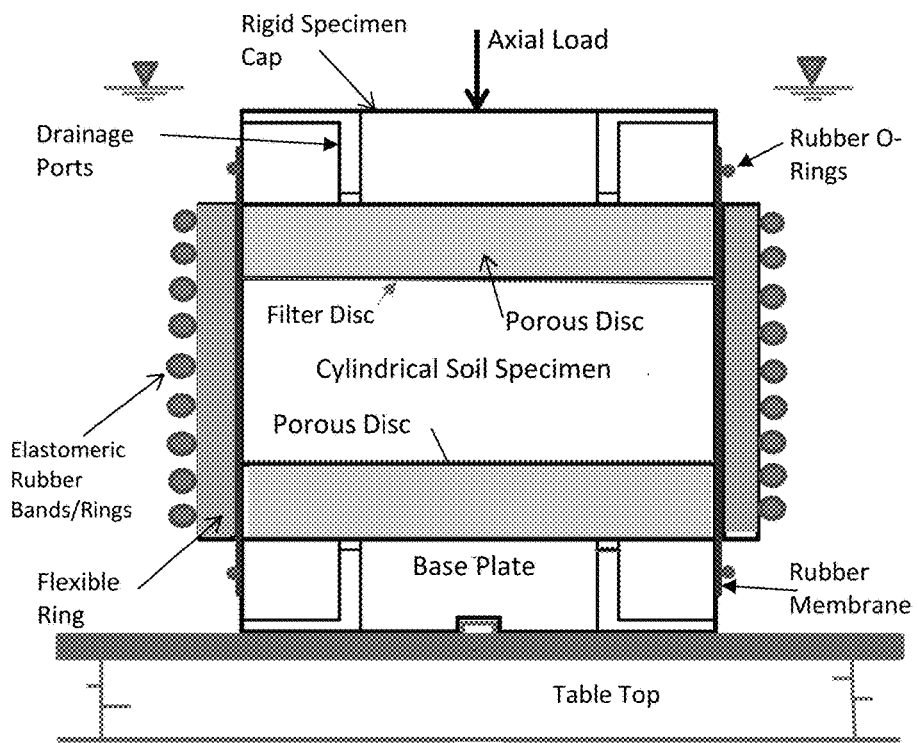
FIG. 10A shows the test device for determining coefficient of consolidation in vertical direction, when the device is to be placed in the open reservoir.

FIG. 10A shows the schematic detail of a test when dissipation of excess pore water pressures can take place only in vertical direction, but unlike one-dimensional consolidation test, displacements both in vertical and horizontal (radial) directions can take place simultaneously when the vertical load is applied. This test shall permit the determination of coefficient of consolidation in vertical direction and shall simulate field conditions. This test device as shown FIG. 10A, requires placing the flexible ring containing the cylindrical specimen in an open reservoir or unsealed reservoir, using either incremental type loading device or triaxial type loading system without the use of the control panel.

Figure 10B:
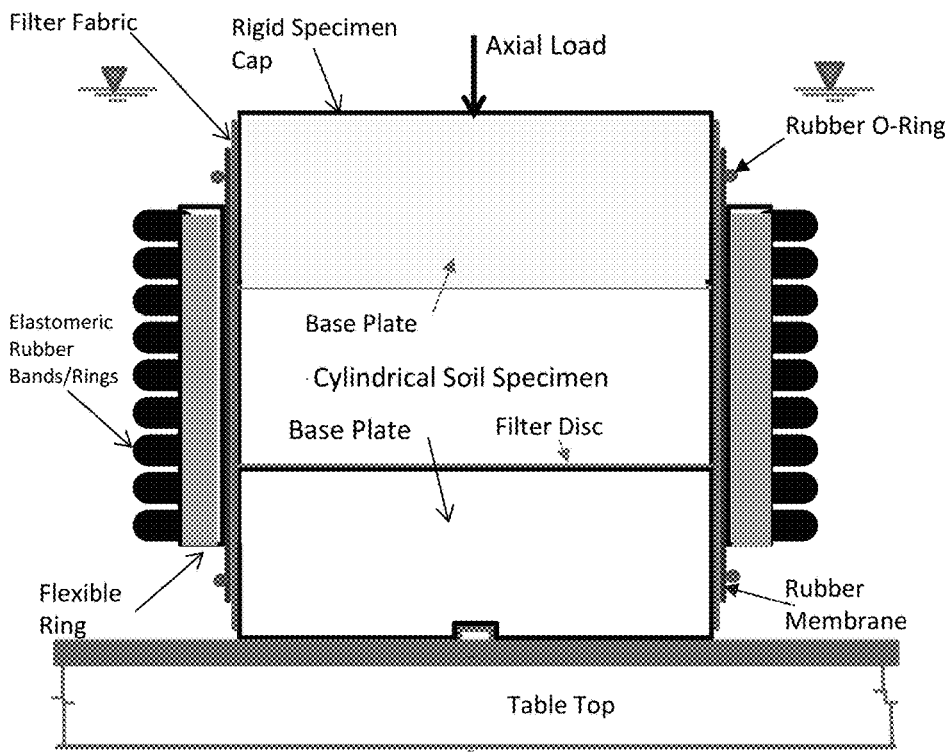
FIG. 10B shows the test device for determining coefficient of consolidation in horizontal direction, when the device is to be placed in the open reservoir.

FIG. 10B shows the schematic detail of a test when dissipation of excess pore water pressures can take place only in horizontal (radial directions) direction, but unlike one-dimensional consolidation test, displacements both in vertical and horizontal (radial) directions can take place simultaneously when the vertical load is applied. This test shall permit the determination of coefficient of consolidation in horizontal direction. For this test, a filter fabric or filter paper (preferably with filter paper in two layers for effective drainage) is wrapped around the soil specimen. A thick rubber membrane is then installed around the filter fabric. It may be noted that the filter fabric extends both below and top of the rubber membrane to allow dissipation of pore-water pressures accompanied by outflow of excess pore-water to the reservoir. Porous discs are not required for this test as dissipation of pore-water pressures in vertical direction are not allowed in this test device. This test device as shown FIG. 10B, requires placing the flexible ring containing the cylindrical specimen in an open reservoir or unsealed reservoir, using either incremental loading device or triaxial type loading system without the use of the control panel.

Figure 11A:
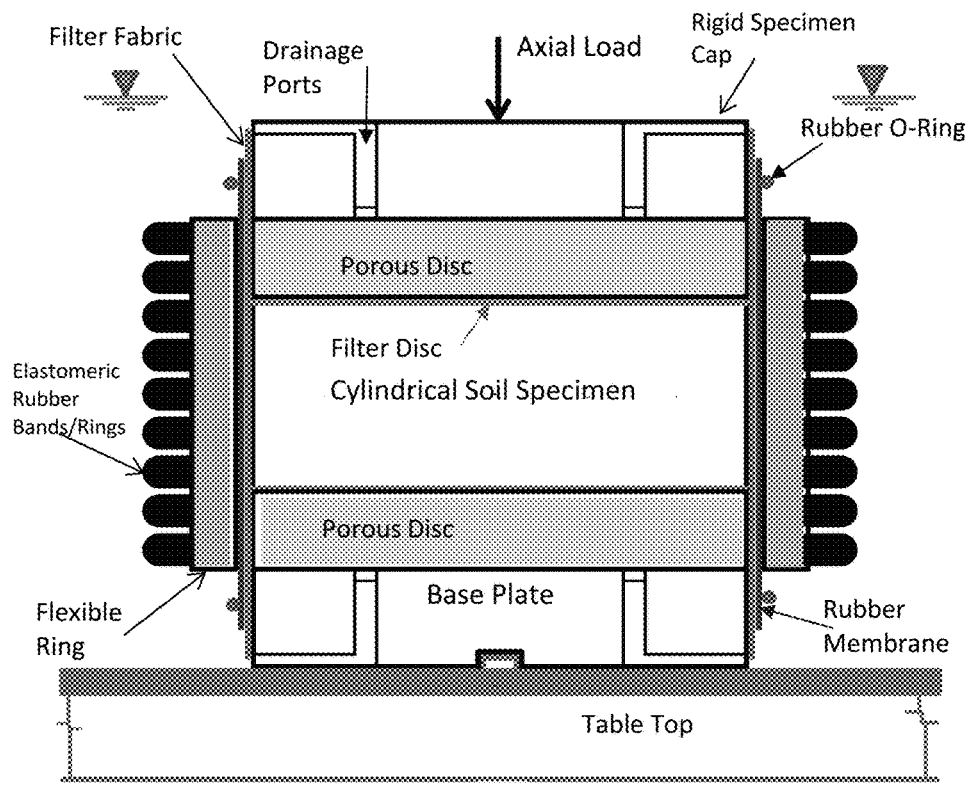
FIG. 11A shows the test device for determining three-dimensional coefficient of consolidation, when the device is to be placed in the open reservoir.

FIG. 11A shows the schematic detail of a test when dissipation of excess pore water pressures can take place both in vertical and horizontal (radial) directions, but unlike one-dimensional consolidation test, displacements both in vertical and horizontal (radial) directions can take place simultaneously when the vertical load is applied. This test shall permit the determination of three-dimensional coefficient of consolidation. In this test, three-dimensional consolidation shall take place the same way as will take place in insitu conditions in the field. As shown in FIG. 11A, porous discs are used to allow dissipation of pore-water pressures in vertical direction and filter fabric or filter paper around soil specimen is used to allow dissipation of excess pore-water pressures in horizontal (radial) direction. It may be noted that the filter fabric or filter paper extends both below and top of the rubber membrane to allow dissipation of pore-water pressures accompanied by outflow of excess pore-water to the reservoir. This test device as shown FIG. 11A, requires placing the flexible ring containing the cylindrical specimen in an open reservoir or unsealed reservoir, using either incremental loading device or triaxial type loading system without the use of the control panel.

For the test systems using FIG. 10A, FIG. 10B and FIG. 11A, the uniform radial expansion of the cylindrical specimen shall be approximately calculated based on the assumed value of Poisson's ratio. Normally, the value of radial expansion and the value of lateral resistance provided by the rubber membrane and rubber bands or rings shall not be required, however, the determination of the approximate values are important to be evaluated to know that the lateral restraint provided the fabric filter, rubber membrane, and rubber bands is approximately during the test is equal to flexible restraint provided by the insitu soil at the selected depth from where the specimen was extracted when vertical load is applied at that depth. The calculated value of the vertical stress shall be based on the area of cross-section calculated on the approximate value of radial expansion of the specimen, based on the assumed value of Poisson's ratio. For design purposes, the test results using the assumed value of Poisson's ratio, shall be quite reasonable to use. The main advantage of not using LVDT measurements shall be that these tests can be done in site laboratories or small laboratories in the same so far one-dimension consolidation tests are normally performed, where the engineers and technicians are not very conversant to the LVDT measurements or electronic measurements. The cost of the test device will then be quite economical.

Figure 11B:
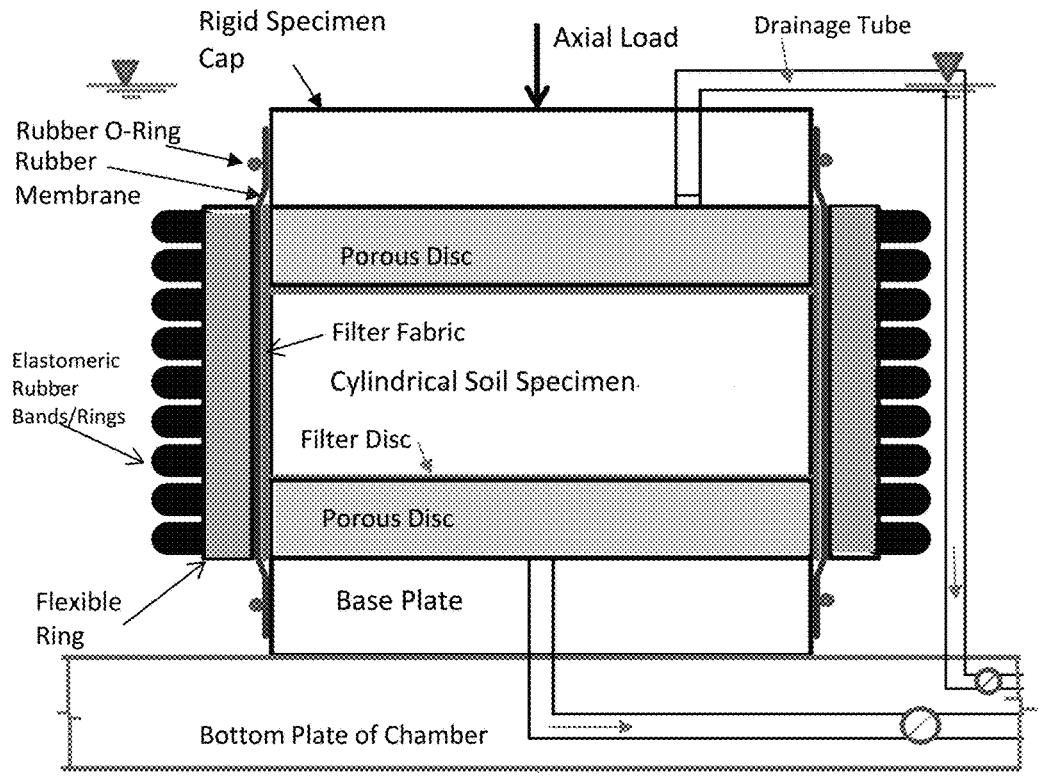
FIG. 11B shows the test device for determining three-dimensional coefficient of consolidation, while the device is to be placed in the sealed reservoir or triaxial type chamber.

The test device shown in FIG. 11B is performed by placing a chamber or sealed reservoir around the flexible ring containing the cylindrical specimen, using either incremental loading device (like one-dimensional consolidation test device) or triaxial type loading system and for both loading systems using the triaxial type control panel. This figure shows the schematic detail of a test when dissipation of excess pore-water pressures can take place both in vertical and horizontal (radial) directions, but unlike one-dimensional consolidation test, displacements both in vertical and horizontal (radial) directions can take place simultaneously when the vertical load is applied. This test shall permit the determination of three-dimensional coefficient of consolidation. In this test, three-dimensional consolidation shall take place the same way as will take place in insitu conditions in the field. As shown in FIG. 11B, porous discs are used to allow dissipation of pore-water pressures in vertical direction and filter fabric or filter paper (preferable two layers of filter paper for effective drainage) around the cylindrical specimen is used to allow dissipation of excess pore-water pressures in horizontal (radial) direction. The filter fabric in this case, does not extend beyond the rubber membrane, but remains inside the rubber membrane, the pore-water is collected by the filter fabric and is lead to wards the upper and lower porous discs to outflow through valves and flexible tubes to control panel and collect in the burette for measurement. The measured pore-water expelled out of the cylindrical specimen along with measured vertical displacement is used to calculate accurately the uniform radial expansion of the specimen and the lateral resistance provided by the rubber membrane, filter fabric and rubber bands or rings, without requiring LVDT measurements for the radial expansion.

Figure 12A:
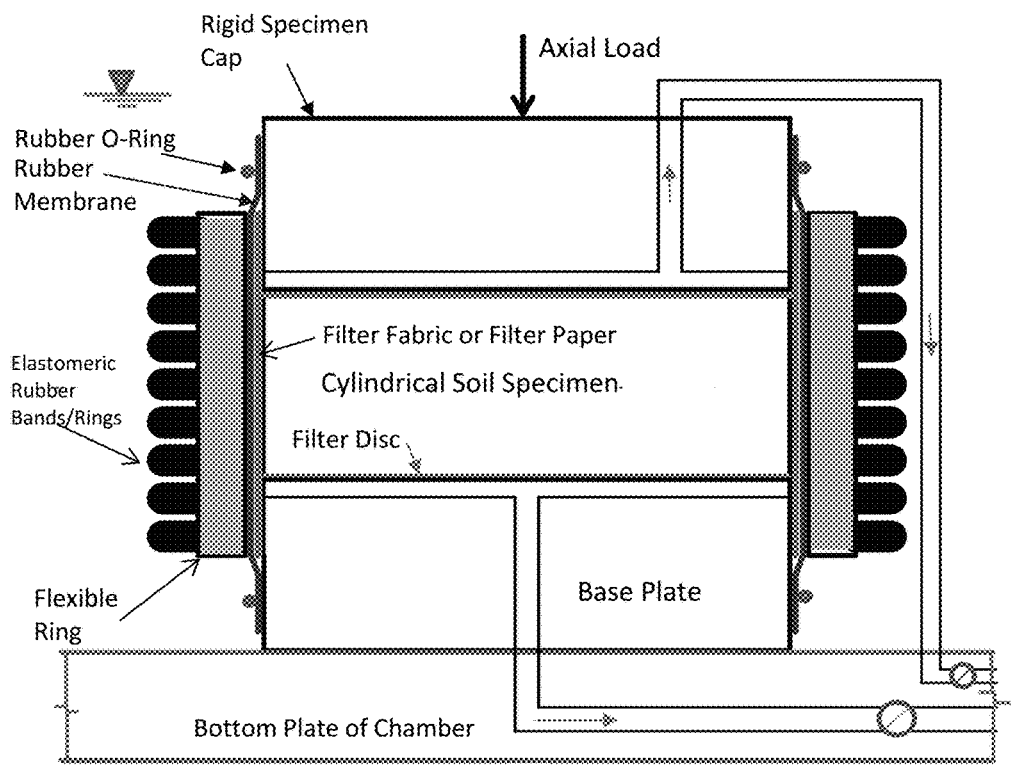
FIG. 12A shows the test device for determining coefficient of consolidation in horizontal direction, when the device is to be placed in the sealed reservoir or triaxial type chamber.
Figure 12B:
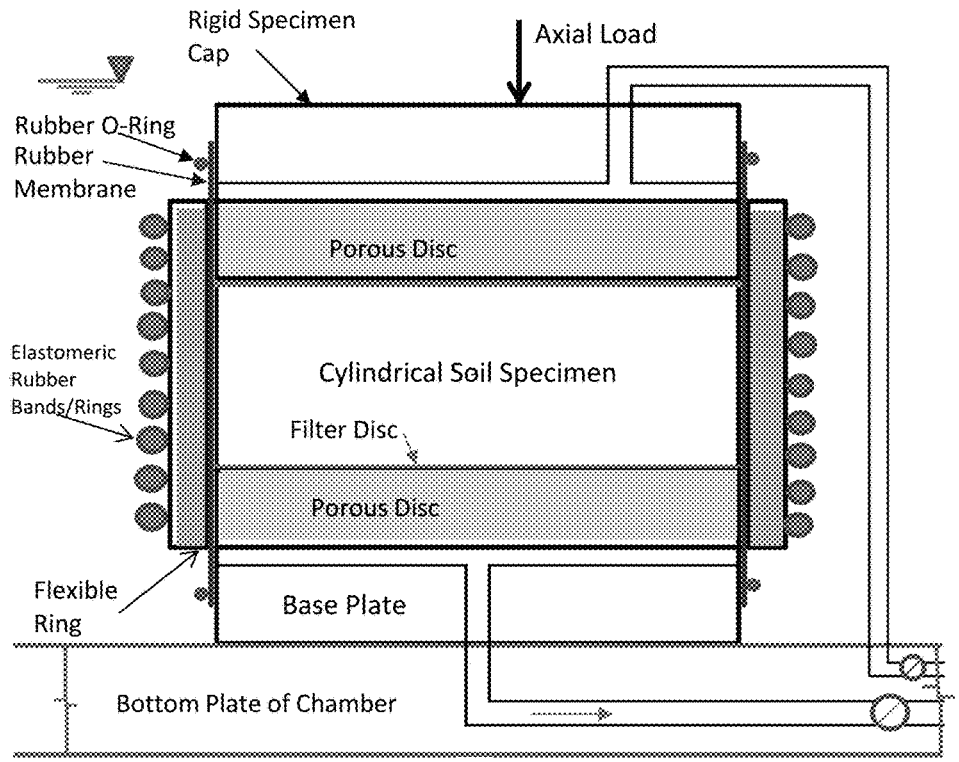
FIG. 12B shows the test device for determining coefficient of consolidation in vertical direction, when the device is to be placed in the sealed reservoir or triaxial type chamber.

In FIG. 12A and FIG. 12B, the test system is same as shown in FIG. 10A and FIG. 10B, but in this case the test device is placed in the chamber or sealed reservoir, using incremental loading system or triaxial type loading system with triaxial type control panel. The test device in FIG. 12A, shall be used to determine the coefficient of consolidation in horizontal direction, while both vertical and horizontal settlements to occur during application of vertical load. As shown in FIG. 12A, the filter fabric or filter paper in this case, does not extend beyond the rubber membrane, but remains inside the rubber membrane, the pore-water is collected by the filter fabric and is lead to wards the upper and lower porous discs to outflow through valves and flexible tubes to control panel and collect in the burette for measurement.

The test device shown in FIG. 12B, shall be used to determine the coefficient of consolidation in vertical direction, while both vertical and horizontal settlements to occur during application of vertical load. The fabric filter or filter paper surrounding the specimen is not used for this test and the rubber membrane is installed around the cylindrical specimen. The device is placed in a triaxial type chamber or sealed reservoir. In FIG. 12B, the excess pore-water is expelled out through porous discs, valves and flexible tubes to control panel and collect in burette for measurement.

It may be noted that in all these tests, a filter disc (usually a filter paper disc, although machine woven thin fabric filter disc can be also successfully used) is placed between the bottom porous stone and the bottom of soil specimen, and between the top of the specimen and the top porous stone, so that the porous stones are not clogged by soil and intermediate geomaterials. One layer of non-woven filter fabric to be wrapped around the cylindrical specimen may be sufficient for effective drainage, but two layers of machine woven filter fabric to be wrapped around the cylindrical specimen. Similarly, two layers of filter paper to be wrapped around the cylindrical specimen may be required for effective drainage. In FIG. 10A, FIG. 10B, FIG. 11A, FIG. 13A, the open or unsealed reservoir and loading device has not been shown, but has been shown in FIG. 15B. In FIG. 11B, FIG. 12A, FIG. 12B, and FIG. 13B, the triaxial type chamber or sealed reservoir, loading device and control panel has not been shown, but can be seen in FIG. 16B, 16C, FIG. 17, FIG. 18, and FIG. 19.

If the field conditions are such that the drainage boundary is only at the top of the soil deposit and not below it, then the porous disc at the bottom shall be replaced by metal plate with no drainage port in it.

If the field conditions are such that the drainage boundary is only at the bottom of the soil deposit and not above it, then the porous disc at the top shall be replaced by metal plate with no drainage port in it. Generally, the above-mentioned tests shall be performed on the soil specimen extracted from the same Shelby tube, i.e. from the same soil strata. The tests can also be performed in remolded or reconstituted specimen of cohesive soils and intermediate geomaterials, after compacting in a split mold. The test setup shown in FIG. 11B or FIG. 12A shall be used to determine three-dimensional coefficient of consolidation. These tests shall also allow to develop correlations between three-dimensional coefficient of consolidation and coefficient of consolidation in vertical direction using test setup shown in FIG. 10A or FIG. 12B and between coefficient of consolidation in horizontal direction using test setup shown in FIG. 10B or 12A have been determined. Time rate of settlement both in vertical and horizontal directions and rate of volume change of a soil deposit can be accurately determined from the results available from these tests. Numerical analyses such as finite element or finite difference analyses based on the results of these consolidation tests can then be made accurately to determine the volume change, rate of volume change with time, horizontal and vertical displacement, rates of horizontal and vertical displacements with time, and rate of increase in vertical and horizontal stresses with time, and rate of dissipation of excess pore-water pressures, in each small soil element of the soil element matrix.

Figure 13A:
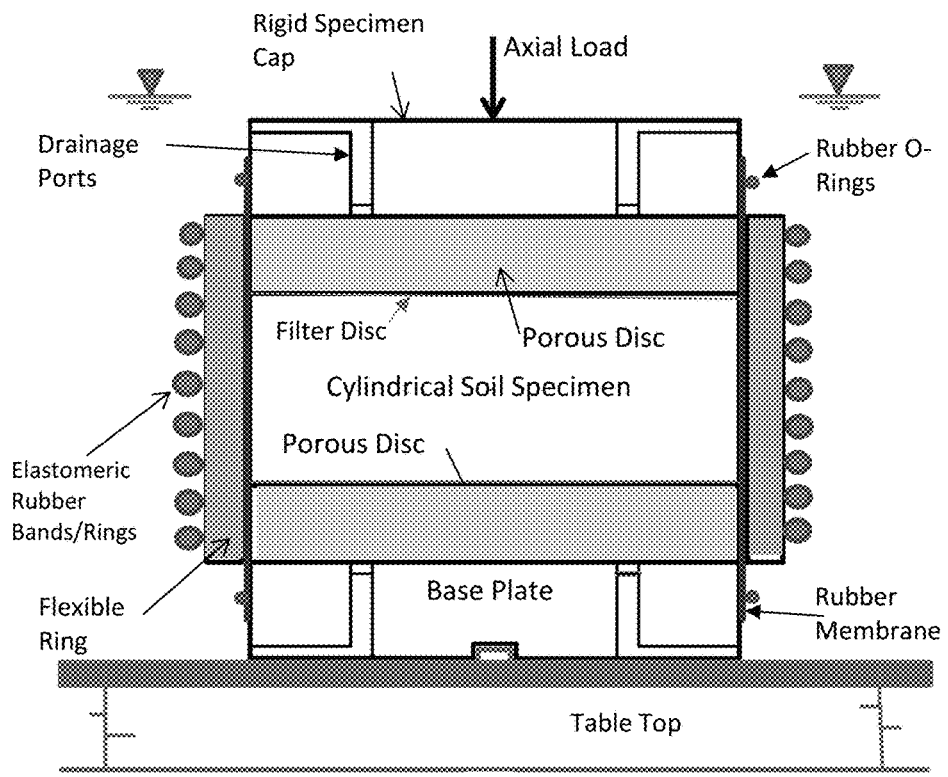
FIG. 13A shows the test device for determining settlement characteristics of soils and geomaterials, which do not generate excess pore-pressures or if excess pore-pressures develop, they dissipate as soon as generated, when the device is to be placed in the open reservoir.
Figure 13B:
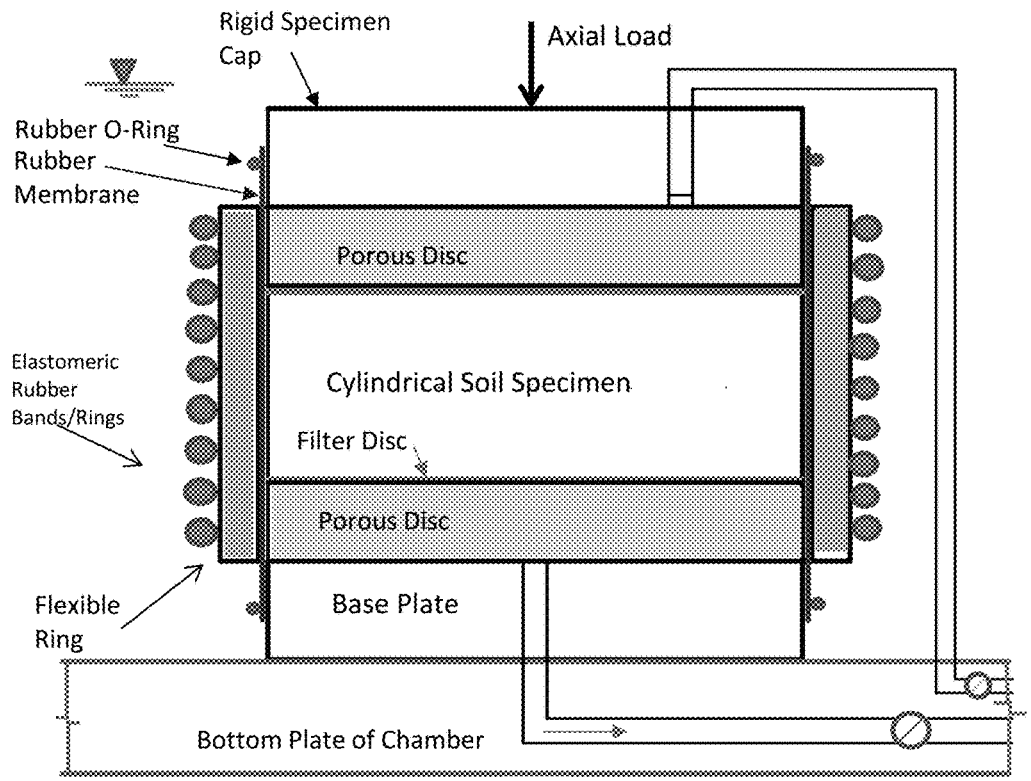
FIG. 13B shows the test device for determining settlement characteristics of soils and geomaterials, which do not generate excess pore-pressures or if excess pore-pressures develop, they dissipate as soon as generated, and when the device is to be placed in the sealed reservoir or triaxial type chamber.

FIG. 13A and FIG. 13B show the schematic detail of a three-dimensional settlement tests on soil which do not generate excess pore-water pressures or which dissipate as soon as the vertical load increment is applied. The rubber membrane surround the cylindrical specimen, thereafter segmental circular arch shaped metal plates are installed and the elastomeric rubber bands or rings are slipped to maintain metal plates in correct position. There is no filter fabric around the cylindrical specimen is required.

The cohesion-less soils shall be placed and compacted in a mold after stretching a rubber membrane around inner cylindrical surface of the mold; a vacuum of about 2 psi shall be applied by lowering a pinched tube about 2 to 4 ft (0.69 to 1.2 m) below the top of table as per prescribed procedures available for preparing cylindrical specimen of cohesionless soils and intermediate geomaterials for tests. When compaction of the soil is accomplished to desired density by various methods, the rubber membrane is slipped on the top and bottom platens, rubber-O rings mounted on the rubber membrane to seal it with platens, then the mold is removed, the rubber membrane is kept taut by applying vacuum through a tube via bottom platen, the segmental plates installed using the removable attachments as described above and elastomeric rubber bands or rings are slipped on the rubber membrane around the metal segmental plates. Tests using either a triaxial type chamber or sealed reservoir or an open reservoir is performed using incremental loads applied by either triaxial type loading system or incremental loading system. The procedures by national or international organizations for compacting specimen of cohesionless soils and cohesionless intermediate geomaterials are to be followed to performing 3-dimensional settlement tests, which shall be about the same as preparing the specimen of cohesionless soils and intermediate geomaterials for triaxial tests.

For the three-dimension consolidation tests to determine the coefficients of consolidation in three-dimensions, horizontal and vertical directions, generally the procedures for testing and other equipment requirements shall be in accordance with ASTM Designation: D2423/D2435M-11 or of other international or national organizations. For three-dimensional settlement test, this standard shall also be followed, except time-period of 24 hours meant for consolidation shall not be applicable. When these tests are performed in triaxial type chamber or sealed reservoirs, the ASTM Designation: D4767-11 or similar standards of other national or international organizations shall be generally followed as far as applicable to these tests for both procedures and equipment requirements.

(c) Installation Details for the Three-dimensional Consolidation Test Device

Three-dimensional consolidation device consists of a flexible ring. Like expandable jacket, the flexible ring also consists of circular arch shaped segmental metal plates, rubber bands or rings and is similarly installed using removable attachment of two half-circular brackets and leather or fabric hook and loop straps. Thickness and width of segmental plates are approximately the same as for expandable jacket. The width and thickness of rubber bands and diameter of elastomeric rubber rings are also about the same. The screw and screw mount sizes in segmental plates and half-circular brackets are about the same as used in the expandable jacket. The installation details are shown in FIG. 14A, FIG. 14B, FIG. 15A and FIG. 15B. The installation details are similar-to installation details of expandable jacket.

The specimens from various depths of a cohesive deposit are obtained by use of Shelby tubes or other type of samplers. The sample shall be extracted from the samplers, in the same manner as is used to extract samples for one-dimensional consolidation test. For the three-dimensional consolidation tests using the flexible ring, there is no need of shaping the specimen or pushing into the fixed ring as is required for the one-dimensional consolidation test. After cutting to the required lengths and leveling the ends of the specimen, the specimen for three-dimensional consolidation test, shall be placed on a filter disc (usually a filter paper disc is used, although a machine woven fabric filter disc can also be used), placed on the bottom porous disc. Bottom porous disc rests on the base plate. Another filter disc is placed on top of the specimen, followed by the top porous disc and the rigid specimen cap. Using a membrane expander, an elastic filter fabric made in the form a cylinder shall be installed around the soil specimen. Using membrane expander, a thick rubber membrane shall be installed around the filter fabric containing the cylindrical specimen. A thicker rubber membrane which can be installed using a membrane expander or other appropriate device, shall have some advantage over thinner membrane as a thick rubber membrane shall keep the cylindrical shape along the joint space between the segment plates. It may be noted that filter fabric is not needed for the test which allows dissipation of excess pore-water pressures only in vertical direction, as shown in FIG. 10A and FIG. 12B.

Figure 14A:
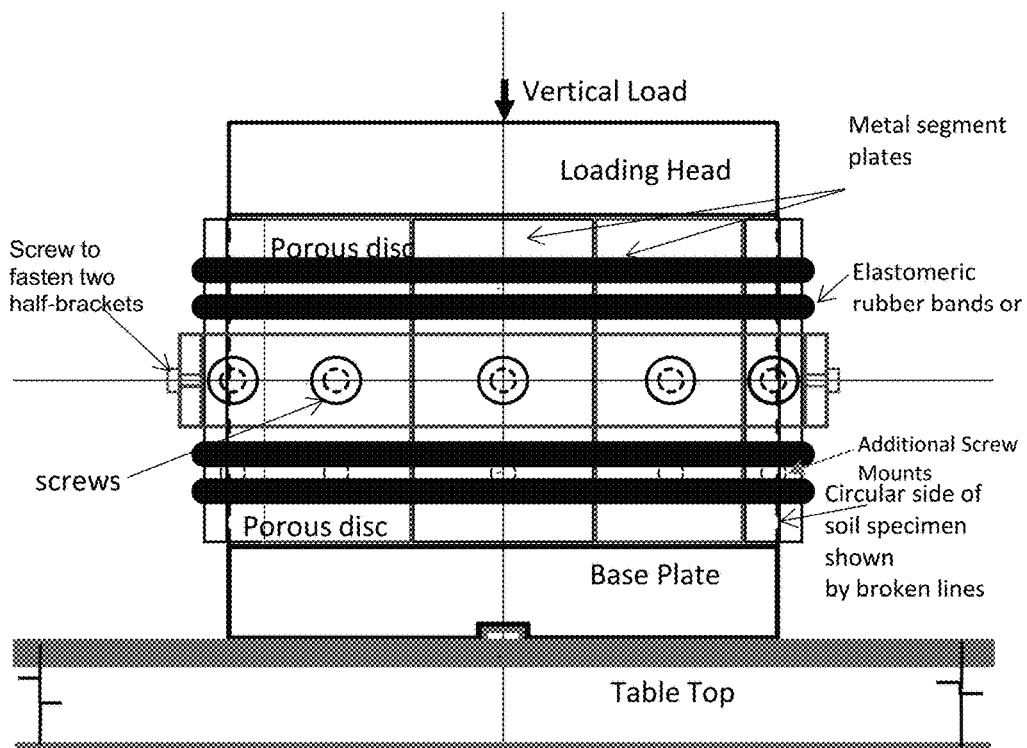
FIG. 14A shows the segmental circular arch shaped metal plates using two half-circular brackets and installed rubber bands or rings.

Commercially available woven or non-woven filter fabric can also be used after stitching it into a cylindrical shape using strips of elastic fabric. Filter fabric can also be wrapped around the soil specimen generally with about ½" (12.7 mm) overlap and maintained stretched or taut in place by a 1" long adhesive tape at the ends. This tape shall be removed after installation of the rubber membrane around the specimen. Thick filter paper can also be wrapped around the cylindrical specimen to provide drainage of excess pore-water leading to porous discs or to open or unsealed reservoir, usually two layers of filter paper when used will provide better drainage. Metal plates (non-corrodible metal segment plates may be preferred for longer design life) are installed around the membrane, using two half-circular metal brackets. Elastomeric rubber bands of generally about 1/8" (3.2 mm) thickness are slipped on around the plates at marked locations as shown in FIG. 14A. The width of rubber bands can vary generally between about 1/8" and 1/2" (3.2 mm and 12.7 mm) or greater. The diameter of elastomeric rubber rings with circular cross-section, when used in place of bands, can vary generally between about 1/16" and 3/8" (between 1.6 and 9.53 mm) or greater. Several threaded holes for screw mounts at one or two heights of the plates in addition to those shown in figures, can also be provided, as needed, in the plates to install the brackets at different heights. For example, as needed, after rubber bands or rings located above a bracket has already been installed, another bracket can be installed near the bottom of the segmented plates, thereafter, the bracket at the middle of the segmented plates can be un-installed, and rubber bands or rings are then installed in the remaining space previously occupied by the upper bracket. The same type of details for segmented plates, threaded holes in plates at various heights, bracket detail and rubber bands and rings shall be used for expandable jackets to be used for the triaxial tests.

Figure 15A:
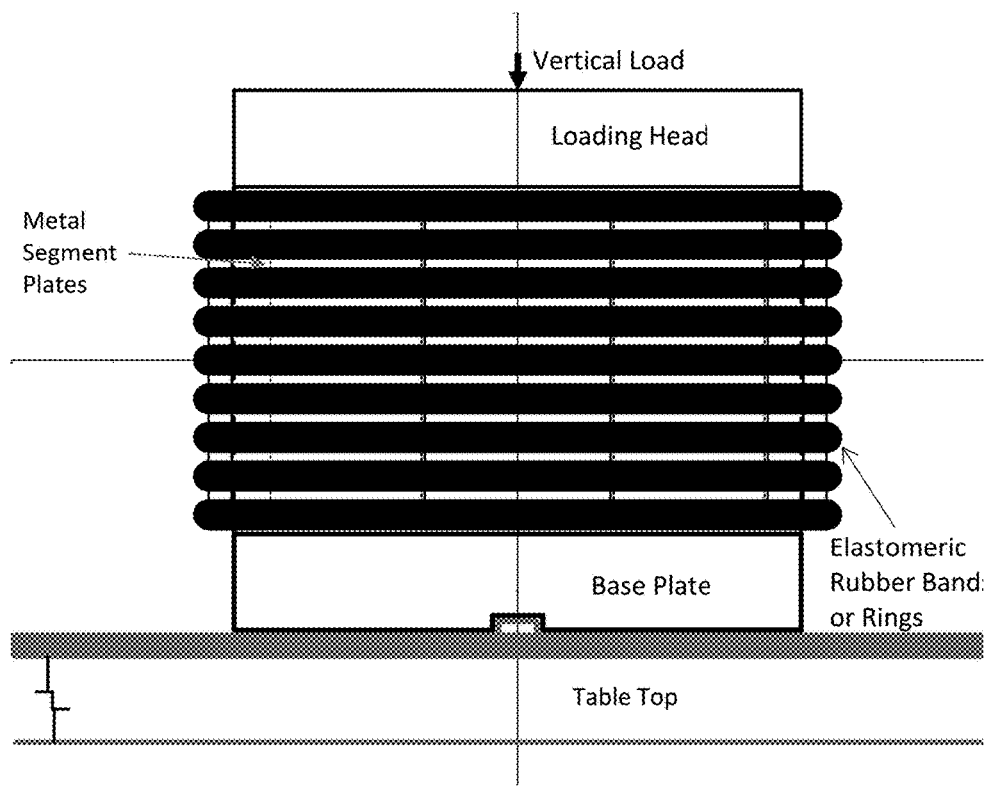
FIG. 15A shows the elevation, when flexible ring has been properly installed surrounding the cylindrical specimen.

The brackets are then un-installed. Remaining rubber bands or rings are slipped on around the plates in the space earlier covered by the bracket, as shown in FIG. 15A. The expandable or flexible ring has thus been installed around the soil specimen. Since segmental circular plates are resting against the top and bottom porous discs or base plate and loading head, initially the lateral load exerted by rubber bands acts on the porous discs and very little, if any, directly on the soil specimen in the beginning of the test. When specimen begins to undergo lateral displacement or lateral expansion during the test, the rubber bands around the segmental plates shall stretch and exert pressure on the segmental plates thereby on the surface of the soil specimen all along its height and shall help in maintaining the uniform diameter through its height during the test; the plates are then not in contact with porous discs and so rubber bands exerts lateral pressure on the specimen. As many rubber bands as needed to maintain uniform diameter of cylindrical specimen and to resist lateral pressures proportional to the applied vertical load during the test, shall be used. The inside surface of segment plates shall be lubricated to reduce friction between rubber membrane around soil specimen and the plates. The function of segmental stainless steel plates is to uniformly distribute the lateral load applied by rubber bands on the soil specimen.

Figure 14B:
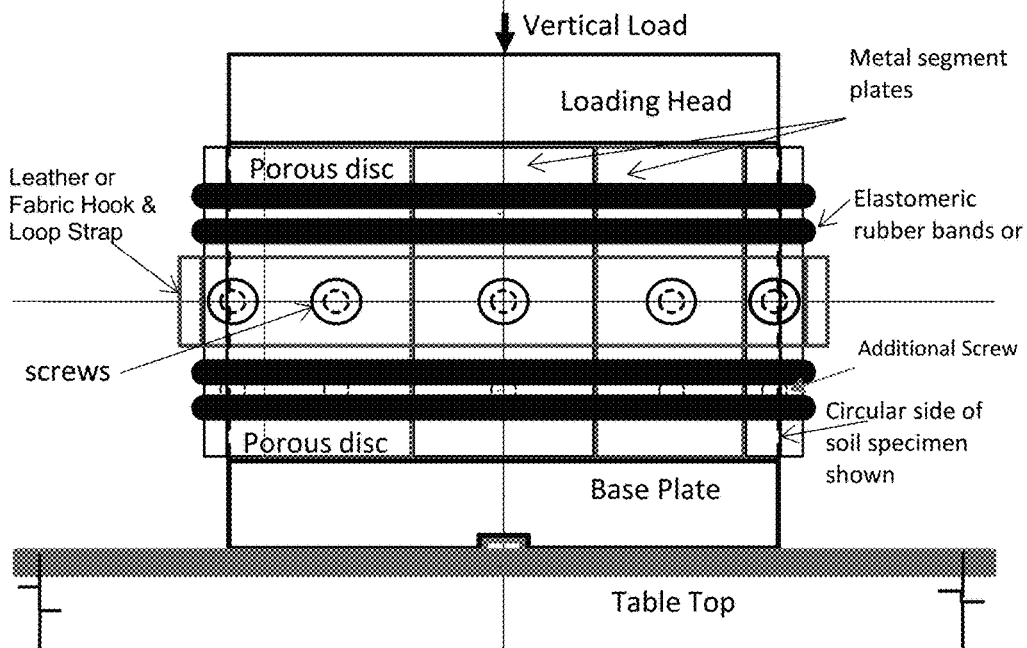
FIG. 14B shows the segmental circular arch shaped metal plates using leather or fabric hook and loop straps and installed rubber bands or rings.

In addition, the lubricated segment plates can be assembled around the cylindrical specimen by use of leather or Fabric hook and loop straps of width generally between about 1/2" and 1" (12.7 mm and 25.4 mm). First, as shown in FIG. 14B, segment plates are fastened to leather or fabric hook and loop strap using appropriate screws (appropriate screw sizes, such as generally ranging from U.S. No. 4 to U.S. No. 14 or their matric equivalent) shall be used along with appropriate female threads in the segment plates. The assembled plates are wrapped around the soil specimen and maintained in position by fabric hook and loop strap as shown in FIG. 14B. The rubber bands of thicknesses of generally varying between about 1/16 and 1/8" (1.61 and 3.17 mm) or greater, are slipped on around the plates as shown in FIG. 14B. The screws are unthreaded to remove the straps. The remaining rubber bands are then slipped on around the plates in the space earlier occupied by the fabric straps, as shown in FIG. 15A. The flexible ring has now been installed around the soil specimen. The metal brackets or leather or fabric straps can also be installed near the bottom of the plates, in addition to one shown at middle of the height in the figure, as considered necessary to properly install the rubber bands or rings.

Figure 15B:
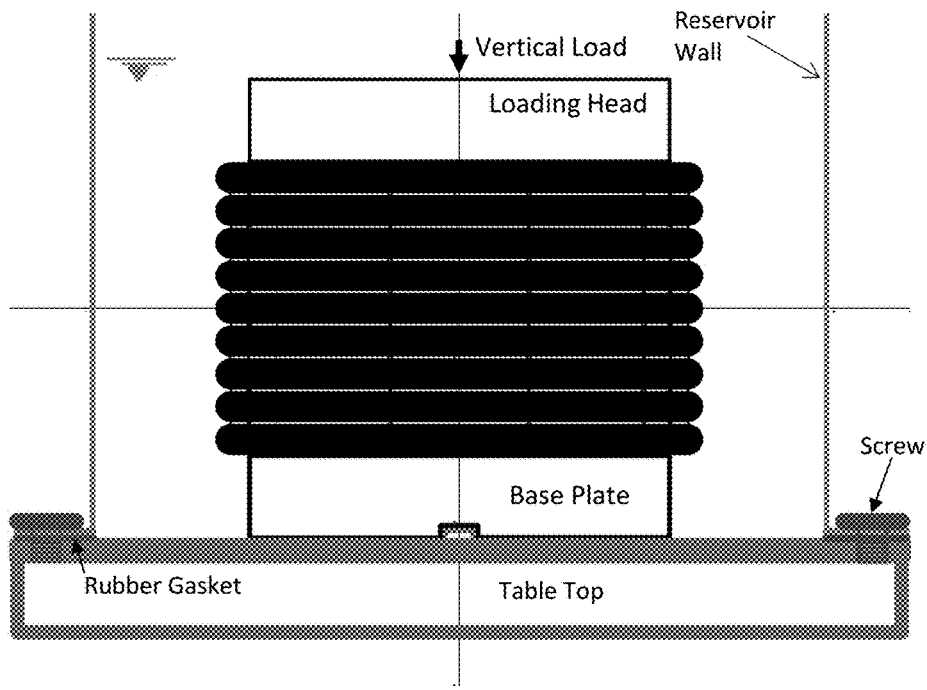
FIG. 15B shows the detail, when reservoir has been placed around the flexible ring containing cylindrical specimen of soils or intermediate geomaterials.
Figure 16A:
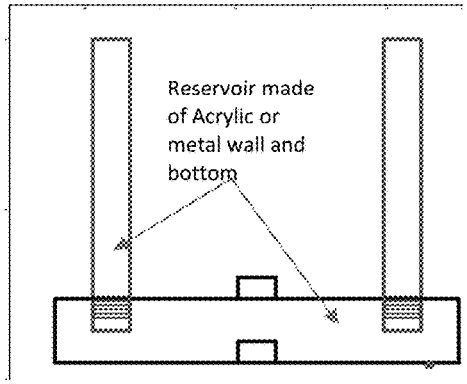
FIG. 16A shows detail of a metal or acrylic open reservoir.
Figure 16B:
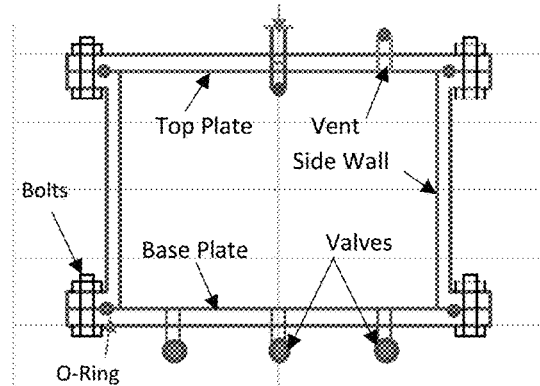
FIG. 16B shows sealed metal reservoir.
Figure 16C:
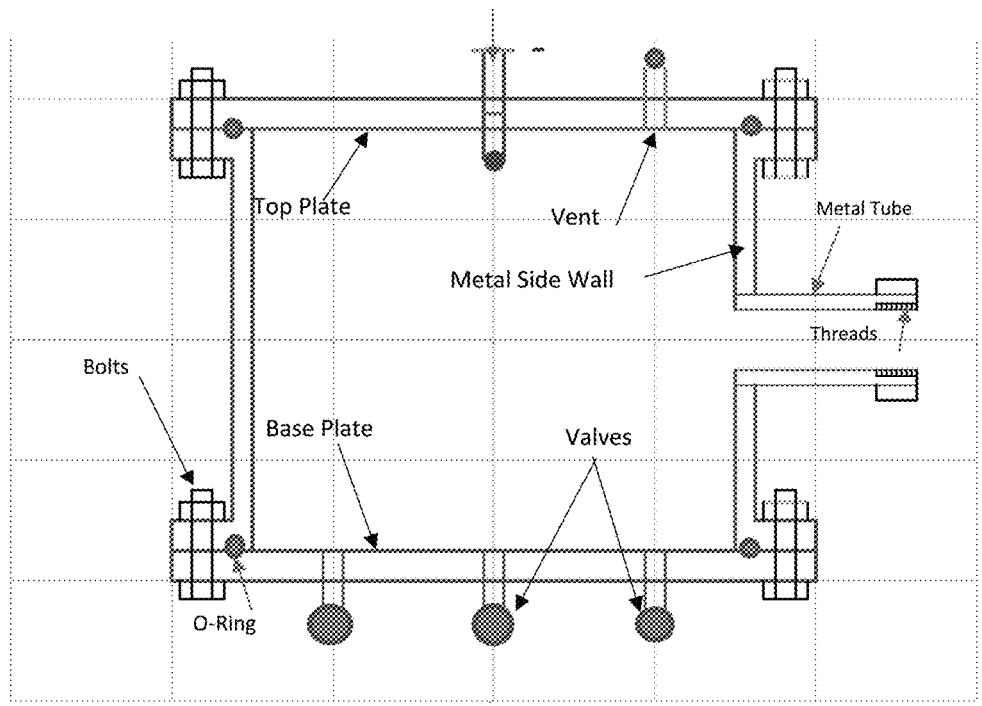
FIG. 16C shows sealed metal reservoir or chamber with weld connected metal tube to receive high pressure sealed LVDT.
Figure 17:
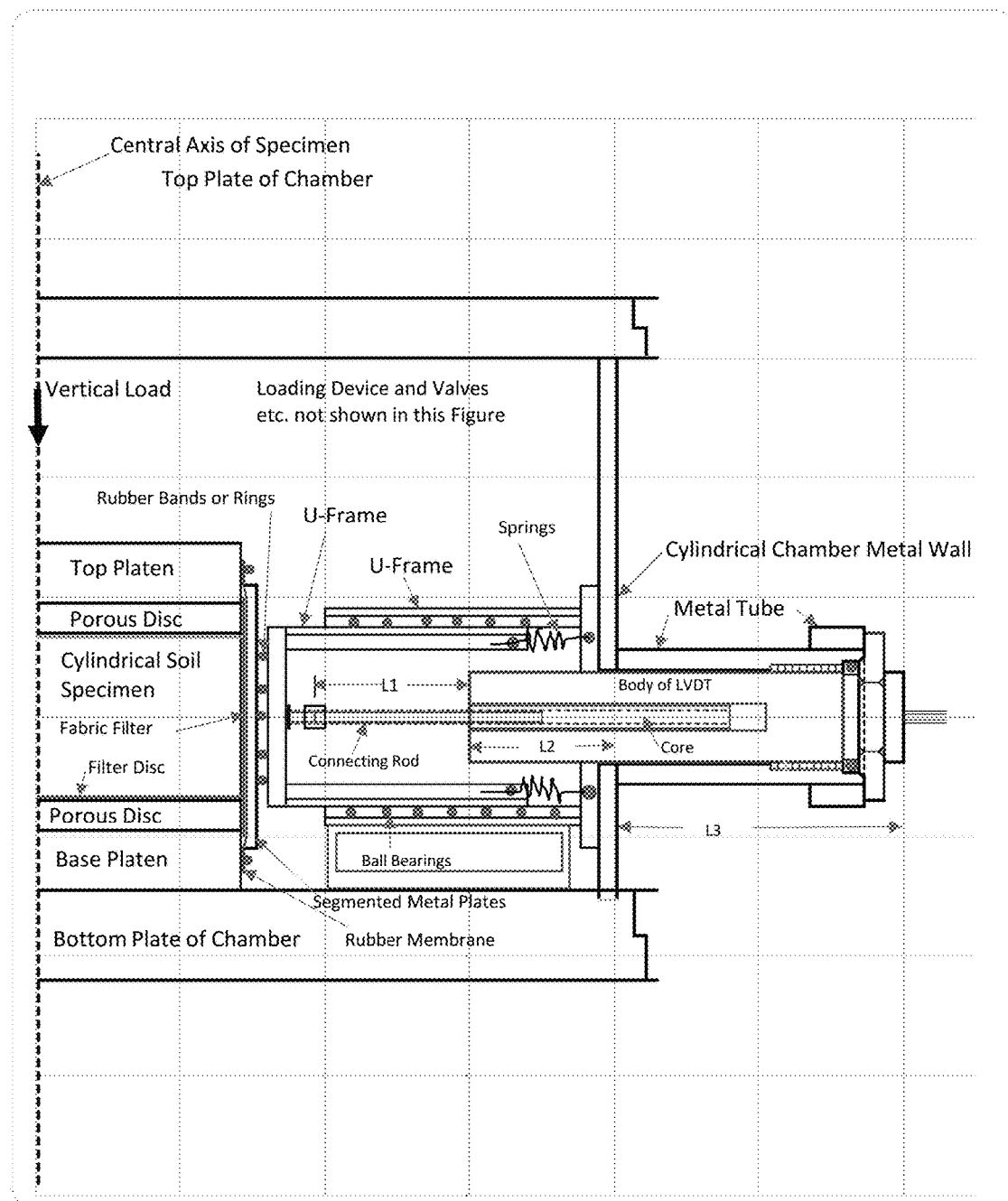
FIG. 17 shows high pressure sealed LVDT attached to the spring-mounted U-frame movable on ball bearings and facing plate in contact with flexible ring.

FIG. 15B and FIG. 16A shows an open reservoir using acrylic or metal cylindrical wall. The reservoir is assembled around the flexible ring containing the cylindrical specimen. FIG. 16B shows a sealed metal chamber which can withstand lateral water pressure up to 150 psi (1034 kPa). For this chamber, first 3-D device shall be assembled on the metal base plate, then the side metal wall shall be installed as shown in this figure and filled with fluid/water, before or after placing the top metal plate. The top metal plate shall then be installed. The O-ring or flat gasket shall seal the base plate and top plate to the cylindrical side walls. The sealed metal reservoir shall be provided with valves and vent valves in a similar arrangement as is conventionally provided with triaxial type chamber. Triaxial type control panel shall be used with the sealed reservoir or triaxial type acrylic or metal chamber. When the measurements of radial expansion by use of high pressure sealed LVDT with axial connector is made, then sealed metal reservoir or triaxial type metal chamber shall be provided with a metal tube weld connected to the cylindrical walls as shown in FIG. 16C and FIG. 17. The schematic detail of the metal reservoir constructed as above, spring mounted U-frame and high pressure sealed LVDT is shown in FIG. 17 for performing three-dimensional consolidation and three-dimensional settlement tests. Since the above type high pressure sealed LVDT can only be used in metal cylindrical walls, as explained in the section for "Mounting Device for LVDT", the hermetically sealed LVDT Position sensors with radial connector shall also be used with triaxial type chamber or sealed reservoir made either acrylic or metal cylindrical wall, for performing three-dimensional consolidation tests. The hermetically sealed (i.e. high pressure sealed) with axial connector and double sealed cable exit as shown in FIG. 18 shall also be used for pressure acrylic or metal chambers and sealed reservoirs. Specially designed sealed cable exit with O-rings from the top plate shall be necessary as sown in FIG. 18.

For open reservoir, although high pressure sealed LVDT with a metal tube weld connected to open metal reservoir (like the one shown for metal chambers) can be used, alternatively, either a hermetically sealed LVDTs with sealed radial connector and with sealed cable exit or without double sealed cable exit, but with cable exit properly sealed by a fused tape or shrink tube can be used successfully. Spring-loaded U-frame shall be required to mount the LVDT in open reservoir. The hermetically sealed LVDTs have coil windings sealed with sealed radial connector, which is perpendicular to the LVDT body, and can pop out of the water of the open reservoir from where cable connector can be attached. Still for additional precaution, a fused tape can be wrapped around the area to make it waterproof where cable connector is attached to the radial connector for protecting against water or moisture.

Two LVDTs, each located diametrically opposite each other can also be provided to have measurements at two locations, although measurement by one LVDT could be considered sufficient. Four LVDTs located 90 degrees apart along the perimeter of the cylindrical specimen can also be provided to get data radial expansion at four locations. If two LVDTs are used, then two metal tubes diametrically opposite to each other shall be provided to install high pressure sealed LVDTs through them.

Sizes of segment plates, half brackets and rubber bands shown in these figures and described in the text above are based on cylindrical specimen of diameter 2.87" (72.9 mm). Diameter of cylindrical specimen is also dependent on the inside diameter of Shelby tubes or other type of samplers used for extracting the samples from a cohesive deposit. The inside diameters of Shelby tubes as per ASTM standards are 1.905" (48.42 mm), 2.87" (72.9 mm) and 4.76" (120.9 mm). The diameter of circular arch shaped segment plates and two half-brackets shall depend on the diameter soil specimen. Number of segment plates shall be generally about 8, 10 and 16 for soil specimen of 1.905" (48.42 mm), 2.87" (72.9 mm) and 4.76" (120.9 mm), respectively. For other specimen sizes, special design detail shall be used.

Metal plates shall be used for circular segment plates and half brackets. Stainless steel, aluminum alloys of certain grades and selected grades of several alloy metals (which do not have tendency to corrode or rust) may be preferred because of longer design life. The thickness of circular segment plates and brackets shall be selected, as considered appropriate and necessary. The selection of type of the metals, thicknesses and widths for circular segment plates and half-brackets shall be based on economics, workability and design life. The circular segmental plastic plates could also be selected in place of metal plates, based on the workability and design life. Screw and bolt sizes (preferably U.S. No. 4 to No. 14 thread sizes or metric equivalents) for expandable jacket and flexible ring shall be selected based on economics, workability and availability in the industry/market. Elastomeric rubber bands and rings both can have either rectangular or square or circular cross-section or cross-section of the shape of even an ellipse. Elastomeric rubber rings or bands (consisting of different types of rubber or rubber composites) with circular or cross-section or other round shapes may prove to be easier to slip on the segment plates, therefore, as an alternative, elastomeric bands or rings with circular or round cross-section or other different cross-sections shall also be used to slip on the segment plates in place of rubber bands or rings with square or rectangular cross-section. The thickness/diameter, modulus of elasticity and the tensile strength of elastomeric rings/bands and their total number shall be selected based on the design lateral resistance to be exerted by the expandable jacket on the cylindrical soil specimen during the test. The specifications as mentioned above may be applied to both expandable jacket and ring.

Fabric is the cloth or other material produced by weaving cotton, nylon, wool, silk, or other threads together. The type of fabric for fabric straps shall be selected based on availability, workability, design life and economics.

(d) Loading Device for Vertical Load

Incremental consolidation load frame/test system shall be the same as described in ASTM D-2435 and AASHTO T-216. The test shall be performed at vertical load increments of ½, 1, 2, 4, 8, 16 or to 32 tsf (Note: 1 tsf=0.09576 MPa). Each load increment shall be maintained for 24 hours and readings taken at intervals described in ASTM D-2435. The test device as shown in FIG. 10A, FIG. 10B, FIG. 11A, FIG. 11B, FIG. 12A, FIG. 12B, FIG. 13A, and FIG. 13B are adaptable to these loading devices. This loading increment method is used to determine the coefficient of consolidation, overburden ratio, maximum preconsolidation pressure, constrained modulus and to develop several consolidation theories based only on coefficient of consolidation in vertical direction, such as charts of the ratio of depth to height of consolidation medium, (i.e. saturated cohesive soil) versus consolidation ratio (Lambe and Whitman, 1969). These charts may become obsolete or unusable for the test results based on the three-dimensional consolidation tests. Even concepts of determining overconsolidation ratio and maximum preconsolidation pressure etc. may also change.

As shown in FIG. 10A, FIG. 10B, and FIG. 11A, the open reservoir containing 3-D consolidation device shall be used with conventional incremental loading device in accordance with ASTM D-2435 or using Triaxial type loading system for performing three-dimensional consolidation tests generally in accordance with ASTM standards or standards of other national organizations. The open or unsealed reservoir system with incremental load system for three-dimensional consolidation tests shall be quite easy to become in practice as geotechnical engineers and technicians are very familiar with this system in US and other countries. A triaxial type chamber system like the one used for triaxial compression tests or sealed reservoir system, shall also be used for performing 3-D consolidation tests as shown in FIG. 11B, FIG. 12A, FIG. 12B, and FIG. 18. The chamber for applying lateral pressure on 3-D consolidation specimen, including axial loading system and control panel, in general shall be in accordance with ASTM Designation D4767-11. Because the height of specimen for 3-D consolidation tests shall be selected between ½" (12.7 mm) and half to three-quarter of the diameter of the soil specimen, the height of chamber to be used for 3-D consolidation test shall be about half or less than half of the height of the triaxial chamber. It may be noted that the height of the soil specimen for triaxial compression tests is generally greater than diameter of specimen and is generally about 2 times the diameter. Using triaxial axial loading system, either (a) the load shall be applied in the same increments as described in the above paragraph and held constant for 24 hours or (b) the strain controlled load test can also be performed, applying load to produce a selected vertical displacement at the beginning of each increment and then load held constant for 24 hours and measuring the consolidation settlement. The chamber system to apply lateral pressure on 3-D consolidation sample can also be used with incremental load frame/test system as shown in FIG. 19. The size of incremental loading system as shown in FIG. 20 is greater than the size of the incremental loading system required for open reservoir system, due to chamber clamping rods. Therefore, the incremental loading system to be used with the chamber system, shall be larger in width and height and shall be designed to accommodate the larger lateral dimension and height of the chamber.

When the 3-D consolidation test is required to be performed in-situ condition (such as in partially saturated condition), system for applying vacuum and performing the back-pressure saturation included in the control panel as shown in FIG. 19 and FIG. 20 shall be omitted. In many cases in the field, 100% saturation of partially saturated soils may never or may rarely occur in the life time of a structure, therefore, 3-D consolidation tests in in-situ moisture conditions may also be important. When, in-situ horizontal stresses are applied in the chamber system, at higher vertical load increments, the air in partially saturated soils either may get expelled out or may get dissolved and 100% saturation may be achieved at higher load increments, and therefore the same test may also provide 3-D consolidation properties, initially in partially saturated conditions and then at higher load increments in 100% saturated conditions. However, if the test is to be performed in 100% saturated conditions, then vacuum and back saturation as shown in control panel shall be used to fully saturate the partially saturated soil specimen.

There are some important advantages of using a chamber system or sealed reservoir system along with incremental consolidation load frame or triaxial axial loading system. In the chamber or sealed reservoir, fluid pressure can be applied equivalent to the insitu horizontal earth pressure calculated for the depth from where the specimen of soils and intermediate geomaterials was extracted for performing the consolidation test. Incremental consolidation load frame or triaxial axial loading system then shall predict both vertical and horizontal settlements of the soil at various values of loads at that depth. If there is a thick soil deposit, and soil specimen have been extracted from various depths, a detailed data of horizontal and vertical settlements at various load increments shall be available at various depths of the same soil deposit. This will also help in providing data of insitu modulus of elasticity of soil at various depths.

In general, the horizontal stresses computed from the theory of elasticity are function of Poisson's ratio. However, vertical stresses resulting from normal stresses applied to the surface are always independent of Poisson's ratio. Vertical and horizontal stresses caused by strip load are also independent of Poisson' ratio (Lambe and Whitman, 1969). Horizontal stresses caused under a circular area depend on Poisson's ratio. Therefore, in three-dimensional consolidation tests, it is important that horizontal stresses caused by vertical stress applied on the specimen be approximately equal to those predicted by theory of elasticity either for strip load or for circular load. In three-dimensional consolidation test, as vertical load is increased, the horizontal resistance on the sample increases as a product of lateral strain in rubber bands/membrane/filter fabric and its modulus of elasticity. Lateral strain during the test is calculated from LVDT measurements of radial expansion or by calculations as described above. Combined modulus of elasticity of rubber bands, rubber membrane and elastic filter fabric is measured by the calibration device at various values of lateral strain. Therefore, ideally or theoretically, the combined modulus of elasticity of rubber bands, rubber membrane and elastic filter fabric during 3-D consolidation test should develop an increase in lateral resistance which should be equal to the increase, estimated to occur in soil by the theory of elasticity at the same increment of the vertical load The various types of elastomeric rubber bands or rings are manufactured and the modulus of elasticity of these types can very between 100 to 800 psi (689 to 5516 kPa). The lateral resistance shall also depend on the thickness, width (or diameter if circular cross-section) and number of elastomeric rubber bands. Therefore, for three-dimensional consolidation tests, it shall be advisable to select the sizes and number of elastomeric rubber bands and their modulus of elasticity with the consideration that the increase in lateral resistance during the 3-D consolidation test is approximately the same as the increases in horizontal stresses in soil predicted by theory of elasticity.

For computer savvy engineers or technicians and those very familiar to electronic measurements and direct recording of the data to the computer, the three-dimensional tests when conducted with LVDT measurements for radial expansion, digital gages for vertical displacement, pore-pressure measurement by electronic piezo-transducers, vertical load by load cells, and other items also by electronic measuring devices shall be very desirable and then they analyze data on computer, and therefore, the option of the LVDT for radial measurement has been kept for three-dimensional consolidation and settlement tests, both for open reservoirs and sealed chambers or triaxial type chambers for all types of soils and intermediate geomaterials whether in 100% saturated or partially saturated state. For engineers and technicians who are not very familiar to electronic measurements, three-dimensional consolidation tests when performed without LVDT measurements for radial expansion, incremental load system or triaxial type load system with proving ring, and dial gage measurement for vertical displacement shall be preferable both for open reservoirs and sealed or triaxial type chambers.

(III) Calibration Device for Expandable Jacket and Flexible Ring

During the test, when an additional vertical load increment is applied, the lateral stress increases which thereby is resisted by the elastomeric rubber bands/rings, rubber membrane and filter fabric. These elastic elements stretch/expand during the test; the magnitude of expansion or increase in diameter is proportional to the lateral load and their modulus of elasticity. The increase in lateral stress for each increment of load shall be dependent up on the vertical stress times Poisson's ratio. The magnitude of the lateral stress cannot be allowed to exceed the tensile strength of these elastic elements. The magnitude of lateral stress is proportional to the vertical stress applied during the test. Therefore, vertical load to be applied during the test should be limited so that the tensile strength of these elements is not exceeded. For this purpose, the vertical load shall not be increased any further, when the rate of increase in diameter as measured by LVDTs increases suddenly, indicating that the failure is approaching. If LVDTs are not used, and when the vertical settlement continues to increase at the same load increment, the vertical load shall not be increased any further and it shall be assumed that tensile strength of elastomeric rubber bands or rings is about to occur.

Figure 21:
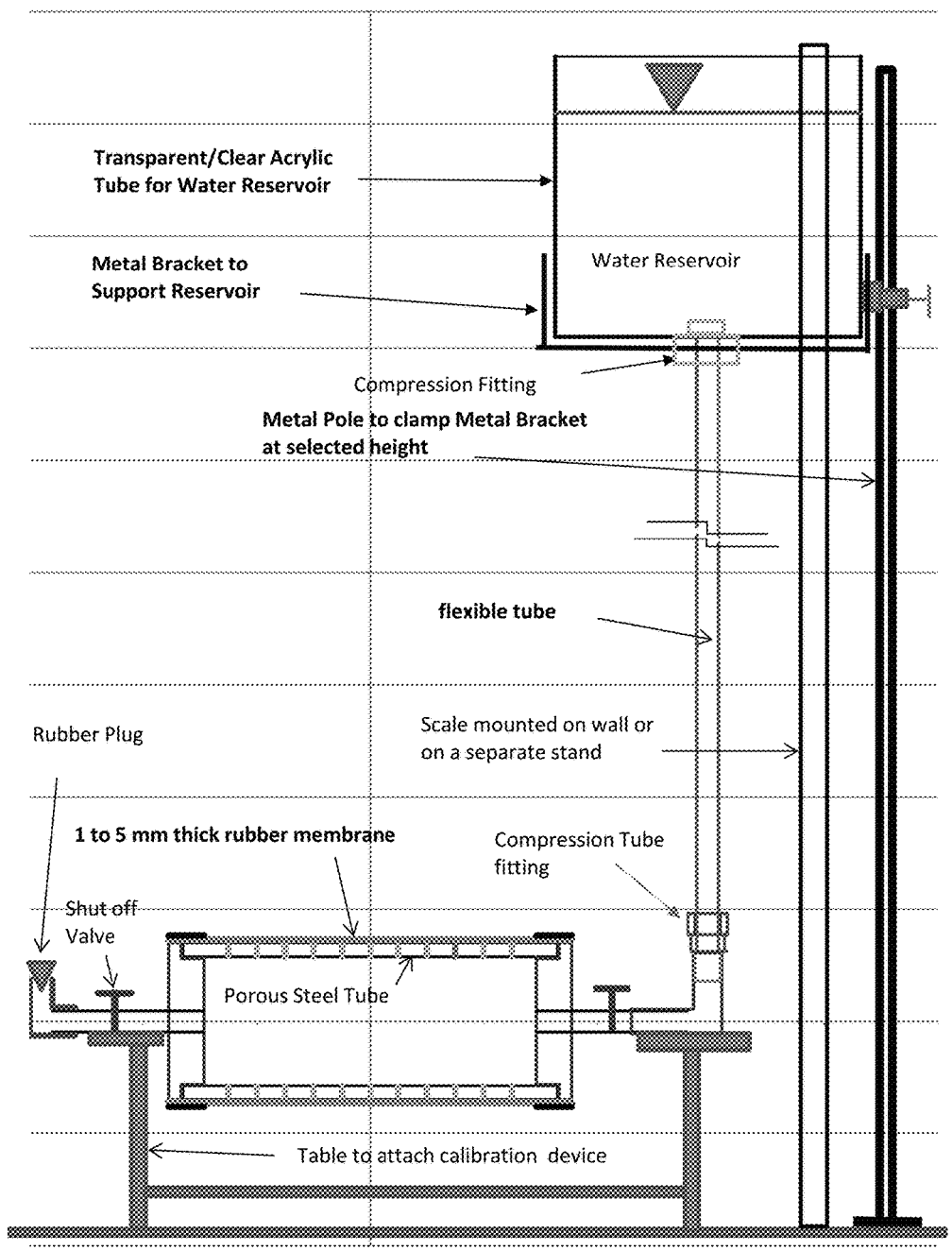
FIG. 21 shows the calibration device for determining the modulus of elasticity of rubber membrane.
Figure 22:
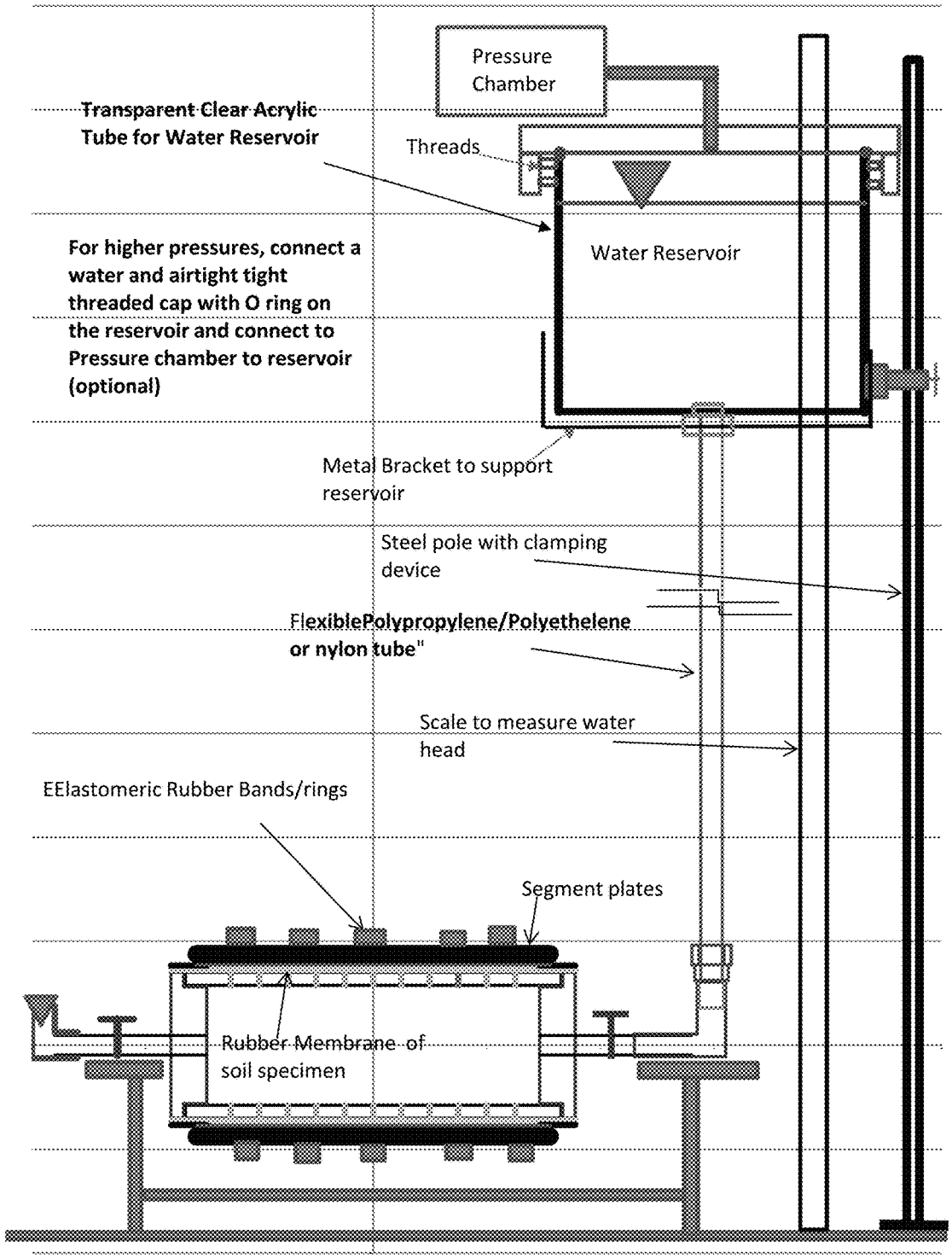
FIG. 22 shows that expandable jacket has been installed on calibration device to perform calibration of the expandable jacket and to determine combined modulus of elasticity of rubber membrane, filter fabric or filter paper, additional rubber membrane, segmental metal plates and rubber bands or rings.

A calibration device as shown in FIG. 21 and FIG. 22 shall be used to provide the data for the magnitude of lateral stress versus the increase in diameter (or lateral strain) of rubber membrane/elastomeric rubber bands/filter fabric. This data shall help in calculating the combined modulus of elasticity of these elastic elements and circular shaped metal segment plates installed around the specimen. The increase in diameter shall be calculated using the measured drop in water reservoir. The transparent clear acrylic cylindrical reservoir, generally about 2" to 8" (50 and 200 mm) in diameter, shall be raised by a foot (0.3 m) or less each time to expand the calibration device as shown in FIG. 21, also when flexible ring is mounted on calibration device as shown in FIG. 22 to provide data of expansion of these elastic elements with increase in water head or hydraulic pressure. The reservoir can be raised to any height varying between 2 and 8 ft. (0.6 and 2.4 m) or to greater height depending on the headroom of the laboratory. If higher pressures are needed for calibration, the water reservoir shall be disconnected and a hydraulic pump of a very low capacity (maximum of 40 psi, i.e., 276 kN/m$^2$) shall be connected to the calibration device to perform the calibration up to about 20 psi (138 kN/m$^2$) pressure. The pressure shall be increased in increments of 0.5 to 1 psi (3.5 to 6.9 kN/m$^2$). Alternatively, if higher pressures are needed for calibration, the water reservoir shall be capped by a water/air tight cap and the reservoir connected to a pressure chamber which is pressurized by a nitrogen cylinder or air compressor and pressures up to 20 psi (138 kN/m²) shall be applied to perform calibration. The pressure shall be applied in increments of 0.5 to 1 psi (3.5 to 6.9 kN/m²). Generally, hydraulic pump system or a pressure chamber shall not be needed as shown in FIG. 22, and therefore this system shall be considered as optional depending up on the needs of the engineer.

The calibration device consists of a porous metal tube (stainless steel or non-corrodible metal tube may be preferred because of longer design life) with end caps sealed for the water tightness. The rubber membrane of thickness between 1 and 5 mm is mounted on porous metal tube. The rubber membrane is clamped at the ends of porous metal tube for the water tightness. On one end, a metal tube (brass or stainless steel tube shall be preferable) shall outlet from the porous metal tube to remove the air bubbles from water when hydraulic fluid is filled in the porous steel tube. When air bubbles are not seen coming out from the tube, the valve shall be closed. On the other end of the porous metal tube, the metal tube (brass or stainless tube shall be preferable) and flexible tube (preferably a polyethylene or nylon tube) shall lead towards the movable reservoir. The thinner rubber membranes can be mounted on each other to make up the required overall thickness of membrane (say between 1 and 5 mm).

The calibration of the calibration device as shown in FIG. 21 shall be first done and data recorded in Table 2. Thereafter, first filter fabric (or filter paper if used around cylindrical specimen during the test), then rubber membrane, (same as to be used during the test around the cylindrical specimen), then segment plates and finally rubber bands shall be mounted on the calibration device. The segment plates shall be mounted with the help of half-brackets or fabric hook and loop straps as previously described. The calibration of the calibration device shall be done by raising reservoir by half a foot (0.15 m) or a foot (0.3 m) or less or by pump pressure or chamber pressure each time by 0.5 psi (3.5 kN/m²). The value of radial displacement shall be calculated using the measured drop of level in the water reservoir. The calibration data shall be recorded in Table 4. The lateral stress exerted by rubber membrane of thickness between 1 and 5 mil (mm) of calibration device shall be deducted from the lateral stress exerted by the rubber membrane of calibration device plus the additional rubber membrane (of thickness between 0.5 mm and 5 mm), which was wrapped around the cylindrical specimen during the test, filter fabric and rubber bands. This data shall help in determining the value of lateral stress being exerted on the flexible ring or expandable jacket during the test. The calibration data shall also be used to calculate the combined modulus of elasticity of these elastic elements and segmented circular shaped metal plates. For the test method shown in FIG. 10A and FIG. 13A, the calibration shall be done on the flexible ring consisting of the two rubber membranes, segment plates and rubber bands, without fabric filter or filter paper. The product of lateral strain with combined modulus of elasticity of the flexible ring or expandable jacket shall provide the value of lateral stress at any instant of time during application of the vertical load during the test.

There is a limit for the vertical load which can be applied during the test, as explained above, this limit shall depend on the tensile strength of the elastomeric rubber bands. For higher vertical load, the elastomeric rubber bands shall be replaced by a jacket consisting of stainless steel or non-corrodible metal springs, which can stretch and resist vertical loads up to 32 tsf (3.06 MPa). In this case, calibration shall be done for the spring jacket in place of elastomeric rubber bands.

CONCLUSIONS (I) Invention of the Expandable Jacket (1) The invention of expandable jacket included in this application shall maintain the cylindrical shape of the soil specimen during the triaxial compression test. For more than 100 years, the main criticism of the triaxial compression test has been that the cylindrical shape becomes barrel shape with localized bulging during the test. With the invention of the expandable jacket; this criticism for more than 100 years, which has not been resolved so far, shall be completely overcome and the cylindrical shape of the specimen with uniform increase in diameter shall be maintained as is necessary to perform an accurate triaxial test. The expandable jacket included in this invention consists of circular segmental metal plates wrapped around the rubber membrane surrounding the cylindrical specimen and elastomeric rubber bands or rings surrounding the segmental plates to permit the uniform radial expansion and maintain the uniform diameter of the specimen during the test, and thereby providing accurate values of deviator stress, volume change characteristics and shear strength of the cylindrical specimen of soils, intermediate geomaterials and soft rocks. The removable attachments consisting of two metal half-circular brackets, leather or fabric hook and loop straps at various predetermined heights of segmented circular metal plates are used to assemble the expandable jacket. The calibration device for the calibration of the expandable jacket as included in this invention shall accurately quantify the additional lateral stress exerted by the expandable jacket on the cylindrical soil specimen during the test, thus providing the magnitude of correction to be made in the deviator stress.

(2) The radial expansion of the cylindrical specimen of the saturated soils can be calculated by measuring the pore-water expelled out from the specimen and collected in the burette, without requiring the LVDT measurements of radial expansion. This will allow determination of accurate values of deviator stress, shear strength, volume change characteristics and Poisson's ratio.

(3) The radial expansion of the cylindrical specimen of the partially saturated or dry soils can be approximately calculated using the assumed value of Poisson's ratio and the measured vertical displacement of the specimen, without requiring the LVDT measurements of radial expansion. This method shall be useful for the site laboratories where engineers or technicians are not very familiar in using the LVDT measurements. This system shall also help in reducing the cost of equipment.

(4) For accurate measurements of the uniform radial expansion of the cylindrical specimen of dry or partially saturated soils, LVDTs mounted on the spring-loaded U-frame moving on the ball bearings shall be used. Vertical displacement accompanying the radial expansion has a tendency of bending the LVDT probe damaging it, but the use of the mounting device using spring-loaded U-frame prevents damage of the LVDT probe.

(5) For computer savvy engineers and technicians who are familiar to electronic instruments, the use of LVDT for measurement of radial expansion for all types of soils and intermediate geomaterials, when expandable jacket is used, load cell for vertical load measurement, electronic pressure transducer for lateral pressure in the chamber, electronic piezometer cell for pore pressure measurements, electronic gages for measurements of vertical displacements, electronic reading and recording system of the data connected to a computer will have great advantages as data is analyzed without necessity of hand recorded readings. But for engineers and technicians not familiar with electronic measurements, the triaxial compression test without LVDT measurements but with expandable jacket shall be performed and the radial expansion shall be calculated based on pore-water expelled out from the cylindrical specimen and measured in the burette or based on the assumed value of Poisson's ratio.

(6) When core and LVDT body system is used, which are not spring loaded, the spring-loaded U-frames keeps the LVDT core in initial and subsequent positions properly during the linear lateral expansion. For use in pressure chambers or sealed reservoirs, the specially designed high pressure sealed LVDTs with core (without spring-loaded system) are also used.

(7) Either high pressure sealed LVDT which exit axially from the cylindrical metal wall or hermetically sealed LVDT with radial connector, which exit from the top metal plate of the acrylic or metal cylindrical wall shall be used for measuring the radial expansion of the cylindrical specimen during the test, when considered necessary. These are only two cases, similar designs for sealed cable exit shall be required for other sealed LVDTs as available in the industry from time to time, but those could be different than shown in figures and describe in the text.

(8) For maintaining the uniform radial expansion during unconfined compression and uniaxial compression strength of the cohesive soil samples or soft rocks, the expandable jacket shall be used. The LVDTs consisting of either core and body system or spring-loaded LVDT system shall be used when mounted on spring-loaded U-frame, to measure the radial expansion. Use of LVDT measurements shall provide accurate values of the strengths and Poisson's ratio. Without using LVDT, the tests can be done using the expandable jacket, but the value of strengths will be not exact, but approximate, but still quite useful and reasonable for design purposes.

(9) For determining the Poisson's ratio of the concrete cores and intact rock cores, the expandable jacket shall not be used, but LVDT measurement with use of the spring-loaded U-frame shall be used.

(10) When using a spring-loaded LVDTs, the use of spring loaded U-frame moving on ball bearings becomes optional, as the U-frame without attachment of springs moving on ball bearings can also be used, but guided core LVDTs, the spring-loaded U-frame will be necessary. However, the spring-loaded U-frame shall be preferable with spring loaded LVDTs to provide double precaution that both LVDT and U-frame maintain proper position before, during and after measurements.

(11) For determination of the pore air and pore-water pressures developed in the embankment consisting crushed and broken rock fills, the use of both expandable jacket and LVDT measurements becomes very important. The Mohr's failure envelop can then be developed accurately and present models of the Mohr's failure envelop can be considerably improved. The stability analyses for earth dam embankments at various stages of the height of embankment during construction and reservoir filling at various heights, where pore-water and pore-air pressures develop can be accurately performed, when analyzed data using the expanded jacket and LVDT measured data is used.

(II) Invention of the Flexible Ring (1) The flexible ring is like the expandable jacket and the structural components that make the flexible ring are also like that of the expandable ring, with same type of the removable attachments, however its purpose is to devise a test system for performing three-dimensional consolidation and three-dimensional settlement tests of soils and intermediate geomaterials. The height of the flexible ring is selected based on the height of cylindrical specimen, which is generally between about ½" (12.7 mm) and ¾$^{th}$ of the diameter of the cylindrical specimen. (2) Three-dimensional consolidation device for determining the three-dimensional coefficient of consolidation consists of the flexible ring. The flexible ring consists of filter fabric or filter paper around the soil specimen, rubber membrane around the filter fabric or filter paper, circular segmental plates around the membrane and elastomeric rubber bands or rings or spring loaded jacket around the segmental plates to allow both horizontal and vertical displacements, dissipation of excess pore-water pressures in both horizontal and vertical directions, and increased lateral resistance with each increment of vertical load, as occurs in subsurface soils when vertical load is incrementally applied. In open reservoirs, the lateral pressures cannot be applied, so the test is to be performed in the conventional way. The cylindrical specimen rests on bottom porous disc with filter disc in between the porous disc and the bottom of the cylindrical specimen and similarly a filter disc in between the top of cylindrical specimen and the top porous disc. In the sealed triaxial type chambers/sealed reservoirs, the lateral fluid pressure is approximately equal to the insitu horizontal earth pressure, theoretically calculated at the depth from where the soil sample was extracted. In this way, insitu conditions are maintained in the chamber and sealed reservoir, to simulate the insitu condition and environment in the geotechnical laboratories. When open reservoir is used, the filter fabric surrounding the cylindrical specimen protrudes out of the rubber membrane to let the excess pore-water flow out through the filter fabric to the open reservoir, but when triaxial type chamber/sealed reservoir is used, the fabric filter remains inside the rubber membrane to let the excess pore-water flow to the porous discs through the filter fabric, from porous discs, excess pore-water flows to the burette of the control panel for measurement.

(3) The mounting device for LVDT consisting of a spring-loaded U-frame resting on the ball bearings, is placed between the flexible ring containing cylindrical specimen and inside surface of the wall of the chamber/sealed reservoir or the open reservoir and is properly supported on the base plate of the chamber/sealed reservoir or open reservoir. The U-frame shall allow horizontal displacement to be measured by LVDT or strain gages, without allowing bending of the LVDT probe or strain gage, which may otherwise occur due to vertical displacement simultaneously occurring with radial expansion. The lateral or radial expansion of the soil specimen during the test shall be measured by the LVDT or strain gage. If the LVDT or strain gage is not used, the lateral or radial expansion of the cylindrical specimen shall be calculated using the measured vertical settlement of the specimen and the measured amount of pore-water expelled out from the fully saturated specimen to the burette during the test, when the triaxial type control panel with triaxial type chamber/sealed reservoir is used; however when open reservoir is used, then the approximate value of the radial expansion shall be calculated as a product of vertical strain (i.e. ratio of vertical displacement with height of the specimen) with Poisson's ratio of the soil or intermediate geomaterials and the diameter of the specimen. For partially saturated soils, when tests are conducted in triaxial type chamber/sealed reservoir or in the open reservoir, the approximate value of radial strain shall be calculated as above based on Poisson's ratio.

(4) The three-dimensional consolidation device for determining the coefficient of consolidation in horizontal direction, but allowing horizontal and vertical displacement to occur is like that of the device to determine the three-dimensional coefficient of consolidation except that top and bottom porous discs are not used and the cylindrical specimen rests between the top and bottom platens with or without a filter disc in between the platens and the specimen.

(5) The three-dimensional consolidation device for determining the coefficient of consolidation in vertical direction, but allowing horizontal and vertical displacement to occur is like that of the device to determine the three-dimensional coefficient of consolidation except that the filter fabric surrounding the cylindrical specimen is not used and the rubber membrane surrounds the cylindrical specimen. The excess pore-water then can only flow out from top and bottom porous discs, then to the burette in the control panel for measurement.

(6) The test device for determining three-dimensional settlement characteristics of those soils and intermediate geomaterials, which do not generate excess pore-water pressures or which dissipate as soon as they develop, is like the test device for three-dimensional consolidation test device for determining the coefficient of consolidation in vertical direction when placed either in triaxial type chamber/sealed reservoir. This test device shall simulate horizontal and vertical settlements, which take when a vertical load is applied at any depth in insitu conditions.

(7) When tests are conducted on cylindrical specimen extracted from various depth of a soil deposit, the correlations between coefficients of consolidation in three-dimension, horizontal direction and vertical direction with various depths or overburden effective stress, correlations between the ratio of coefficients of consolidation with coefficients of consolidation or with three-dimensional coefficient of consolidation, correlations between modulus of elasticity with effective overburden stress can be developed for use in design.

(8) Either high pressure sealed LVDT with axial connector which exit axially from the cylindrical metal wall or hermetically sealed LVDT with radial connector (perpendicular to the body of LVDT), which exit from the top metal plate of the acrylic or metal cylindrical wall shall be used for measuring the radial expansion of the cylindrical specimen during the test, when considered necessary. These are only two cases, similar designs for sealed cable exit shall be required for other sealed LVDTs as available in the industry from time to time, but those could be different than shown in figures and described in the text.

(III) Removable Attachments to Assemble Expandable Jacket or Flexible Ring Around the Cylindrical Specimen (1) At least two horizontal separate half-circular metal brackets, at least one horizontal fabric hook and loop straps, or at least one horizontal leather hook and loop straps for vertical positioning of each of the segmented metal plates; wherein the circular shaped metal plates are vertically assembled and screwed to brackets or leather or fabric hook and loop straps by screw mounts at two or more predetermined heights of each of the segmented metal plates and wherein elastomeric rubber bands or rings placed such that each of the elastomeric rubber bands or rings surround and are in contact with each of the segmented metal plates; wherein after installation of the segmental metal plates and elastomeric rubber bands or rings, the attachments consisting of brackets and straps are removed.

(IV) A Calibration Device for Determining a Modulus of Elasticity of the Rubber Membrane Surrounding the Porous Metal Tube, the Calibration Device Comprising:

(1) A water reservoir, wherein the water reservoir has a vertical position defined by a vertically movable metal bracket;

(2) A horizontal porous metal tube connected to the vertically movable water reservoir via at least one tube, wherein the porous metal tube is configured to be surrounded and sealed by a rubber membrane.

(V) A Calibration Device for Determining a Combined Modulus of Elasticity of the Rubber Membrane, the Segmented Metal Plates, and the Rubber Bands or Rings, the Calibration Device Comprising:

(1) A water reservoir, wherein the water reservoir has a vertical position defined by a vertically movable metal bracket;

(2) A horizontal porous metal tube connected to the vertically movable water reservoir via at least one tube, wherein the porous metal tube is configured to be surrounded and sealed by an additional rubber membrane and wherein the additional rubber membrane is configured to be surrounded by a combination of the rubber membrane, the segmental metal plates, and the at least one elastomeric rubber band or ring.

TABLE 1

Calculations for lateral stress exerted by rubber bands during the test for sand specimen with Poisson's ratio of 0.3, H = 5.6", d = 2.8", E of Rubber = 100 psi.

| Axial Strain $(\epsilon_v) =$ $(\Delta H/H) * 100$ % | Axial Displacement $(\Delta H) =$ $\epsilon_v * H/100$ inches | Lateral Strain $(\epsilon_l) = \nu * \epsilon_v$ % | Increase in radius of specimen, $\Delta r$ inches | Height near ends in which load distribution shall occur, $\Delta h = 2 * \Delta r$ inches | Lateral stress exerted by rubber bands and membrane = $E * \epsilon_l$ psi |
|---|---|---|---|---|---|
| 1 | 0.056 | 0.3 | 0.0042 | 0.0084 | 0.3 |
| 2 | 0.112 | 0.6 | 0.0084 | 0.0168 | 0.6 |
| 3 | 0.168 | 0.9 | 0.0126 | 0.0252 | 0.9 |
| 4 | 0.224 | 1.2 | 0.0168 | 0.0336 | 1.2 |
| 5 | 0.28 | 1.5 | 0.021 | 0.042 | 1.5 |
| 6 | 0.336 | 1.8 | 0.0252 | 0.0504 | 1.8 |
| 7 | 0.392 | 2.1 | 0.0294 | 0.0588 | 2.1 |
| 8 | 0.448 | 2.4 | 0.0336 | 0.0672 | 2.4 |
| 9 | 0.504 | 2.7 | 0.0378 | 0.0756 | 2.7 |
| 10 | 0.56 | 3 | 0.042 | 0.084 | 3 |

TABLE 1-continued

Calculations for lateral stress exerted by rubber bands during the test for sand specimen with Poisson's ratio of 0.3, H = 5.6", d = 2.8", E of Rubber = 100 psi.

| Axial Strain ($\epsilon_v$) = ($\Delta$H/H) * 100 % | Axial Displacement ($\Delta$H) = $\epsilon_v$ * H/100 inches | Lateral Strain ($\epsilon_l$) = v * $\epsilon_v$ % | Increase in radius of specimen, $\Delta$r inches | Height near ends in which load distribution shall occur, $\Delta$h = 2 * $\Delta$r inches | Lateral stress exerted by rubber bands and membrane = E * $\epsilon_l$ psi |
|---|---|---|---|---|---|
| 15 | 0.84 | 4.5 | 0.063 | 0.126 | 4.5 |
| 20 | 1.12 | 6 | 0.084 | 0.168 | 6 |

TABLE 2

Calculations for lateral stress exerted by rubber bands during the test for specimen of saturated clay with Poisson's ratio of 0.5, H = 5.6", d = 2.8", E = 100 psi.

| Axial Strain ($\epsilon_v$) = ($\Delta$H/H) * 100 % | Axial Displacement ($\Delta$H) = $\epsilon_v$ * H/100 inches | Lateral Strain ($\epsilon_l$) = v * $\epsilon_v$ % | Increase in radius of specimen, $\Delta$r inches | Height near ends in which load distribution shall occur, $\Delta$h = 2 * $\Delta$r inches | Lateral stress exerted by rubber bands and membrane = E * $\epsilon_l$ psi |
|---|---|---|---|---|---|
| 1 | 0.056 | 0.5 | 0.007 | 0.014 | 0.5 |
| 2 | 0.112 | 1 | 0.014 | 0.028 | 1 |
| 3 | 0.168 | 1.5 | 0.021 | 0.042 | 1.5 |
| 4 | 0.224 | 2 | 0.028 | 0.056 | 2 |
| 5 | 0.28 | 2.5 | 0.035 | 0.07 | 2.5 |
| 6 | 0.336 | 3 | 0.042 | 0.084 | 3 |
| 7 | 0.392 | 3.5 | 0.049 | 0.098 | 3.5 |
| 8 | 0.448 | 4 | 0.056 | 0.112 | 4 |
| 9 | 0.504 | 4.5 | 0.063 | 0.126 | 4.5 |
| 10 | 0.56 | 5 | 0.07 | 0.14 | 5 |
| 15 | 0.84 | 7.5 | 0.105 | 0.21 | 7.5 |
| 20 | 1.12 | 10 | 0.14 | 0.28 | 10 |

TABLE 3

Form for entering data to calibrate the calibration device

| Serial No. | Height of Water Level in Reservoir above Centerline of Porous Stainless Steel Tube (ft or m) | Water Level in Reservoir (inch or mm) | Drop ($\Delta$h) in Level of Reservoir (inch or mm) | Increase in Diameter of membrane, $\Delta$d (inch or mm) | Lateral Strain, $\epsilon_l$ = $\Delta$d/d | Water Pressure ($p_w$) in psi (kg/mm$^2$) | Modulus of Elasticity (E) of rubber In psi or kg/mm$^2$ |
|---|---|---|---|---|---|---|---|
| | 0.5 ft (0.150 m) | ... | | | | | |
| | 1 ft (0.305 m) | ... | ... | ... | ... | ... | ... |
| | 2 ft (0.61 m) | | | | | | |
| | 3 ft (0.914 m) | | | | | | |
| | 4 ft (1.219 m) | | | | | | |
| | 5 ft (1.524 m) | | | | | | |
| | 6 ft (1.829 m) | | | | | | |
| | 7 ft (2.134 m) | | | | | | |
| | 8 ft (2.438 m) | | | | | | |
| | 9 ft (2.743 m) | | | | | | |
| | 10 ft (3.048 m) | | | | | | |

Outside diameter of porous stainless tube with 3 mil thick rubber membrane, d = ...,
Length of 3 mil thick rubber membrane between end clamps, L = ...
Cross-sectional Area of device, A = $\pi$ d$^2$/4, Volume of device = A * L
Inside diameter of reservoir = d$_r$, Cross-sectional Area of reservoir, A$_r$ = $\pi$ d$_r^2$/4
Increase in Diameter of device, $\Delta$d, after raising reservoir = [(d$^2$ + 4 * A$_r$ * $\Delta$h/($\pi$ * L)]$^{0.5}$ − d
E of rubber membrane = p$_w$/$\epsilon_l$

TABLE 4

Form for entering data to calibrate the expandable jacket

| Serial No. | Height of Water Level in Reservoir from Centerline of Porous Stainless Steel Tube (ft or m) | Water Level in Reservoir (inch or mm) | Drop ($\Delta h$) in Level of Reservoir (inch or mm) | Increase in Diameter of rubber bands, $\Delta d$ (inch or mm) | Lateral Strain, $\epsilon_{rb} = \Delta d/d_p$ | Water Pressure ($p_w$) in psi (kg/m$^2$) | Modulus of Elasticity (E) of rubber In psi or kg/m$^2$ |
|---|---|---|---|---|---|---|---|
| | 0.5 ft (0.150 m) | | | | | | |
| | 1 ft (0.305 m) | ... | ... | ... | ... | ... | ... |
| | 2 ft (0.61 m) | | | | | | |
| | 3 ft (0.914 m) | | | | | | |
| | 4 ft (1.219 m) | | | | | | |
| | 5 ft (1.524 m) | | | | | | |
| | 6 ft (1.829 m) | | | | | | |
| | 7 ft (2.134 m) | | | | | | |
| | 8 ft (2.438 m) | | | | | | |
| | 9 ft (2.743 m) | | | | | | |
| | 10 ft (3.048 m) | | | | | | |

Outside diameter of porous stainless tube with 3 mil thick rubber membrane, d = . . . ,
Length of 3 mils thick rubber membrane between end clamps, L = . . .
Cross-sectional Area of device, $A = \pi d^2/4$, Volume of device = A * L
Inside diameter of reservoir = $d_r$, Cross-sectional Area of reservoir, $A_r = \pi d_r^2/4$
Increase in Diameter of device, $\Delta d$, after raising reservoir = $[(d^2 + 4 * A_r * \Delta h/(A * L)]^{0.5} - d$
Outside diameter of segmental plates before beginning of test = $d_p$
Rubber bands shall also increase in diameter by $\Delta d$, Lateral strain, $\epsilon_{rb} = \Delta d/d_p$
E of rubber membrane = $pw/\epsilon_{rb}$

REFERENCES

ASTM Standards (2007), Standard Test Methods for Unconsolidated-Undrained Triaxial Compression Tests on Cohesive Soils. ASTM D2850-03, *American Society of Materials*, Philadelphia, Pa.

ASTM Standards (2011), Standard Test Methods for Consolidated-Undrained Triaxial Compression Tests on Cohesive Soils. ASTM D4767-11, *American Society of Materials*, Philadelphia, Pa.

AASHTO (2012), Standard Method of Test for One-Dimensional Consolidation Properties of Soils, *American Association of State Highway and Transportation Officials*, Washington, D.C.

ASTM Standards (2011), Standard Test Method for Determining One-Dimensional Consolidation Properties of Soils, ASTM D2435/D2435 M-11, *American Society of Materials*, Philadelphia, Pa.

ASTM Standards (2011) Standard Test Method for Consolidated Undrained Triaxial Compression Test for Cohesive Soils. ASTM: D4767-11.

Bishop, A. W. and Green, G. E. (1965). "The influence of end restraint on the compression strength of a cohesionless soil," Geotechnique, Vol. 15, pp. 243-266.

Fang, H (1990), Foundation Engineering Handbook, 2$^{nd}$ Edition, *Van Nostrand Reinhold*, New York.

Fredlund, D. G., Rahardo, H., and Fredlund, M. D. (2012). Unsaturated Soil Mechanics in Engineering Practice, Wiley, New York.

Gupta, R. C. (2002 a). "Finite strain analysis for expansion of cavities in granular soils," *Soils and Foundations*, Vol. 42, No. 6, pp. 105-115.

Gupta, R. C. (2002 b). "Estimating bearing capacity factors and cone tip resistance," *Soils and foundations*, Vol. 42, no. 6, pp.117-127.

Gupta, R. C. (2016). "Expandable Jacket and Its Calibration Device for Triaxial Tests on Soils," U.S. Pat. No. 9,383,346 B2, United States Patent and Trademark Office, Alexandria, Va. 22313.

Gupta, R. C. (2016). "Test Device for Determining Three-dimensional Consolidation Properties of Soils," U.S. Pat. No. 9,567,722 B2, United States Patent and Trademark Office, Alexandria, Va. 22313.

Gupta, R. C. (2016). "Test Device for Determining Three-dimensional Consolidation Properties of Soils," U.S. Pat. No. 9,546,940 B2, United States Patent and Trademark Office, Alexandria, Va. 22313.

Gupta, R. C. (2016). "Expandable Jacket and Its Calibration Device for Triaxial Tests on Soils," Publication No. WO 2016/196734, The International Bureau of WIPO, Geneva-20, Switzerland.

Gupta, R. C. (2016). "Test Device for Determining Three-dimensional Consolidation Properties of Soils," Publication No. WO 2016/149128, The International Bureau of WIPO, Geneva-20, Switzerland.

Hilf, J. W. (1956). An investigation of Pore-Water Pressures in Compacted Cohesive Soils," Technical Memorandum No. 650, Bureau of Reclamation, United States of Interior, Denver, Colo.

HRB (1973), Estimating Consolidation Settlements of Shallow Foundations on Overconsolidated Clay, Application Bulletin prepared by Committee A2L02, *Properties of Soli and Rock, Highway Research Board*, Washington, D.C.

Lee, K. L. (1978). "End restraint effects on undrained static triaxial strength of sand," *Journal of Geotechnical Engineering Division*, Vol. 104, pp. 687-703.

Manglik, V. M., and Gupta, R. C. (1977). "Pore Pressures and Displacements in Ramganga Dam," *Indian Geotechnical Journal*, Vol. VII, No. 2, pp. 116-160.

Perloff, W. H., and Baron, W. (1976), SOIL MECHANICS, John Wiley and Sons, New York.

Rochelle, P. L., Leroueil, S., Trak, B., Blais-Lerox, L., and Tavenas, F. (1988). "Observational approach to membrane and area corrections in triaxial tests," Advanced Triaxial Testing of Soil and Rock, ASTM, STP 977, Eds. R. T. Donaghe, Chaney, R. C., Silver, M. L., ASTM, Philadelphia, pp. 715-731.

Rowe, P. W. and Barden, L. (1964). "Importance of free ends in triaxial testing," *Journal of Soil Mechanics and Foundations Division*, ASCE, Vol. 90, No. SM1, pp. 1-27.

Saada, A. S. and Townsend, F. C. (1981). "Laboratory strength testing of soils, state of the art," *Laboratory Shear Strength of Soil, ASTM*, Special Technical Publication 740, eds. R. N. Yong and F. C. Townsend, ASTM, Philadelphia, pp. 7-77.

Sheng, D, Westerberg, B, Mattsson, H, and Axelsson, K. (1997). "Effects of end restraint and strain rate in triaxial tests," *Computers and Geotechnics*, Vol. 21, No. 3, pp.163-182.

Skempton, A. W., and Bjerrum, L. (1957), A Contribution to the Settlement Analyses of Foundations on Clay, *Geotechnique* 7, No. 3

Terzaghy, K, Peck, B. P., Mesri, G. (1996), Soil Mechanics in Engineering Practice, Wiley-Interscience, New York Vesic, A. S. (1972). "Expansion of cavities in infinite soil mass," *Journal of Soil Mechanics and Foundation Division*, ASCE, 98(3), pp.265-290.

Winterkorn H. F., and Fang, H. (1975), Foundation Engineering Handbook, Van Nostrand Reinhold Company, New York.

The invention claimed is:

1. an expandable jacket for maintaining uniform radial expansion of a cylindrical specimen, required for determining accurately the area of cross-section, volume change characteristics, deviator stress, shear strength, modulus of elasticity and Poisson's ratio, during triaxial compression tests on soils and intermediate geomaterials, and during unconfined compressive strength tests on cohesive soils, and cohesive intermediate geomaterials and soft rocks, the expandable jacket comprising:
   (i) a filter disc placed on a first porous disc to receive a cylindrical specimen, said porous disc resting on the rigid specimen base plate of the triaxial chamber;
   (ii) a second filter disc placed on the top of the cylindrical specimen;
   (iii) a second porous disc, placed on top of the second filter disc;
   (iv) a rigid specimen cap of the triaxial chamber placed on top of the second porous disc;
   (v) using a membrane expander, a membrane placed such that the membrane surrounds and is in contact with the cylindrical specimen, and extends to the porous discs and to the specimen base plate and cap;
   (vi) O-rings installed to seal the membrane to the specimen cap and base;
   (vii) a plurality of segmented plates assembled vertically such that the assembled segmented plates surround and are in contact with the membrane; wherein each of the segmented plates extend vertically beyond or up to the bottom of the first porous disc and top of the second porous disc; and wherein the segmented circular shaped plates are sufficiently thick not to bend and remain vertical, with the flexible lateral support provided by the bands or rings during the tests;
   (viii) at least one band or ring which stretch to permit radial expansion of the specimen, placed such that each of the at least one band or ring surround and are in contact with each of the segmented plates.

2. An expandable jacket according to claim 1, the expandable jacket further comprises:
   (i) wherein each of the segmented circular shaped plates contains at least one screw mount; wherein the screw mounts are located at least at one predetermined height of each of the segmented plates;
   (ii) wherein the segmented circular shaped plates and bands or rings are installed around the membrane containing cylindrical specimen by use of the removable attachments;
   (iii) wherein the flexible ring is calibrated using the calibration device to determine the modulus of elasticity of the membrane and combined modulus of elasticity of the expandable jacket.

3. A device for measuring the radial expansion of the cylindrical specimen of the concrete or intact rock core or jointed rock with or without expandable jacket during the compressive strength test for determining the compressive strength, elastic moduli and Poisson's ratio, the device comprising:
   (i) at least one LVDT attached to a spring-loaded U-frame or to a U-frame without springs; wherein the U-frame is in contact with the cylindrical specimen of the concrete core or intact rock core; wherein the U-frame is in contact with at least one band or ring of the expandable jacket surrounding the cylindrical specimen of jointed rock; wherein the U-frame rests on ball bearings such that during radial expansion of the cylindrical specimen, the U-frame prevents the LVDT from being inclined due to the vertical settlement of the cylindrical specimen; wherein the U-frame assembly is placed on a block resting on the bottom plate of the loading device.

4. The test system with a test device, flexible ring, triaxial type loading system or a conventional incremental loading system, and either a triaxial type chamber/sealed reservoir and a triaxial type control panel or an open reservoir, for performing three-dimensional consolidation test to determine three-dimensional coefficient of consolidation of soils and intermediate geomaterials, the test device and flexible ring comprising:
   (i) a filter disc placed on a first porous disc to receive a cylindrical specimen, said porous disc resting on the rigid specimen base plate;
   (ii) a second filter disc placed on the top of the cylindrical specimen;
   (iii) a second porous disc, placed on top of the second filter disc;
   (iv) a rigid specimen cap placed on top of the second porous disc;
   (v) a filter placed such that the filter surrounds and is in contact with the cylindrical specimen and porous discs;
   (vi) using a membrane expander, a membrane placed such that the membrane surrounds and is in contact with the filter; wherein for triaxial type chamber/sealed reservoir, the membrane extends beyond the filter and extends to the porous discs and the specimen base plate and cap; wherein for the open reservoir, the filter extends beyond the membrane and both the filter and membrane extends to the base plate and cap;
   (vii) O-rings installed to seal the membrane to the specimen cap and base;
   (viii) a plurality of segmented plates assembled vertically such that the assembled segmented plates surround and are in contact with the membrane; wherein each of the segmented plates extend vertically beyond or up to the bottom of the first and or top of the second porous disc; and wherein the segmented circular shaped plates are sufficiently thick, not to bend and remain vertical, with flexible lateral support provided by the bands or rings during the tests;
   (ix) at least one band or ring, which stretch to permit the radial expansion of the specimen while applying lateral pressure on the specimen, placed such that each of the at least one band or ring surround and are in contact with each of the segmented plates.

5. The test system according to claim 4, the flexible ring further comprises:
(i) wherein each of the segmented circular shaped plates contains at least one screw mount; wherein the screw mounts are located at least at one predetermined height of each of the segmented plates;
(ii) wherein the segmented circular shaped plates and bands or rings are installed around the membrane containing the filter and cylindrical specimen by use of the removable attachments;
(iii) wherein the flexible ring is calibrated using the calibration device to determine the modulus of elasticity of the membrane and combined modulus of elasticity of the flexible ring.

6. The test system consisting of a test device, a flexible ring, a triaxial type loading system or a conventional incremental loading system, LVDT, and either the triaxial type chamber/sealed reservoir and a the triaxial type control panel, or an open reservoir, for performing three-dimensional consolidation test to determine three-dimensional coefficient of consolidation of soils and intermediate geomaterials, the test device, flexible ring and LVDT comprising:
(i) a filter disc placed on a first porous disc to receive a cylindrical specimen, said porous disc resting on the rigid specimen base plate;
(ii) a second filter disc placed on the top of the cylindrical specimen;
(iii) a second porous disc, placed on top of the second filter disc;
(iv) a rigid specimen cap placed on top of the second porous disc;
(v) a filter placed such that the filter surrounds and is in contact with the cylindrical specimen and porous discs;
(vi) using a membrane expander, a membrane placed such that the membrane surrounds and is in contact with the filter; wherein for triaxial type chamber/sealed reservoir, the membrane extends beyond the filter and extends to the specimen base plate and cap; wherein for the open reservoir, the filter extends beyond the membrane and both the filter and membrane extend to the porous discs and the specimen base plate and cap;
(vii) O-rings installed to seal the membrane to the specimen cap and base;
(viii) a plurality of segmented plates assembled vertically such that the assembled segmented plates surround and are in contact with the membrane; wherein each of the segmented plates extend vertically beyond or up to the bottom of the first porous disc and top of the second porous disc; and wherein the segmented circular shaped plates are sufficiently thick, not to bend and remain vertical, with flexible lateral support provided by the bands or rings during the tests;
(xi) at least one band or ring, which stretch to permit radial expansion of th specimen while applying lateral pressure on the specimen, placed such that each of the at least one band or ring surround and are in contact with each of the segmented plates;
(x) for triaxial chamber/sealed reservoir, at least one LVDT which is capable of resist the high fluid pressure without any damage or malfunctioning of the electronics of LVDT, its connector, and its cable exit from the connector and its cable; wherein LVDT is removably attached to a spring-loaded U-frame; wherein LVDT with either radial connector or axial connector is used; wherein a specially designed sealed exit either for the sealed cable of for the rear end of the connector is provided from either top plate or cylindrical wall of the chamber/sealed reservoir;
(xi) the open reservoir, at least one LVDT capable to resist the water in the open reservoir and moisture without any damage or malfunctioning of electronics of LVDT, its connector and its cable; wherein LVDT is removably attached to a spring-loaded U-frame; wherein LVDT with either radial or axial connector is used; wherein LVDT with radial connector and/or its cable exits from top of the water level; wherein the sealed exit to the LVDT with axial connector is provided from the cylindrical wall of the open reservoir;
(xii) wherein the spring-loaded U-frame rests on ball bearings such that during radial expansion of the cylindrical specimen, the spring-loaded U-frame maintains the LVDT in proper horizontal alignment and prevents the LVDT from being inclined due to the vertical settlement of the cylindrical specimen.

7. The test system according to claim 6, the flexible ring further comprises:
(i) wherein each of the segmented circular shaped plates contains at least one screw mount; wherein the screw mounts are located at least at one predetermined height of each of the segmented plates;
(ii) wherein the segmented circular shaped plates and bands or rings are installed around the membrane containing the filter and cylindrical specimen by use of the removable attachments;
(iii) wherein the flexible ring is calibrated using the calibration device to determine the modulus of elasticity of the membrane and combined modulus of elasticity of the flexible ring.

8. The test device according to claim 6:
(i) wherein for high pressure sealed (i.e. hermetically sealed) LVDT with the radial connector sealed to the LVDT body, and sealed cable with sealed exit from the connector capable to resist the high fluid pressure without any damage or malfunctioning of the LVDT and its electronics;
(ii) wherein a specially designed sealed exit for the sealed cable of the radial connector is provided from the top metal plate of the chamber or sealed reservoir with at least one O-ring around the sealed cable and at least one O-ring around the threaded opening and its threaded metal plug.

9. The test device according to claim 6:
(i) wherein high pressure sealed LVDT with the axial connector sealed to the LVDT body and with a threaded length at the rear end of the LVDT body, a specially designed sealed exit is provided to the rear end of the LVDT body through the metal cylindrical wall of the chamber or sealed reservoir, using an internally threaded metal tube weld connected to the metal cylindrical wall;
(ii) wherein the threaded length of the LVDT body is fastened to the threaded metal tube and sealed with O-rings.

10. The test device according to claim 6:
a. for LVDT with axial connector for open reservoir, a specially designed sealed exit is provided from rear end of the LVDT body through the metal cylindrical wall of the open reservoir, using the internally threaded metal tube weld connected to the metal cylindrical wall;

b. wherein the threaded length of the LVDT body is fastened to the threaded metal tube and sealed with O-rings.

11. The test system with a test device, flexible ring, triaxial type loading system or a conventional incremental loading system, and either the triaxial type chamber/sealed reservoir and the triaxial type control panel or the open reservoir, for performing three-dimensional consolidation to determine coefficient of consolidation in vertical direction of soils and intermediate geomaterials and to determine three-dimensional settlement characteristics of soils and intermediate geomaterials, the test device and flexible ring comprising:

(i) a filter disc placed on a first porous disc to receive a cylindrical specimen, said porous disc resting on the rigid specimen base plate;
(ii) a second filter disc placed on the top of the cylindrical specimen;
(iii) a second porous disc, placed on top of the second filter disc;
(iv) a rigid specimen cap placed on top of the second porous disc;
(v) using a membrane expander, a membrane placed such that the membrane surrounds and is in contact with the cylindrical specimen; wherein the membrane extends to the porous discs and the specimen base plate and cap;
(vi) O-rings installed to seal the membrane to the specimen cap and base;
(vii) a plurality of segmented plates assembled vertically such that the assembled segmented plates surround and are in contact with the membrane; wherein each of the segmented plates extend vertically beyond or up to the bottom of the first and or top of the second porous disc; and wherein the segmented circular shaped plates are sufficiently thick, not to bend and remain vertical, with flexible lateral support provided by the bands or rings during the tests;
(viii) at least one band or ring, which stretch to permit radial expansion of the specimen while applying lateral pressure on the specimen, placed such that each of the at least one band or ring surround and are in contact with each of the segmented plates.

12. The test system of according to claim 11, the flexible ring further comprises:

(i) wherein each of the segmented circular shaped plates contains at least one screw mount; wherein the screw mounts are located at least at one predetermined height of each of the segmented plates;
(ii) wherein the segmented circular shaped plates and bands or rings are installed around the membrane containing the filter and cylindrical specimen by use of the removable attachments;
(iii) wherein the flexible ring is calibrated using the calibration device to determine the modulus of elasticity of the membrane and combined modulus of elasticity of the flexible ring.

13. The test system consisting of a test device, flexible ring, a triaxial type loading system or a conventional incremental loading system, LVDT, and triaxial type chamber/sealed reservoir and triaxial type control panel or the open reservoir, for performing three-dimensional consolidation tests to determine the coefficient of consolidation in vertical direction of soils and intermediate geomaterials and to determine three-dimensional settlement characteristics of soils and intermediate geomaterials, the test device, flexible ring, and LVDT comprising:

(i) a filter disc placed on a first porous disc to receive a cylindrical specimen, said porous disc resting on the rigid specimen base plate;
(ii) a second filter disc placed on the top of the cylindrical specimen;
(iii) a second porous disc, placed on top of the second filter disc;
(iv) a rigid specimen cap placed on top of the second porous disc;
(v) a membrane placed such that the membrane surrounds and is in contact with the cylindrical specimen; wherein the membrane extends to the porous discs and the specimen base plate and cap;
(vi) O-rings installed to seal the membrane to the specimen cap and base;
(vii) a plurality of segmented plates assembled vertically such that the assembled segmented plates surround and are in contact with the membrane; wherein each of the segmented plates extend vertically beyond or up to the bottom of the first porous disc and or top of the second porous disc; and wherein the segmented circular shaped plates are sufficiently thick, not to bend and remain vertical, with flexible lateral support provided by the bands or rings;
(viii) at least one band or ring, which stretch to permit radial expansion of the specimen, placed such that each of the at least one band or ring surround and are in contact with each of the segmented plates;
(ix) for triaxial chamber/sealed reservoir, at least one LVDT which is capable to resist the high fluid pressure without any damage or malfunctioning of the electronics of LVDT, its connector, and its cable exit from the connector and its cable; wherein LVDT is removably attached to a spring-loaded U-frame; wherein LVDT with either radial connector or axial connector is used; wherein a specially designed sealed exit either for the sealed cable or for the rear end of the connector is provided from either top plate or cylindrical wall of the chamber/sealed reservoir;
(x) the open reservoir, at least one LVDT capable to resist the water in the open reservoir and moisture without any damage or malfunctioning of electronics of LVDT, its connector and its cable; wherein LVDT is removably attached to a spring-loaded U-frame; wherein LVDT with either radial or axial connector is used; wherein LVDT with radial connector and/or its cable exits from top of the water level; wherein the sealed exit to the LVDT with axial connector is provided from the cylindrical wall of the open reservoir;
(xi) wherein the spring-loaded U-frame rests on ball bearings such that during radial expansion of the cylindrical specimen, the spring-loaded U-frame maintains the LVDT in proper horizontal alignment and prevents the LVDT from being inclined due to the vertical settlement of the cylindrical specimen.

14. The test system according to claim 13, (i) wherein each of the segmented circular shaped plates contains at least one screw mount; wherein the screw mounts are located at least at one predetermined height of each of the segmented plates;
(ii) wherein the segmented circular shaped plates and bands or rings are installed around the membrane containing the cylindrical specimen by use of the removable attachments;

(iii) wherein the flexible ring is calibrated using the calibration device to determine the modulus of elasticity of the membrane and combined modulus of elasticity of the flexible ring.

15. The test device according to claim 13:
(i) wherein for high pressure sealed (i.e. hermetically sealed) LVDT with the radial connector sealed to the LVDT body, and sealed cable with sealed exit from the connector capable to resist the high fluid pressure without any damage or malfunctioning of the LVDT and its electronics;
(ii) wherein a specially designed sealed exit for the sealed cable of the radial connector is provided from the top metal plate of the chamber or sealed reservoir with at least one O-ring around the sealed cable and at least one O-ring around the threaded opening and its threaded metal plug.

16. The test device according to claim 13:
(i) wherein high pressure sealed LVDT with the axial connector sealed to the LVDT body and with a threaded length at the rear end of the LVDT body, a specially designed sealed exit is provided to the rear end of the LVDT body through the metal cylindrical wall of the chamber or sealed reservoir, using an internally threaded metal tube weld connected to the metal cylindrical wall;
(ii) wherein the threaded length of the LVDT body is fastened to the threaded metal tube and sealed with O-rings.

17. The test device according to claim 13: for LVDT with axial connector for open reservoir, a specially designed sealed exit is provided from rear end of the LVDT body through the metal cylindrical wall of the open reservoir, using the internally threaded metal tube weld connected to the metal cylindrical wall; wherein the threaded length of the LVDT body is fastened to the threaded metal tube and sealed with O-rings.

18. The test system with a test device, flexible ring, triaxial type loading system or a conventional incremental loading system, and either a triaxial type chamber/sealed reservoir and a triaxial type control panel or and the open reservoir, for performing three-dimensional consolidation test to determine coefficient of consolidation of soils and intermediate geomaterials in horizontal direction, the test device and flexible ring comprising:
(i) a filter disc placed on a rigid specimen base plate to receive a cylindrical specimen;
(ii) a second filter disc placed on the top of the cylindrical specimen;
(iii) a rigid specimen cap placed on top of the second filter disc;
(iv) a filter placed such that the filter surrounds and is in contact with the cylindrical specimen; and wherein the filter extends around the base plate and cap;
(v) using the membrane expander, the membrane placed such that the membrane surrounds and is in contact with the filter; wherein for triaxial type chamber/sealed reservoir, the membrane extends beyond the filter and extends to the specimen base plate and cap; wherein for the open reservoir, the filter extends beyond the membrane and both the filter and membrane extend to the base plate and cap;
(vi) O-rings installed to seal the membrane to the specimen cap and base;
(vii) a plurality of segmented plates assembled vertically such that the assembled segmented plates surround and are in contact with the membrane; wherein each of the segmented plates extend vertically beyond or up to the bottom of the first and or top of the second porous disc; and wherein the segmented circular shaped plates are sufficiently thick, not to bend and remain vertical, with flexible lateral support provided by the bands or rings during the tests;
(viii) at least one band or ring, which stretch and permit the radial expansion of the specimen while applying lateral pressure on the specimen, placed such that each of the at least one band or ring surround and are in contact with each of the segmented plates.

19. The test system according to claim 18, the flexible ring further comprises:
(i) wherein each of the segmented circular shaped plates contains at least one screw mount; wherein the screw mounts are located at least at one predetermined height of each of the segmented plates;
(ii) wherein the segmented circular shaped plates and bands or rings are installed around the membrane containing the cylindrical specimen by use of the removable attachments;
(iii) wherein the flexible ring is calibrated using the calibration device to determine the modulus of elasticity of the membrane and combined modulus of elasticity of the flexible ring.

20. The test system consisting of a test device, a flexible ring, LVDT, a triaxial type loading system or a conventional incremental loading system and either a triaxial type chamber/sealed reservoir or an open reservoir, for performing three-dimensional consolidation test to determine coefficient of consolidation of soils and intermediate geomaterials in horizontal direction, the test device, flexible ring and LVDT comprising:
(i) a filter disc placed on a rigid specimen base plate to receive a cylindrical specimen;
(ii) a second filter disc placed on the top of the cylindrical specimen;
(iii) a rigid specimen cap placed on top of the second filter disc;
(iv) a filter placed such that the filter surrounds and is in contact with the cylindrical specimen and rigid specimen base plate and cap; wherein filter extends beyond the membrane;
(v) using a membrane expander, a membrane placed such that the membrane surrounds and is in contact with the filter; wherein for triaxial type chamber/sealed reservoir, the membrane extends beyond the filter and extends to the specimen base plate and cap; wherein the filter extends beyond the membrane and both the filter and membrane extend to the base plate;
(vi) O-rings installed to seal the membrane to the specimen cap and base plate;
(vii) a plurality of segmented plates assembled vertically such that the assembled segmented plates surround and are in contact with the membrane; wherein each of the segmented plates extend vertically beyond or up to the bottom of the first porous disc and or top of the second porous disc; and wherein the segmented circular shaped plates are sufficiently thick, not to bend and remain vertical, with flexible support provided by the bands or rings during the tests;
(viii) at least one band or ring, which stretch to permit radial expansion of the specimen while applying lateral pressure on the specimen, placed such that each of the at least one band or ring surround and are in contact with each of the segmented plates;

(ix) for triaxial chamber/sealed reservoir, at least one LVDT which is capable to resist the high fluid pressure without any damage or malfunctioning of the electronics of LVDT, its connector, and its cable exit from the connector and its cable; wherein LVDT is removably attached to a spring-loaded U-frame; wherein LVDT with either radial connector or axial connector is used; wherein a specially designed sealed exit either for the sealed cable or for the rear end of the connector is provided from either top plate or cylindrical wall of the chamber/sealed reservoir;

(x) the open reservoir, at least one LVDT capable to resist the water in the open reservoir and moisture without any damage or malfunctioning of electronics of LVDT, its connector and its cable; wherein LVDT is removably attached to a spring-loaded U-frame; wherein LVDT with either radial or axial connector is used; wherein LVDT with radial connector and/or its cable exits from top of the water level; wherein the sealed exit to the LVDT with axial connector is provided from the cylindrical wall of the open reservoir;

(xi) wherein the spring-loaded U-frame rests on ball bearings such that during radial expansion of the cylindrical specimen, the spring-loaded U-frame maintains the LVDT in proper horizontal alignment and prevents the LVDT from being inclined due to the vertical settlement of the cylindrical specimen.

21. The test system according to claim 20, the flexible ring further comprises:
(i) wherein each of the segmented circular shaped plates contains at least one screw mount; wherein the screw mounts are located at least at one predetermined height of each of the segmented plates;
(ii) wherein the segmented circular shaped plates and bands or rings are installed around the membrane containing the filter and cylindrical specimen by use of the removable attachments;
(iii) wherein the flexible ring is calibrated using the calibration device to determine the modulus of elasticity of the membrane and combined modulus of elasticity of the flexible ring.

22. The test device according to claim 20: for LVDT with axial connector for open reservoir, a specially designed sealed exit is provided from rear end of the LVDT body through the metal cylindrical wall of the open reservoir, using the internally threaded metal tube weld connected to the metal cylindrical wall; wherein the threaded length of the LVDT body is fastened to the threaded metal tube and sealed with O-rings.

23. According to claim 20: wherein for high pressure sealed (i.e. hermetically sealed) LVDT with the radial connector sealed to the LVDT body, and sealed cable with sealed exit from the connector capable to resist the high fluid pressure without any damage or malfunctioning of the LVDT and its electronics; wherein a specially designed sealed exit for the sealed cable of the radial connector is provided from the top metal plate of the chamber or sealed reservoir with at least one O-ring around the sealed cable and at least one O-ring around the threaded opening and its threaded metal plug.

24. According to claim 20: high pressure sealed LVDT with the axial connector sealed to the LVDT body and with a threaded length at the rear end of the LVDT body, a specially designed sealed exit is provided to the rear end of the LVDT body through the metal cylindrical wall of the chamber or sealed reservoir, using an internally threaded metal tube weld connected to the metal cylindrical wall; wherein the threaded length of the LVDT body is fastened to the threaded metal tube and sealed with O-rings.

25. Removable attachments for installation of segmented circular shaped plates and bands or rings, the removal attachments comprising:
(i) at least a pair of half-circular brackets, or at least one horizontal hook and loop strap, or brackets and horizontal hook and loop straps, both in combination, for vertical positioning of each of the segmented circular shaped plates; wherein the segmented circular shaped plates are vertically assembled and screwed to brackets or hook and loop straps by screw mounts at least at one predetermined height and at least one band or ring placed such that each of the bands or rings surround and are in contact with each of the segmented plates;
wherein after assembling the segmental plates and bands or rings properly, the removable attachments of brackets or straps are removed.

26. A calibration device for determining the lateral resistance and modulus of elasticity of membrane surrounding the porous tube and for determining a combined modulus of elasticity of the expandable jacket or flexible ring, which is required for applying a correction to the deviator stress, shear strength and to determine the value of lateral resistance, the calibration device comprising:
(i) a water reservoir, wherein the water reservoir has a vertical position defined by a vertically movable bracket;
(ii) a horizontal porous tube, fastened to caps on both ends and connected to the vertically movable water reservoir via at least one tube and valve, wherein on the other end, at least one tube exits the porous tube and cap with a valve to initially flush out air bubbles from water; wherein the porous tube is configured to be surrounded and sealed by a membrane;
(iii) wherein the porous tube surrounded by the membrane is further configured to be surrounded by the flexible ring or expandable jacket comprising another membrane with or without filter, the segmented circular shaped plates, and at least one band or ring.

27. An expandable jacket for maintaining uniform radial expansion of a cylindrical specimen, required for determining accurately the area of cross-section, volume change characteristics, deviator stress, shear strength, modulus of elasticity and Poisson's ratio, during triaxial compression tests on soils and intermediate geomaterials, and during unconfined compressive strength tests on cohesive soils, and cohesive intermediate geomaterials and soft rocks, the expandable jacket with LVDT comprising:
(i) a filter disc placed on a first porous disc to receive a cylindrical specimen, said porous disc resting on the rigid specimen base plate of the triaxial chamber;
(ii) a second filter disc placed on the top of the cylindrical specimen;
(iii) a second porous disc, placed on top of the second filter disc;
(iv) a rigid specimen cap of the triaxial chamber placed on top of the second porous disc;
(v) using a membrane expander, a membrane placed such that the membrane surrounds and is in contact with the cylindrical specimen, and extends to the porous discs and to the specimen base plate and cap;
(vi) O-rings installed to seal the membrane to the specimen cap and base;
(vii) a plurality of segmented plates assembled vertically such that the assembled segmented plates surround and are in contact with the membrane; wherein each of the segmented plates extend vertically beyond or up to the bottom of the first porous disc and top of the second porous disc; and wherein the segmented circular shaped plates are sufficiently thick not to bend and remain vertical, with the flexible lateral support provided by the bands or rings during the tests;

(viii) at least one band or ring which stretch to permit radial expansion of of the specimen, placed such that each of the at least one band or ring surround and are in contact with each of the segmented plates;

(ix) for triaxial chamber/sealed reservoir, at least one LVDT which is capable to resist the high fluid pressure without any damage or malfunctioning of the electronics of LVDT, its connector, and its cable exit from the connector and its cable; wherein LVDT is removably attached to a spring-loaded U-frame; wherein LVDT with either radial connector or axial connector is used; wherein a specially designed sealed exit either for the sealed cable or for the rear end of the connector is provided from either top plate or cylindrical wall of the chamber/sealed reservoir;

(x) the open reservoir, at least one LVDT capable to resist the water in the open reservoir and moisture without any damage or malfunctioning of electronics of LVDT, its connector and its cable; wherein LVDT is removably attached to a spring-loaded U-frame; wherein LVDT with either radial or axial connector is used; wherein LVDT with radial connector and/or its cable exits from top of the water level; wherein the sealed exit to the LVDT with axial connector is provided from the cylindrical wall of the open reservoir;

(xi) wherein the spring-loaded U-frame rests on ball bearings such that during radial expansion of the cylindrical specimen, the spring-loaded U-frame maintains the LVDT in proper horizontal alignment and prevents the LVDT from being inclined due to the vertical settlement of the cylindrical specimen.

28. The test device according to claim 27 further comprises:

(i) wherein each of the segmented circular shaped plates contains t least one screw mount; wherein the screw mounts are located at least at one predetermined height of each of the segmented plates;

(ii) wherein the segmented circular shaped plates and bands or rings are installed around the membrane containing the cylindrical specimen by use of the removable attachments;

(iii) wherein the flexible ring is calibrated using the calibration device to determine the modulus of elasticity of the membrane and combined modulus of elasticity of the flexible ring.

29. According to claim 27: for LVDT with axial connector for open reservoir, a specially designed sealed exit is provided from rear end of the LVDT body through the metal cylindrical wall of the open reservoir, using the internally threaded metal tube weld connected to the metal cylindrical wall; wherein the threaded length of the LVDT body is fastened to the threaded metal tube and sealed with O-rings.

30. According to claim 27: wherein for high pressure sealed (i.e. hermetically sealed) LVDT with the radial connector sealed to the LVDT body, and sealed cable with sealed exit from the connector capable to resist the high fluid pressure without any damage or malfunctioning of the LVDT and its electronics; wherein a specially designed sealed exit for the sealed cable of the radial connector is provided from the top metal plate of the chamber or sealed reservoir with at least one O-ring around the sealed cable and at least one O-ring around the threaded opening and its threaded metal plug.

31. According to claim 27: high pressure sealed LVDT with the axial connector sealed to the LVDT body and with a threaded length at the rear end of the LVDT body, a specially designed sealed exit is provided to the rear end of the LVDT body through the metal cylindrical wall of the chamber or sealed reservoir, using an internally threaded metal tube weld connected to the metal cylindrical wall; wherein the threaded length of the LVDT body is fastened to the threaded metal tube and sealed with O-rings.

* * * * *